US010533050B2

(12) United States Patent
Houhou et al.

(10) Patent No.: US 10,533,050 B2
(45) Date of Patent: *Jan. 14, 2020

(54) METHODS AND COMPOSITIONS FOR LIVER CANCER THERAPY

(75) Inventors: Leïla Houhou, Montpellier (FR); Anne-Sophie Dumé, Montpellier (FR); Dominique Joubert, Sète (FR); Frédéric Hollande, Les Matelles (FR)

(73) Assignees: Institut National de la Sante et de la Recherche Medicale (INSERM), Paris (FR); Centre National de la Recherche Scientifique (CNRS), Paris (FR); Les Laboratories Servier, Suresnes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/189,403

(22) Filed: Jul. 22, 2011

(65) Prior Publication Data
US 2012/0020961 A1 Jan. 26, 2012

Related U.S. Application Data

(60) Provisional application No. 61/367,851, filed on Jul. 26, 2010, provisional application No. 61/476,204, filed on Apr. 15, 2011.

(51) Int. Cl.
A61K 39/395 (2006.01)
A61K 38/22 (2006.01)
A61K 39/00 (2006.01)
C07K 14/595 (2006.01)
C07K 16/26 (2006.01)
A61K 45/06 (2006.01)

(52) U.S. Cl.
CPC .................................. C07K 16/26 (2013.01)

(58) Field of Classification Search
None
See application file for complete search history.

(56) References Cited

U.S. PATENT DOCUMENTS

2003/0021786 A1* 1/2003 Gevas et al. ............... 424/146.1
2007/0248608 A1* 10/2007 Grimes ....................... 424/142.1
2008/0187577 A1* 8/2008 Singh et al. ................. 424/450
2011/0117086 A1* 5/2011 Pannequin et al. ......... 424/133.1
2011/0171213 A1* 7/2011 Houhou et al. ............ 424/133.1
2011/0177062 A1* 7/2011 Floch et al. ................ 424/133.1
2011/0177063 A1* 7/2011 Pannequin et al. ......... 424/133.1
2011/0229488 A1* 9/2011 Floch et al. ................ 424/158.1
2015/0071912 A1* 3/2015 Houhou et al. ............ 424/133.1

FOREIGN PATENT DOCUMENTS

WO WO 2007/135542 A2 11/2007
WO WO 20087/076454 A1 6/2008
WO WO 2011/083089 AI 7/2011

OTHER PUBLICATIONS

Caplin (Journal of Hepatology, 1999, 30:519-526).*
Tzartos et al. (Methods in Molecular Biology, 1996, 66:55-66).*
Rudikoff et al. (Proceedings of the National Academy of Sciences, 1982, 79:1979-1983).*
MacCallum et al. (Journal of Molecular Biology, 1996, 262:732-745).*
De Pascalis et al. (Journal of Immunology, 2002, 169:3076-3084).*
Casset et al. (Biochemical and Biophysical Research Communications, 2003, 307:198-205).*
Vajdos et al. (Journal of Molecular Biology, 2002, 320:415-428).*
Holm et al. (Molecular Immunology, 2007:1075-1084).*
Chen et al. (Journal of Molecular Biology, 1999, 293:865-881).*
Caplin et al., 1999 "Expression and processing of gastrin in hepatocellular carcinoma, fibrolamellar carcinoma and cholangiocarcinoma," *Journal of Hepatology* 30:519-526.
Llovet et al., 2003 "Hepatocellular carcinoma," *Lancet* 362:1907-17.
Thorgeirsson et al., "Molecular pathogenesis of human hepatocellular carcinoma," *Nature Genetics* 31:339-346.
Rengifo-Cam et al., 2004, "Role of Progastrins and Gastrins and Their Receptors in GI and Pancreatic Cancers: Targets for Treatment," *Curr. Pharm. Des.* vol. 10:2345-2358.
Konturek, et al., 2003 "Progastrin and its products from patients with chronic viral hepatitis and liver cirrhosis," *Scandinavian Journal of Gastroenterology* 38:643-647.
PCT International Search Report and Written Opinion of the International Searching Authority from PCT/EP2011/062686 dated Nov. 9, 2011.

* cited by examiner

*Primary Examiner* — Julie Wu
(74) *Attorney, Agent, or Firm* — Buchanan Ingersoll & Rooney PC

(57) ABSTRACT

The present disclosure provides methods of treating liver cancer and preventing liver cancer recurrence with anti-progastrin antibodies, methods of monitoring treatment efficacy of anti-progastrin therapy for liver cancer, and compositions useful therefore.

11 Claims, 59 Drawing Sheets

Specification includes a Sequence Listing.

FIG. 1

```
Preprogastrin:  M QRLCVYVLIF ALALAAFSEA SWKPRSQQPD APLGTGANRD LELPWLEQQG
                -21                      -11         1          11         21

PASHHRRQLG PQGPPHLVAD PSKKQGPWLE EEEEAYGWMD FGRRSAEDEN
                31         41         51         61         71

Progastrin:     PASHHRRQLG PQGPPHLVAD PSKKQGPWLE EEEEAYGWMD FGRRSAEDEN
                 1          11         21         31         41

SWKPRSQQPD APLGTGANRD LELPWLEQQG
                51         61         71

G34:            PASHHRRQLG PQGPPHLVAD PSKKQGPWLE EEEEAYGWMD F-NH₂
                 1          11         21         31         41

G34-Gly:        QLG PQGPPHLVAD PSKKQGPWLE EEEEAYGWMD FG
                 1   11         21         31         41

G17:            QGPWLE EEEEAYGWMD F-NH₂
                 1      11         21

G17-Gly:        QGPWLE EEEEAYGWMD FG
                 1      11         21

CTFP:                                         SAEDEN
                                              71
```

FIG. 2A mV$_H$ MAb3

| | | | | | | | | | | | | | | | | |
|---|---|---|---|---|---|---|---|---|---|---|---|---|---|---|---|---|
| gag | gtt | cag | ctc | cag | cag | tct | ggg | act | gtg | ctg | gca | agg | cct | ggg | gct | 48 |
| Glu | Val | Gln | Leu | Gln | Gln | Ser | Gly | Thr | Val | Leu | Ala | Arg | Pro | Gly | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | gtg | aag | atg | tcc | tgc | aag | gct | tct | ggc | tac | atc | ttt | acc | agc | tac | 96 |
| Ser | Val | Lys | Met | Ser | Cys | Lys | Ala | Ser | Gly | Tyr | Ile | Phe | Thr | Ser | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| tgg | gta | cac | tgg | gtt | aaa | cag | agg | cct | gga | cag | ggt | cta | gaa | tgg | att | 144 |
| Trp | Val | His | Trp | Val | Lys | Gln | Arg | Pro | Gly | Gln | Gly | Leu | Glu | Trp | Ile | |
| | | | 35 | | | | | 40 | | | | | 45 | | | |

| | | | | | | | | | | | | | | | | |
|---|---|---|---|---|---|---|---|---|---|---|---|---|---|---|---|---|
| ggt | ggt | ttt | tat | cct | gga | aat | agt | gat | tct | agg | tac | aac | cag | aaa | ttc | 192 |
| Gly | Gly | Phe | Tyr | Pro | Gly | Asn | Ser | Asp | Ser | Arg | Tyr | Asn | Gln | Lys | Phe | |
| | 50 | | | | | 55 | | | | | 60 | | | | | |

| | | | | | | | | | | | | | | | | |
|---|---|---|---|---|---|---|---|---|---|---|---|---|---|---|---|---|
| aag | ggc | aag | gcc | aca | ctg | act | gca | gtc | aca | tcc | gcc | agt | act | gcc | tac | 240 |
| Lys | Gly | Lys | Ala | Thr | Leu | Thr | Ala | Val | Thr | Ser | Ala | Ser | Thr | Ala | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atg | gac | ctc | agc | agc | ctg | aca | aat | gag | gac | tct | gcg | gtc | tat | ttc | tgt | 288 |
| Met | Asp | Leu | Ser | Ser | Leu | Thr | Asn | Glu | Asp | Ser | Ala | Val | Tyr | Phe | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | aga | aga | gat | agt | ccc | cag | tac | tgg | ggc | caa | ggc | acc | act | ctc | aca | 336 |
| Thr | Arg | Arg | Asp | Ser | Pro | Gln | Tyr | Trp | Gly | Gln | Gly | Thr | Thr | Leu | Thr | |
| | | | 100 | | | | | 105 | | | | | 110 | | | |

| | | | |
|---|---|---|---|
| gtc | tcc | tca | 345 |
| Val | Ser | Ser | |
| | | 115 | |

FIG. 2B mV$_L$ MAb3

| | | | | | | | | | | | | | | | |
|---|---|---|---|---|---|---|---|---|---|---|---|---|---|---|---|
| gat | gtt | ttg | atg | acc | caa | act | cca | ctc | tcc | ctg | cct | gtc | agt | ctt | gga | 48 |
| Asp | Val | Leu | Met | Thr | Gln | Thr | Pro | Leu | Ser | Leu | Pro | Val | Ser | Leu | Gly |
| 1 | | | | 5 | | | | | 10 | | | | | 15 | | gat caa gcc tcc atc tct tgc aga tct agt cag agc att gta cat agt   96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct   144
Asn Gly Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca   192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc   240
Asp Arg Phe Ser Gly Ser Gly Ser Gly Thr Asp Phe Thr Leu Lys Ile
65                  70                  75                  80 agc aga ctg gag gct gag gat ctg gga gtt tat tac tgc ttt caa ggt   288
Ser Arg Leu Glu Ala Glu Asp Leu Gly Val Tyr Tyr Cys Phe Gln Gly
                85                  90                      95 tca cat gtt ccg ttc acg ttc gga ggg ggg acc aag ctg gaa ata aaa   336
Ser His Val Pro Phe Thr Phe Gly Gly Gly Thr Lys Leu Glu Ile Lys
            100                 105                 110

FIG. 2C mV$_H$ MAb4

| | | | | | | | | | | | | | | | | |
|---|---|---|---|---|---|---|---|---|---|---|---|---|---|---|---|---|
| cag | gtt | cag | ttg | cag | cag | tct | gga | gct | gag | ctg | atg | aag | cca | ggg | gcc | 48 |
| Gln | Val | Gln | Leu | Gln | Gln | Ser | Gly | Ala | Glu | Leu | Met | Lys | Pro | Gly | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tca | gtg | aag | ata | tcc | tgc | aag | gct | act | ggc | tac | aca | ttc | agt | agc | tcc | 96 |
| Ser | Val | Lys | Ile | Ser | Cys | Lys | Ala | Thr | Gly | Tyr | Thr | Phe | Ser | Ser | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| tgg | ata | gag | tgg | tta | aaa | cag | agg | cct | gga | cat | ggc | ctt | gag | tgg | att | 144 |
| Trp | Ile | Glu | Trp | Leu | Lys | Gln | Arg | Pro | Gly | His | Gly | Leu | Glu | Trp | Ile | |
| | | | 35 | | | | | 40 | | | | | 45 | | | |

| | | | | | | | | | | | | | | | | |
|---|---|---|---|---|---|---|---|---|---|---|---|---|---|---|---|---|
| gga | gag | ttt | tta | cct | gga | agt | ggt | agt | aca | gac | tac | aat | gag | aag | ttc | 192 |
| Gly | Glu | Phe | Leu | Pro | Gly | Ser | Gly | Ser | Thr | Asp | Tyr | Asn | Glu | Lys | Phe | |
| | | 50 | | | | | 55 | | | | | 60 | | | | |

| | | | | | | | | | | | | | | | | |
|---|---|---|---|---|---|---|---|---|---|---|---|---|---|---|---|---|
| aag | ggc | aag | gcc | aca | ttc | act | gca | gac | aca | tcc | tcc | gac | aca | gcc | tac | 240 |
| Lys | Gly | Lys | Ala | Thr | Phe | Thr | Ala | Asp | Thr | Ser | Ser | Asp | Thr | Ala | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atg | cta | ctc | agc | agc | ctg | aca | tct | gag | gac | tct | gcc | gtc | tat | tac | tgt | 288 |
| Met | Leu | Leu | Ser | Ser | Leu | Thr | Ser | Glu | Asp | Ser | Ala | Val | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | act | gat | ggt | aat | tat | gac | tgg | ttt | gct | tac | tgg | ggc | caa | ggg | act | 336 |
| Ala | Thr | Asp | Gly | Asn | Tyr | Asp | Trp | Phe | Ala | Tyr | Trp | Gly | Gln | Gly | Thr | |
| | | | 100 | | | | | 105 | | | | | 110 | | | |

| | | | | | |
|---|---|---|---|---|---|
| ctg | gtc | act | gtc | tct | gca | 354 |
| Leu | Val | Thr | Val | Ser | Ala | |
| | | 115 | | | | |

FIG. 2D mV$_L$ MAb4

```
gat ctt gtg atg acc caa act cca ctc tcc ctg cct gtc agt ctt gga    48
Asp Leu Val Met Thr Gln Thr Pro Leu Ser Leu Pro Val Ser Leu Gly
 1               5                  10                  15 gat caa gcc tcc atc tct tgc aga tct agt cag agc ctt gta cac agt    96
Asp Gln Ala Ser Ile Ser Cys Arg Ser Ser Gln Ser Leu Val His Ser
                 20                  25                  30 agt gga gtc acc tat tta cat tgg tac ctg cag aag cca ggc cag tct   144
Ser Gly Val Thr Tyr Leu His Trp Tyr Leu Gln Lys Pro Gly Gln Ser
             35                  40                  45 cca aag ctc ctg atc tac aaa gtt tcc aac cga ttt tct ggg gtc cca   192
Pro Lys Leu Leu Ile Tyr Lys Val Ser Asn Arg Phe Ser Gly Val Pro
         50                  55                  60 gac agg ttc agt ggc agt gga tca ggg aca gat ttc aca ctc aag atc   240
Asp Arg Phe Ser Gly Ser Gly Ser Gly Thr Asp Phe Thr Leu Lys Ile
 65                  70                  75                  80 agc aga gtg gag gct gag gat ctg gga gtt tat ttc tgc tct caa agt   288
Ser Arg Val Glu Ala Glu Asp Leu Gly Val Tyr Phe Cys Ser Gln Ser
                 85                  90                  95 aca cat gtt cct ccc acg ttc ggc tcg ggg aca aag ttg gaa ata aaa   336
Thr His Val Pro Pro Thr Phe Gly Ser Gly Thr Lys Leu Glu Ile Lys
             100                 105                 110
```

FIG. 2E mV$_H$ MAb8

| | | | | | | | | | | | | | | | | |
|---|---|---|---|---|---|---|---|---|---|---|---|---|---|---|---|---|
| gaa | gtg | cag | ctg | gtg | gag | tct | ggg | gga | ggc | tta | gtg | aag | cct | gga | ggg | 48 |
| Glu | Val | Gln | Leu | Val | Glu | Ser | Gly | Gly | Gly | Leu | Val | Lys | Pro | Gly | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | ctg | aaa | ctc | tcc | tgt | gca | gcc | tct | gga | ttc | act | ttc | act | acc | tat | 96 |
| Ser | Leu | Lys | Leu | Ser | Cys | Ala | Ala | Ser | Gly | Phe | Thr | Phe | Thr | Thr | Tyr | |
| | | 20 | | | | | 25 | | | | | 30 | | | | |

| | | | | | | | | | | | | | | | | |
|---|---|---|---|---|---|---|---|---|---|---|---|---|---|---|---|---|
| gcc | atg | tct | tgg | gtt | cgc | cag | act | ccg | gag | aag | agg | ctg | gag | tgg | gtc | 144 |
| Ala | Met | Ser | Trp | Val | Arg | Gln | Thr | Pro | Glu | Lys | Arg | Leu | Glu | Trp | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gca | acc | att | agt | agt | ggt | ggt | act | tac | acc | tac | tat | cca | gac | agt | gtg | 192 |
| Ala | Thr | Ile | Ser | Ser | Gly | Gly | Thr | Tyr | Thr | Tyr | Tyr | Pro | Asp | Ser | Val | |
| | | 50 | | | | | 55 | | | | | 60 | | | | |

| | | | | | | | | | | | | | | | | |
|---|---|---|---|---|---|---|---|---|---|---|---|---|---|---|---|---|
| aag | ggt | cga | ttc | acc | atc | tcc | aga | gac | aat | gcc | aag | aac | gcc | cta | tac | 240 |
| Lys | Gly | Arg | Phe | Thr | Ile | Ser | Arg | Asp | Asn | Ala | Lys | Asn | Ala | Leu | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctg | caa | atg | agc | agt | ctg | agg | tct | gag | gac | acg | gcc | atg | tat | tac | tgt | 288 |
| Leu | Gln | Met | Ser | Ser | Leu | Arg | Ser | Glu | Asp | Thr | Ala | Met | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | aca | cag | ggg | aat | tac | tct | ttg | gac | ttc | tgg | ggc | caa | ggc | acc | tct | 336 |
| Ala | Thr | Gln | Gly | Asn | Tyr | Ser | Leu | Asp | Phe | Trp | Gly | Gln | Gly | Thr | Ser | |
| | | | | 100 | | | | | 105 | | | | | 110 | | |

| | | | | |
|---|---|---|---|---|
| ctc | aca | gtc | tcc | tca | 351 |
| Leu | Thr | Val | Ser | Ser | |
| | | 115 | | | |

FIG. 2F mV$_L$ MAb8

| | | | | | | | | | | | | | | | |
|---|---|---|---|---|---|---|---|---|---|---|---|---|---|---|---|
| gac | att | gtg | atg | acg | cag | gct | gca | tcc | tct | aat | cca | gtc | act | ctt | gga | 48 |
| Asp | Ile | Val | Met | Thr | Gln | Ala | Ala | Ser | Ser | Asn | Pro | Val | Thr | Leu | Gly |
| 1 | | | | 5 | | | | | 10 | | | | | 15 | |

| aca | tcc | gct | tcc | atc | tcc | tgc | agg | tct | agt | aag | agt | ctc | cga | cat | act | 96 |
| Thr | Ser | Ala | Ser | Ile | Ser | Cys | Arg | Ser | Ser | Lys | Ser | Leu | Arg | His | Thr |
| | | | 20 | | | | | 25 | | | | | 30 | | |

| aaa | ggc | atc | act | ttt | ttg | tat | tgg | tat | ctg | cag | aag | cca | ggc | cag | tct | 144 |
| Lys | Gly | Ile | Thr | Phe | Leu | Tyr | Trp | Tyr | Leu | Gln | Lys | Pro | Gly | Gln | Ser |
| | | | 35 | | | | | 40 | | | | | 45 | | |

| cct | cag | ctc | ctg | att | tat | cag | atg | tcc | aac | ctt | gcc | tca | gga | gtc | cca | 192 |
| Pro | Gln | Leu | Leu | Ile | Tyr | Gln | Met | Ser | Asn | Leu | Ala | Ser | Gly | Val | Pro |
| | | 50 | | | | | 55 | | | | | 60 | | | |

| gac | agg | ttc | agt | agc | agt | ggg | tca | gga | act | gat | ttc | aca | ctg | aga | atc | 240 |
| Asp | Arg | Phe | Ser | Ser | Ser | Gly | Ser | Gly | Thr | Asp | Phe | Thr | Leu | Arg | Ile |
| 65 | | | | | 70 | | | | | 75 | | | | | 80 |

| agc | aga | gtg | gag | gct | gag | gat | ttg | ggt | gtt | tat | tac | tgt | gct | caa | aat | 288 |
| Ser | Arg | Val | Glu | Ala | Glu | Asp | Leu | Gly | Val | Tyr | Tyr | Cys | Ala | Gln | Asn |
| | | | | 85 | | | | | 90 | | | | | 95 | |

| cta | gaa | ctt | ccg | ctc | acg | ttc | ggt | gct | ggg | acc | aag | ctg | gag | ctg | aaa | 336 |
| Leu | Glu | Leu | Pro | Leu | Thr | Phe | Gly | Ala | Gly | Thr | Lys | Leu | Glu | Leu | Lys |
| | | | 100 | | | | | 105 | | | | | 110 | | |

FIG. 2G mV$_H$ MAb13

| | | | | | | | | | | | | | | | | |
|---|---|---|---|---|---|---|---|---|---|---|---|---|---|---|---|---|
| gag | gtg | cag | ctg | gtg | gag | tct | ggg | gga | ggc | ttg | gtg | cag | cct | gga | ggg | 48 |
| Glu | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | ctg | aaa | ctc | tcc | tgt | gca | gcc | tct | gga | ttc | att | ttc | agt | agc | tat | 96 |
| Ser | Leu | Lys | Leu | Ser | Cys | Ala | Ala | Ser | Gly | Phe | Ile | Phe | Ser | Ser | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| ggc | atg | tct | tgg | gtt | cgc | cag | tct | cca | gac | agg | agg | ctg | gag | ttg | gtc | 144 |
| Gly | Met | Ser | Trp | Val | Arg | Gln | Ser | Pro | Asp | Arg | Arg | Leu | Glu | Leu | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gca | agt | att | aat | act | ttt | ggt | gat | aga | acc | tat | tat | cca | gac | agt | gtg | 192 |
| Ala | Ser | Ile | Asn | Thr | Phe | Gly | Asp | Arg | Thr | Tyr | Tyr | Pro | Asp | Ser | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| aag | ggc | cga | ttc | acc | atc | tcc | aga | gac | aat | gcc | aag | aac | acc | ctg | tac | 240 |
| Lys | Gly | Arg | Phe | Thr | Ile | Ser | Arg | Asp | Asn | Ala | Lys | Asn | Thr | Leu | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctg | caa | atg | acc | agt | ctg | aag | tct | gag | gac | aca | gcc | att | tat | tac | tgt | 288 |
| Leu | Gln | Met | Thr | Ser | Leu | Lys | Ser | Glu | Asp | Thr | Ala | Ile | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | aga | ggg | acc | gga | acc | tac | tgg | ggc | caa | ggc | acc | act | ctc | aca | gtc | 336 |
| Ala | Arg | Gly | Thr | Gly | Thr | Tyr | Trp | Gly | Gln | Gly | Thr | Thr | Leu | Thr | Val | |
| | | | 100 | | | | | 105 | | | | | 110 | | | |

| | | |
|---|---|---|
| tcc | tca | 342 |
| Ser | Ser | |

FIG. 2H mV$_L$ MAb13

| | | | | | | | | | | | | | | | | |
|---|---|---|---|---|---|---|---|---|---|---|---|---|---|---|---|---|
| gat | gtt | gtg | ctg | acc | cag | act | cca | ctc | act | ttg | tcg | gtt | acc | att | gga | 48 |
| Asp | Val | Val | Leu | Thr | Gln | Thr | Pro | Leu | Thr | Leu | Ser | Val | Thr | Ile | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| caa | cca | gcc | tcc | atc | tcc | tgc | aag | tca | agt | cag | agc | ctc | tta | gat | agt | 96 |
| Gln | Pro | Ala | Ser | Ile | Ser | Cys | Lys | Ser | Ser | Gln | Ser | Leu | Leu | Asp | Ser | |
| | | | 20 | | | | | 25 | | | | 30 | | | | |

| | | | | | | | | | | | | | | | | |
|---|---|---|---|---|---|---|---|---|---|---|---|---|---|---|---|---|
| gat | gga | aag | aca | tat | ttg | aat | tgg | ttg | tta | cag | agg | cca | ggc | cag | tct | 144 |
| Asp | Gly | Lys | Thr | Tyr | Leu | Asn | Trp | Leu | Leu | Gln | Arg | Pro | Gly | Gln | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| cca | aag | cgc | cta | atc | tat | ctg | gtg | tct | aaa | ctg | gac | tct | gga | gtc | cct | 192 |
| Pro | Lys | Arg | Leu | Ile | Tyr | Leu | Val | Ser | Lys | Leu | Asp | Ser | Gly | Val | Pro | |
| | 50 | | | | | | 55 | | | | | 60 | | | | |

| | | | | | | | | | | | | | | | | |
|---|---|---|---|---|---|---|---|---|---|---|---|---|---|---|---|---|
| gac | agg | ttc | act | ggc | agt | gga | tca | ggg | aca | gat | ttc | aca | ctg | aaa | atc | 240 |
| Asp | Arg | Phe | Thr | Gly | Ser | Gly | Ser | Gly | Thr | Asp | Phe | Thr | Leu | Lys | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agc | aga | gtg | gag | gct | gag | gat | ttg | gga | gtt | tat | tat | tgc | tgg | caa | ggt | 288 |
| Ser | Arg | Val | Glu | Ala | Glu | Asp | Leu | Gly | Val | Tyr | Tyr | Cys | Trp | Gln | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | cat | ttt | cct | cag | acg | ttc | ggt | gga | ggc | acc | aag | ctg | gaa | atc | aaa | 336 |
| Thr | His | Phe | Pro | Gln | Thr | Phe | Gly | Gly | Gly | Thr | Lys | Leu | Glu | Ile | Lys | |
| | | | 100 | | | | | 105 | | | | | 110 | | | |

FIG. 2I mV$_H$ MAb16

| | | | | | | | | | | | | | | | | |
|---|---|---|---|---|---|---|---|---|---|---|---|---|---|---|---|---|
| cag | gtc | caa | ctg | cag | cag | tct | ggg | gct | gaa | ctg | gtg | aag | cct | ggg | gct | 48 |
| Gln | Val | Gln | Leu | Gln | Gln | Ser | Gly | Ala | Glu | Leu | Val | Lys | Pro | Gly | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tca | gtg | aag | ttg | tcc | tgc | aag | gct | tct | ggc | tac | acc | ttc | acc | agc | tac | 96 |
| Ser | Val | Lys | Leu | Ser | Cys | Lys | Ala | Ser | Gly | Tyr | Thr | Phe | Thr | Ser | Tyr | |
| | | 20 | | | | | 25 | | | | | 30 | | | | |

| | | | | | | | | | | | | | | | | |
|---|---|---|---|---|---|---|---|---|---|---|---|---|---|---|---|---|
| tat | atg | tac | tgg | gtg | aag | cag | agg | cct | gga | caa | ggc | ctt | gag | tgg | att | 144 |
| Tyr | Met | Tyr | Trp | Val | Lys | Gln | Arg | Pro | Gly | Gln | Gly | Leu | Glu | Trp | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| gga | gag | att | aat | cct | agc | aat | ggt | ggt | act | aac | ttc | aat | gag | aag | ttc | 192 |
| Gly | Glu | Ile | Asn | Pro | Ser | Asn | Gly | Gly | Thr | Asn | Phe | Asn | Glu | Lys | Phe | |
| | 50 | | | | | 55 | | | | | 60 | | | | | |

| | | | | | | | | | | | | | | | | |
|---|---|---|---|---|---|---|---|---|---|---|---|---|---|---|---|---|
| aag | agc | aag | gcc | aca | ctg | act | gta | gac | aaa | tcc | tcc | agc | aca | gca | tac | 240 |
| Lys | Ser | Lys | Ala | Thr | Leu | Thr | Val | Asp | Lys | Ser | Ser | Ser | Thr | Ala | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atg | caa | ctc | agc | agc | ctg | aca | tct | gag | gac | tct | gcg | gtc | tat | tac | tgt | 288 |
| Met | Gln | Leu | Ser | Ser | Leu | Thr | Ser | Glu | Asp | Ser | Ala | Val | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | aga | ggc | ggt | tac | tac | ccc | ttt | gac | tac | tgg | ggc | caa | ggc | acc | act | 336 |
| Thr | Arg | Gly | Gly | Tyr | Tyr | Pro | Phe | Asp | Tyr | Trp | Gly | Gln | Gly | Thr | Thr | |
| | | | | 100 | | | | | 105 | | | | | 110 | | |

| | | | | |
|---|---|---|---|---|
| ctc | aca | gtc | tcc | tca | 351 |
| Leu | Thr | Val | Ser | Ser | |
| | | 115 | | | |

FIG. 2J mV$_L$ MAb16

| | | | | | | | | | | | | | | | | |
|---|---|---|---|---|---|---|---|---|---|---|---|---|---|---|---|---|
| gat | gtt | gtg | atg | acc | cag | act | cca | ctc | act | ttg | tcg | gtt | acc | att | ggg | 48 |
| Asp | Val | Val | Met | Thr | Gln | Thr | Pro | Leu | Thr | Leu | Ser | Val | Thr | Ile | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cgc | cca | gcc | tcc | atc | tct | tgc | aag | tca | agt | cag | agc | ctc | tta | gac | agt | 96 |
| Arg | Pro | Ala | Ser | Ile | Ser | Cys | Lys | Ser | Ser | Gln | Ser | Leu | Leu | Asp | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| gat | gga | aag | aca | tat | ttg | tat | tgg | ttg | tta | cag | agg | cca | ggc | cag | tct | 144 |
| Asp | Gly | Lys | Thr | Tyr | Leu | Tyr | Trp | Leu | Leu | Gln | Arg | Pro | Gly | Gln | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| cca | aag | cgc | cta | atc | tat | ctg | gtg | tct | gag | ctg | gac | tct | gga | gtc | cct | 192 |
| Pro | Lys | Arg | Leu | Ile | Tyr | Leu | Val | Ser | Glu | Leu | Asp | Ser | Gly | Val | Pro | |
| | 50 | | | | | | 55 | | | | | 60 | | | | |

| | | | | | | | | | | | | | | | | |
|---|---|---|---|---|---|---|---|---|---|---|---|---|---|---|---|---|
| gac | agg | atc | act | ggc | agt | ggg | tcg | ggg | aca | gat | ttc | aca | ctg | aag | atc | 240 |
| Asp | Arg | Ile | Thr | Gly | Ser | Gly | Ser | Gly | Thr | Asp | Phe | Thr | Leu | Lys | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agc | aga | gtg | gag | gct | gag | gat | ttg | gga | gtt | tat | tat | tgc | tgg | caa | gga | 288 |
| Ser | Arg | Val | Glu | Ala | Glu | Asp | Leu | Gly | Val | Tyr | Tyr | Cys | Trp | Gln | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | cat | tct | ccg | tac | acg | ttc | gga | ggg | ggg | acc | aag | ctg | gaa | ata | aaa | 336 |
| Thr | His | Ser | Pro | Tyr | Thr | Phe | Gly | Gly | Gly | Thr | Lys | Leu | Glu | Ile | Lys | |
| | | | 100 | | | | | 105 | | | | | 110 | | | |

FIG. 2K mV_H MAb19

```
gat gtg cag ctt cag gag tcg gga cct ggc ctg gtg aaa cct tct cag    48
Asp Val Gln Leu Gln Glu Ser Gly Pro Gly Leu Val Lys Pro Ser Gln
1               5                   10                  15 tct ctg tcc ctc aca tgc act gtc act ggc tac tca atc acc agt gat    96
Ser Leu Ser Leu Thr Cys Thr Val Thr Gly Tyr Ser Ile Thr Ser Asp
                20                  25                  30 tat gcc tgg aat tgg atc cgg cag ttt cca gga aac aaa ctg gag tgg   144
Tyr Ala Trp Asn Trp Ile Arg Gln Phe Pro Gly Asn Lys Leu Glu Trp
        35                  40                  45 atg ggc tac ata agc ttc agt ggt tac act agt tac aac cca tct ctc   192
Met Gly Tyr Ile Ser Phe Ser Gly Tyr Thr Ser Tyr Asn Pro Ser Leu
        50                  55                  60 aaa agt cga atc tct gtc act cgg gac aca tcc agg aac caa ttc ttc   240
Lys Ser Arg Ile Ser Val Thr Arg Asp Thr Ser Arg Asn Gln Phe Phe
65                  70                  75                  80 ctc cag ttg act tct gtg act act gag gac aca gcc aca tat tac tgt   288
Leu Gln Leu Thr Ser Val Thr Thr Glu Asp Thr Ala Thr Tyr Tyr Cys
                85                  90                  95 gca aga gag gtc aac tat ggg gac tcc tac cac ttt gac tac tgg ggc   336
Ala Arg Glu Val Asn Tyr Gly Asp Ser Tyr His Phe Asp Tyr Trp Gly
                100                 105                 110 caa ggc acc att gtc aca gtc tcc tca                               363
Gln Gly Thr Ile Val Thr Val Ser Ser
        115                 120
```

FIG. 2L mV$_L$ MAb19

```
caa ctt gcg ctc act cag tca tct tca gcc tct ttc tcc ctg gga gcc   48
Gln Leu Ala Leu Thr Gln Ser Ser Ser Ala Ser Phe Ser Leu Gly Ala
1               5                   10                  15 tca gca aaa cta acg tgc act ttg agt agt caa cac aga acg tac acc   96
Ser Ala Lys Leu Thr Cys Thr Leu Ser Ser Gln His Arg Thr Tyr Thr
            20                  25                  30 att gaa tgg tat cag caa cag tca ctc aag cct cct aag tat gtg atg  144
Ile Glu Trp Tyr Gln Gln Gln Ser Leu Lys Pro Pro Lys Tyr Val Met
        35                  40                  45 gag gtt aag aaa gat gga agc cac agc aca ggt cat ggg att cct gat  192
Glu Val Lys Lys Asp Gly Ser His Ser Thr Gly His Gly Ile Pro Asp
    50                  55                  60 cgc ttc tct gga tcc agt tct ggt gct gat cgc tac ctc agc att tcc  240
Arg Phe Ser Gly Ser Ser Ser Gly Ala Asp Arg Tyr Leu Ser Ile Ser
65                  70                  75                  80 aac atc cag cct gaa gat gaa gca ata tac atc tgt ggt gtg ggt gat  288
Asn Ile Gln Pro Glu Asp Glu Ala Ile Tyr Ile Cys Gly Val Gly Asp
            85                  90                  95 gca att aag gga caa tct gtg ttt gtt ttc ggc ggt ggc acc aag gtc  336
Ala Ile Lys Gly Gln Ser Val Phe Val Phe Gly Gly Gly Thr Lys Val
            100                 105                 110 act gtc cta                                                       345
Thr Val Leu
        115
```

FIG. 3A hV$_H$ MAb3

Gln Val Gln Leu Val Gln Ser Gly Ala Glu Val Lys Lys Pro Gly Ala
1               5                       10                      15

Ser Val Lys Val Ser Cys Lys Ala Ser <u>Gly Tyr Ile Phe Thr Ser Tyr</u>
                20                  25                      30

<u>Trp</u> Val His Trp Val Arg Gln Ala Pro Gly Gln Arg Leu Glu Trp Met
            35                      40                      45

Gly Gly <u>Phe Tyr Pro Gly Asn Ser Asp Ser</u> Arg Tyr Ser Gln Lys Phe
        50                  55                      60

Gln Gly Arg Val Thr Ile Thr Arg Asp Thr Ser Ala Ser Thr Ala Tyr
65                      70                      75                      80

Met Glu Leu Ser Ser Leu Arg Ser Glu Asp Thr Ala Val Tyr Tyr Cys
                85                      90                      95

<u>Thr Arg Arg Asp Ser Pro Gln Tyr</u> Trp Gly Gln Gly Thr Leu Val Thr
            100                     105                     110

Val Ser Ser
        115

FIG. 3B hV$_L$ MAb3

Asp Val Val Met Thr Gln Ser Pro Leu Ser Leu Pro Val Thr Leu Gly
1           5                   10                  15

Gln Pro Ala Ser Ile Ser Cys Arg Ser Ser <u>Gln Ser Ile Val His Ser</u>
            20              25                  30

<u>Asn Gly Asn Thr Tyr</u> Leu Glu Trp Phe Gln Gln Arg Pro Gly Gln Ser
            35              40                  45

Pro Arg Arg Leu Ile Tyr <u>Lys Val Ser</u> Asn Arg Phe Ser Gly Val Pro
        50              55                  60

Asp Arg Phe Ser Gly Ser Gly Ser Gly Thr Asp Phe Thr Leu Lys Ile
65              70              75                  80

Ser Arg Val Glu Ala Glu Asp Val Gly Val Tyr Tyr Cys <u>Phe Gln Gly</u>
            85                  90                  95

<u>Ser His Val Pro Phe Thr</u> Phe Gly Gly Gly Thr Lys Val Glu Ile Lys
            100                 105                 110

FIG. 3C hV$_H$ MAb4

Gln Val Gln Leu Val Gln Ser Gly Ala Glu Val Lys Lys Pro Gly Ala
1               5                   10                  15

Ser Val Lys Val Ser Cys Lys Ala Ser <u>Gly Tyr Thr Phe Ser Ser Ser</u>
                20                  25                  30

<u>Trp</u> Met His Trp Val Arg Gln Ala Pro Gly Gln Gly Leu Glu Trp Met
        35                  40                  45

Gly Ile <u>Phe Leu Pro Gly Ser Gly Ser Thr</u> Asp Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

<u>Ala Thr Asp Gly Asn Tyr Asp Trp Phe Ala Tyr</u> Trp Gly Gln Gly Thr
                100                 105                 110

Leu Val Thr Val Ser Ser
        115

FIG. 3D hV$_L$ MAb4

Asp Ile Val Met Thr Gln Thr Pro Leu Ser Leu Ser Val Thr Pro Gly
1               5                   10                  15

Gln Pro Ala Ser Ile Ser Cys Lys Ser Ser <u>Gln Ser Leu Val His Ser</u>
            20                  25              30

<u>Ser Gly Val Thr Tyr</u> Leu Tyr Trp Tyr Leu Gln Lys Pro Gly Gln Ser
            35              40                  45

Pro Gln Leu Leu Ile Tyr <u>Lys Val Ser</u> Asn Arg Phe Ser Gly Val Pro
        50              55                  60

Asp Arg Phe Ser Gly Ser Gly Ser Gly Thr Asp Phe Thr Leu Lys Ile
65              70              75                      80

Ser Arg Val Glu Ala Glu Asp Val Gly Val Tyr Tyr Cys <u>Ser Gln Ser</u>
            85                  90                      95

<u>Thr His Val Pro Pro Thr</u> Phe Gly Gln Gly Thr Lys Leu Glu Ile Lys
                100             105                 110

FIG. 3E hV$_H$ MAb8(a)

Glu Val Gln Leu Val Glu Ser Gly Gly Gly Leu Val Lys Pro Gly Gly
1               5                   10                  15

Ser Leu Arg Leu Ser Cys Ala Ala Ser <u>Gly Phe Thr Phe Thr Thr Tyr</u>
            20                  25                  30

<u>Ala</u> Met Ser Trp Val Arg Gln Ala Pro Gly Lys Gly Leu Glu Trp Val
        35                  40                  45

Ser Ser <u>Ile Ser Ser Gly Gly Thr Tyr Thr</u> Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

<u>Ala Thr Gln Gly Asn Tyr Ser Leu Asp Phe</u> Trp Gly Gln Gly Thr Thr
            100                 105                 110

Val Thr Val Ser Ser
        115

FIG. 3F hV$_L$ MAb8(a)

Asp Ile Val Met Thr Gln Ser Pro Leu Ser Leu Pro Val Thr Pro Gly
1               5                   10                  15

Glu Pro Ala Ser Ile Ser Cys Arg Ser Ser <u>Lys Ser Leu Arg His Thr</u>
                20                  25                  30

<u>Lys Gly Ile Thr Phe</u> Leu Tyr Trp Tyr Leu Gln Lys Pro Gly Gln Ser
            35                  40                  45

Pro Gln Leu Leu Ile Tyr <u>Gln Met Ser</u> Asn Arg Ala Ser Gly Val Pro
        50              55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys <u>Ala Gln Asn</u>
                85                  90                  95

<u>Leu Glu Leu Pro Leu Thr</u> Phe Gly Gly Gly Thr Lys Val Glu Ile Lys
            100                 105                 110

FIG. 3G hV_H MAb8(b)

Glu Val Gln Leu Val Glu Ser Gly Gly Gly Leu Val Lys Pro Gly Gly
1               5                   10                  15

Ser Leu Arg Leu Ser Cys Ala Ala Ser <u>Gly Phe Thr Phe Thr Thr Tyr</u>
        20                  25                  30

<u>Ala</u> Met Asn Trp Val Arg Gln Ala Pro Gly Lys Gly Leu Glu Trp Val
        35                  40                  45

Ser Ser <u>Ile Ser Ser Gly Gly Thr Tyr Thr</u> Tyr Tyr Ala Asp Ser Val
    50              55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
            85                  90                  95

<u>Ala Thr Gln Gly Asn Tyr Ser Leu Asp Phe</u> Trp Gly Gln Gly Thr Thr
            100                 105                 110

Val Thr Val Ser Ser
        115

FIG. 3H hV$_L$ MAb8(b)

Asp Ile Val Met Thr Gln Ser Pro Leu Ser Leu Pro Val Thr Pro Gly
1              5                   10                  15

Glu Pro Ala Ser Ile Ser Cys Arg Ser Ser <u>Lys Ser Leu Arg His Thr</u>
            20                  25                  30

<u>Lys Gly Ile Thr Phe</u> Leu Asp Trp Tyr Leu Gln Lys Pro Gly Gln Ser
            35                  40                  45

Pro Gln Leu Leu Ile Tyr <u>Gln Met Ser</u> Asn Arg Ala Ser Gly Val Pro
        50              55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys <u>Ala Gln Asn</u>
            85                  90                  95

<u>Leu Glu Leu Pro Leu Thr</u> Phe Gly Gly Gly Thr Lys Val Glu Ile Lys
            100                 105                 110

FIG. 3I hV$_H$ MAb8(c)

Glu Val Gln Leu Val Glu Ser Gly Gly Gly Leu Val Lys Pro Gly Gly
1               5                   10                  15

Ser Leu Arg Leu Ser Cys Ala Ala Ser <u>Gly Phe Thr Phe Thr Thr Tyr</u>
            20                  25                  30

<u>Ala</u> Met Ser Trp Val Arg Gln Ala Pro Gly Lys Gly Leu Glu Trp Val
            35                  40                  45

Ser Thr <u>Ile Ser Ser Gly Gly Thr Tyr Thr</u> Tyr Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

<u>Ala Thr Gln Gly Asn Tyr Ser Leu Asp Phe</u> Trp Gly Gln Gly Thr Thr
                    100                 105                 110

Val Thr Val Ser Ser
        115

FIG. 3J hV_L MAb8(c)

Asp Ile Val Met Thr Gln Ser Pro Leu Ser Leu Pro Val Thr Pro Gly
1                   5                        10                       15

Glu Pro Ala Ser Ile Ser Cys Arg Ser Ser Lys Ser Leu Arg His Thr
            20                      25                    30

Lys Gly Ile Thr Phe Leu Tyr Trp Tyr Leu Gln Lys Pro Gly Gln Ser
            35                      40                    45

Pro Gln Leu Leu Ile Tyr Gln Met Ser Asn Arg Ala Ser Gly Val Pro
            50                      55                    60

Asp Arg Phe Ser Gly Ser Gly Ser Gly Thr Asp Phe Thr Leu Lys Ile
65                      70                      75                    80

Ser Arg Val Glu Ala Glu Asp Val Gly Val Tyr Tyr Cys Ala Gln Asn
                85                      90                    95

Leu Glu Leu Pro Leu Thr Phe Gly Gly Gly Thr Lys Val Glu Ile Lys
            100                     105                   110

FIG. 3K hV$_H$ MAb13(a)

Glu Val Gln Leu Val Glu Ser Gly Gly Gly Leu Val Gln Pro Gly Gly
1               5                       10                  15

Ser Leu Arg Leu Ser Cys Ala Ala Ser <u>Gly Phe Ile Phe Ser Ser Tyr</u>
            20                  25                  30

<u>Gly</u> Met Ser Trp Val Arg Gln Ala Pro Gly Lys Gly Leu Glu Trp Val
        35                      40                  45

Ala Asn <u>Ile Asn Thr Phe Gly Asp Arg Thr</u> Tyr Tyr Val Asp Ser Val
    50              55                      60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                      90                  95

<u>Ala Arg Gly Thr Gly Thr Tyr</u> Trp Gly Gln Gly Thr Leu Val Thr Val
        100                     105                 110

Ser Ser

FIG. 3L hV_L MAb13(a)

Asp Val Val Met Thr Gln Ser Pro Leu Ser Leu Pro Val Thr Leu Gly
1             5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
        50              55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Trp Gln Gly
            85                  90                  95

Thr His Phe Pro Gln Thr Phe Gly Gly Gly Thr Lys Val Glu Ile Lys
            100                 105                 110

FIG. 3M hV$_H$ MAb13(b)

| | | | | | | | | | | | | | | |
|---|---|---|---|---|---|---|---|---|---|---|---|---|---|---|
|Glu|Val|Gln|Leu|Val|Glu|Ser|Gly|Gly|Leu|Val|Gln|Pro|Gly|Gly|
|1| | | |5| | | |10| | | | |15| |

Ser Leu Arg Leu Ser Cys Ala Ala Ser <u>Gly Phe Ile Phe Ser Ser Tyr</u>
　　　　　20　　　　　　　　25　　　　　　　　30

<u>Gly</u> Met Ser Trp Val Arg Gln Ala Pro Gly Lys Gly Leu Glu Trp Val
　　　　　35　　　　　　　　40　　　　　　　　45

Ala Ser <u>Ile Asn Thr Phe Gly Asp Arg Thr</u> Tyr Tyr Val Asp Ser Val
　　50　　　　　　　　55　　　　　　　　60

Lys Gly Arg Phe Thr Ile Ser Arg Asp Asn Ala Lys Asn Ser Leu Tyr
65　　　　　　　　70　　　　　　　　75　　　　　　　　80

Leu Gln Met Asn Ser Leu Arg Ala Glu Asp Thr Ala Val Tyr Tyr Cys
　　　　　　　　85　　　　　　　　90　　　　　　　　95

<u>Ala Arg Gly Thr Gly Thr Tyr</u> Trp Gly Gln Gly Thr Leu Val Thr Val
　　　　　　　100　　　　　　　105　　　　　　　110

Ser Ser

FIG. 3N hV$_L$ MAb13(b)

Asp Val Val Met Thr Gln Ser Pro Leu Ser Leu Pro Val Thr Leu Gly
1         5                       10                    15

Gln Pro Ala Ser Ile Ser Cys Arg Ser Ser <u>Gln Ser Leu Leu Asp Ser</u>
              20                  25                    30

<u>Asp Gly Lys Thr Tyr</u> Leu Asn Trp Phe Gln Gln Arg Pro Gly Gln Ser
            35                  40                    45

Pro Arg Arg Leu Ile Tyr <u>Leu Val Ser</u> Lys Arg Asp Ser Gly Val Pro
          50                  55                    60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys <u>Trp Gln Gly</u>
              85                  90                    95

<u>Thr His Phe Pro Gln Thr</u> Phe Gly Gly Gly Thr Lys Val Glu Ile Lys
              100                 105                   110

FIG. 3O hV_H MAb16(a)

Gln Val Gln Leu Val Gln Ser Gly Ala Glu Val Lys Lys Pro Gly Ala
1               5                   10                  15

Ser Val Lys Val Ser Cys Lys Ala Ser <u>Gly Tyr Thr Phe Thr Ser Tyr</u>
                20              25                  30

<u>Tyr</u> Met Tyr Trp Val Arg Gln Ala Pro Gly Gln Gly Leu Glu Trp Met
        35                  40                  45

Gly Ile <u>Ile Asn Pro Ser Asn Gly Gly Thr</u> Ser Tyr Ala Gln Lys Phe
        50              55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

<u>Thr Arg Gly Gly Tyr Tyr Pro Phe Asp Tyr</u> Trp Gly Gln Gly Thr Thr
            100                 105                 110

Val Thr Val Ser Ser
        115

FIG. 3P hV$_L$ MAb16(a)

Asp Val Val Met Thr Gln Ser Pro Leu Ser Leu Pro Val Thr Leu Gly
1              5                   10                  15

Gln Pro Ala Ser Ile Ser Cys Arg Ser Ser <u>Gln Ser Leu Leu Asp Ser</u>
                20              25                  30

<u>Asp Gly Lys Thr Tyr</u> Leu Tyr Trp Phe Gln Gln Arg Pro Gly Gln Ser
            35                  40                  45

Pro Arg Arg Leu Ile Tyr <u>Leu Val Ser</u> Asn Arg Asp Ser Gly Val Pro
        50              55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys <u>Trp Gln Gly</u>
                85                  90                  95

<u>Thr His Ser Pro Tyr Thr</u> Phe Gly Gln Gly Thr Lys Leu Glu Ile Lys
            100                 105                 110

FIG. 3Q hV$_H$ MAb16(b)

Gln Val Gln Leu Val Gln Ser Gly Ala Glu Val Lys Lys Pro Gly Ala
1             5                   10                  15

Ser Val Lys Val Ser Cys Lys Ala Ser <u>Gly Tyr Thr Phe Thr Ser Tyr</u>
            20                  25                  30

<u>Tyr</u> Met His Trp Val Arg Gln Ala Pro Gly Gln Gly Leu Glu Trp Met
        35                  40                  45

Gly Ile <u>Ile Asn Pro Ser Asn Gly Gly Thr</u> Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

<u>Thr Arg Gly Gly Tyr Tyr Pro Phe Asp Tyr</u> Trp Gly Gln Gly Thr Thr
            100                 105                 110

Val Thr Val Ser Ser
        115

FIG. 3R hV$_L$ MAb16(b)

Asp Val Val Met Thr Gln Ser Pro Leu Ser Leu Pro Val Thr Leu Gly
1           5                   10                  15

Gln Pro Ala Ser Ile Ser Cys Arg Ser Ser <u>Gln Ser Leu Leu Asp Ser</u>
                20                  25              30

<u>Asp Gly Lys Thr Tyr</u> Leu Asn Trp Phe Gln Gln Arg Pro Gly Gln Ser
        35                  40                  45

Pro Arg Arg Leu Ile Tyr <u>Leu Val Ser</u> Asn Arg Asp Ser Gly Val Pro
        50              55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Val Tyr Tyr Cys <u>Trp Gln Gly</u>
                85                  90                  95

<u>Thr His Ser Pro Tyr Thr</u> Phe Gly Gln Gly Thr Lys Leu Glu Ile Lys
            100                 105                 110

FIG. 3S hV$_H$ MAb16(c)

Gln Val Gln Leu Val Gln Ser Gly Ala Glu Val Lys Lys Pro Gly Ala
1              5                    10                  15

Ser Val Lys Val Ser Cys Lys Ala Ser <u>Gly Tyr Thr Phe Thr Ser Tyr</u>
              20                  25                  30

<u>Tyr</u> Met Tyr Trp Val Arg Gln Ala Pro Gly Gln Gly Leu Glu Trp Met
         35                  40                  45

Gly Glu <u>Ile Asn Pro Ser Asn Gly Gly Thr</u> Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
              85                  90                  95

<u>Thr Arg Gly Gly Tyr Tyr Pro Phe Asp Tyr</u> Trp Gly Gln Gly Thr Thr
              100                 105                 110

Val Thr Val Ser Ser
              115

FIG. 3T hV$_L$ MAb16(c)

Asp Val Val Met Thr Gln Ser Pro Leu Ser Leu Pro Val Thr Leu Gly
1              5                    10                  15

Gln Pro Ala Ser Ile Ser Cys Arg Ser Ser <u>Gln Ser Leu Leu Asp Ser</u>
              20                  25                  30

<u>Asp Gly Lys Thr Tyr</u> Leu Tyr Trp Phe Gln Gln Arg Pro Gly Gln Ser
         35                      40                  45

Pro Arg Arg Leu Ile Tyr <u>Leu Val Ser</u> Glu Arg Asp Ser Gly Val Pro
    50                      55              60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys <u>Trp Gln Gly</u>
            85                  90                  95

<u>Thr His Ser Pro Tyr Thr</u> Phe Gly Gln Gly Thr Lys Leu Glu Ile Lys
            100                 105                 110

FIG. 3U hV$_H$ MAb19(a)

Gln Val Gln Leu Gln Glu Ser Gly Pro Gly Leu Val Lys Pro Ser Gln
1               5                   10                  15

Thr Leu Ser Leu Thr Cys Thr Val Ser <u>Gly Tyr Ser Ile Thr Ser Asp</u>
            20                  25                  30

<u>Tyr Ala</u> Trp Asn Trp Ile Arg Gln His Pro Gly Lys Gly Leu Glu Trp
        35                  40                  45

Ile Gly Tyr <u>Ile Ser Phe Ser Gly Tyr Thr</u> Tyr Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

<u>Ala Arg Glu Val Asn Tyr Gly Asp Ser Tyr His Phe Asp Tyr</u> Trp Gly
            100                 105                 110

Gln Gly Thr Leu Val Thr Val Ser Ser
        115                 120

FIG. 3V hV$_L$ MAb19(a)

Gln Leu Val Leu Thr Gln Ser Pro Ser Ala Ser Ala Ser Leu Gly Ala
1               5                   10                  15

Ser Val Lys Leu Thr Cys Thr Leu Ser <u>Ser Gln His Arg Thr Tyr Thr</u>
                20              25                  30

Ile Glu Trp His Gln Gln Pro Glu Lys Gly Pro Arg Tyr Leu Met
            35                  40                  45

Lys <u>Val Lys Lys Asp Gly Ser His</u> Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys <u>Gly Val Gly Asp</u>
                85                  90                  95

<u>Ala Ile Lys Gly Gln Ser Val Phe Val</u> Phe Gly Gly Gly Thr Lys Val
                100                 105                 110

Glu Ile Lys
        115

FIG. 3W hV$_H$ MAb19(b)

Gln Val Gln Leu Gln Glu Ser Gly Pro Gly Leu Val Lys Pro Ser Gln
1               5                   10                  15

Thr Leu Ser Leu Thr Cys Thr Val Ser <u>Gly Tyr Ser Ile Thr Ser Asp</u>
            20                  25                  30

<u>Tyr Ala</u> Trp Ser Trp Ile Arg Gln His Pro Gly Lys Gly Leu Glu Trp
        35                  40                  45

Ile Gly Tyr <u>Ile Ser Phe Ser Gly Tyr Thr</u> Tyr Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

<u>Ala Arg Glu Val Asn Tyr Gly Asp Ser Tyr His Phe Asp Tyr</u> Trp Gly
            100                 105                 110

Gln Gly Thr Leu Val Thr Val Ser Ser
        115                 120

FIG. 3X hV$_L$ MAb19(b)

Gln Leu Val Leu Thr Gln Ser Pro Ser Ala Ser Ala Ser Leu Gly Ala
1              5                   10                  15

Ser Val Lys Leu Thr Cys Thr Leu Ser Ser Gln His Arg Thr Tyr Thr
              20                  25                  30

Ile Ala Trp His Gln Gln Pro Glu Lys Gly Pro Arg Tyr Leu Met
         35                  40                  45

Lys Val Lys Lys Asp Gly Ser His Ser Lys Gly Asp Gly Ile Pro Asp
         50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                  85                  90                  95

Ala Ile Lys Gly Gln Ser Val Phe Val Phe Gly Gly Gly Thr Lys Val
              100                 105                 110

Glu Ile Lys
         115

FIG. 3Y hV<sub>H</sub> MAb19(c)

Gln Val Gln Leu Gln Glu Ser Gly Pro Gly Leu Val Lys Pro Ser Gln
1               5                   10                  15

Thr Leu Ser Leu Thr Cys Thr Val Ser <u>Gly Tyr Ser Ile Thr Ser Asp</u>
            20                  25                  30

<u>Tyr Ala</u> Trp Asn Trp Ile Arg Gln His Pro Gly Lys Gly Leu Glu Trp
        35                  40                  45

Ile Gly Tyr <u>Ile Ser Phe Ser Gly Tyr Thr</u> Ser Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

<u>Ala Arg Glu Val Asn Tyr Gly Asp Ser Tyr His Phe Asp Tyr</u> Trp Gly
            100                 105                 110

Gln Gly Thr Leu Val Thr Val Ser Ser
        115                 120

FIG. 3Z hV$_L$ MAb19(c)

Gln Leu Val Leu Thr Gln Ser Pro Ser Ala Ser Ala Ser Leu Gly Ala
1               5                   10                  15

Ser Val Lys Leu Thr Cys Thr Leu Ser <u>Ser Gln His Arg Thr Tyr Thr</u>
                20              25                  30

Ile Glu Trp His Gln Gln Pro Glu Lys Gly Pro Arg Tyr Leu Met
            35                  40                  45

Glu <u>Val Lys Lys Asp Gly Ser His</u> Ser Lys Gly Asp Gly Ile Pro Asp
    50                  55                  60

Arg Phe Ser Gly Ser Ser Ser Gly Ala Glu Arg Tyr Leu Thr Ile Ser
65              70                  75                  80

Ser Leu Gln Ser Glu Asp Glu Ala Asp Tyr Tyr Cys <u>Gly Val Gly Asp</u>
                85                  90                  95

<u>Ala Ile Lys Gly Gln Ser Val Phe Val</u> Phe Gly Gly Gly Thr Lys Val
                100             105                 110

Glu Ile Lys
        115

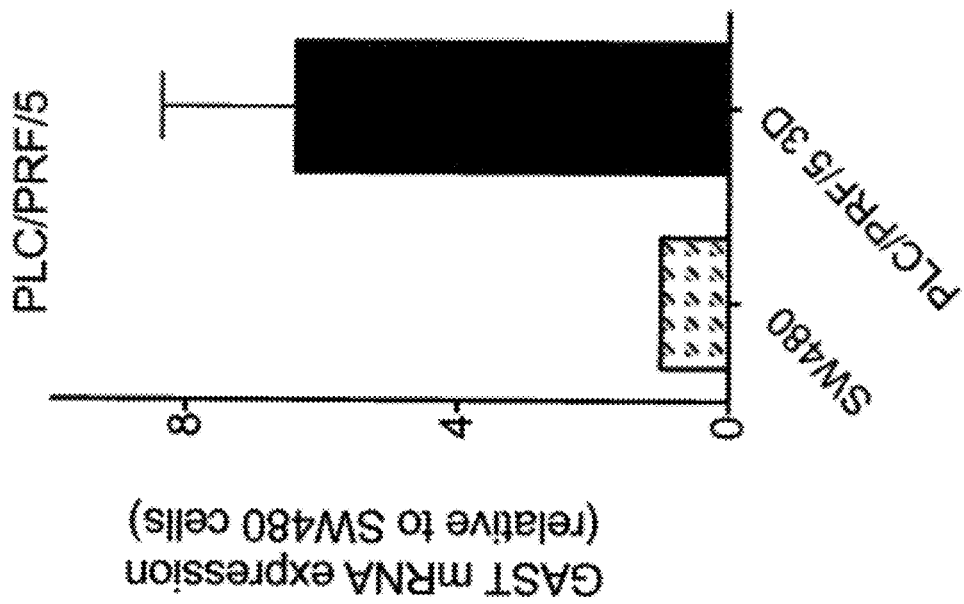

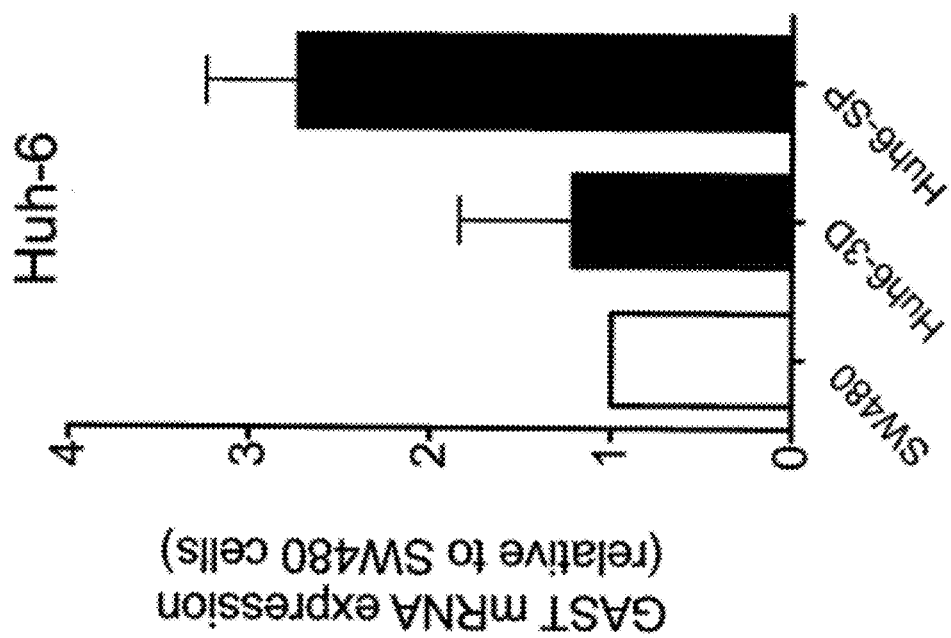

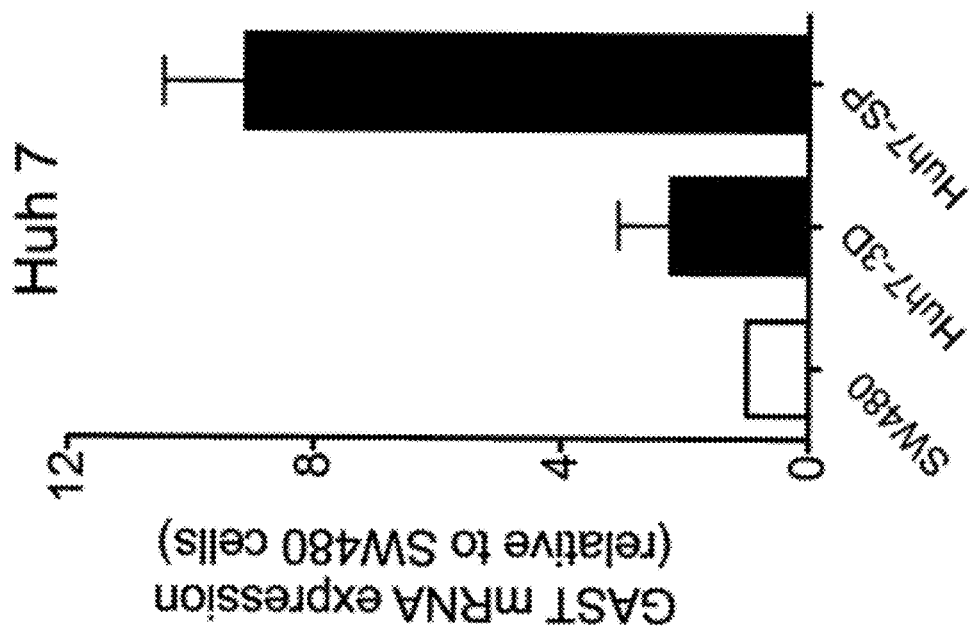

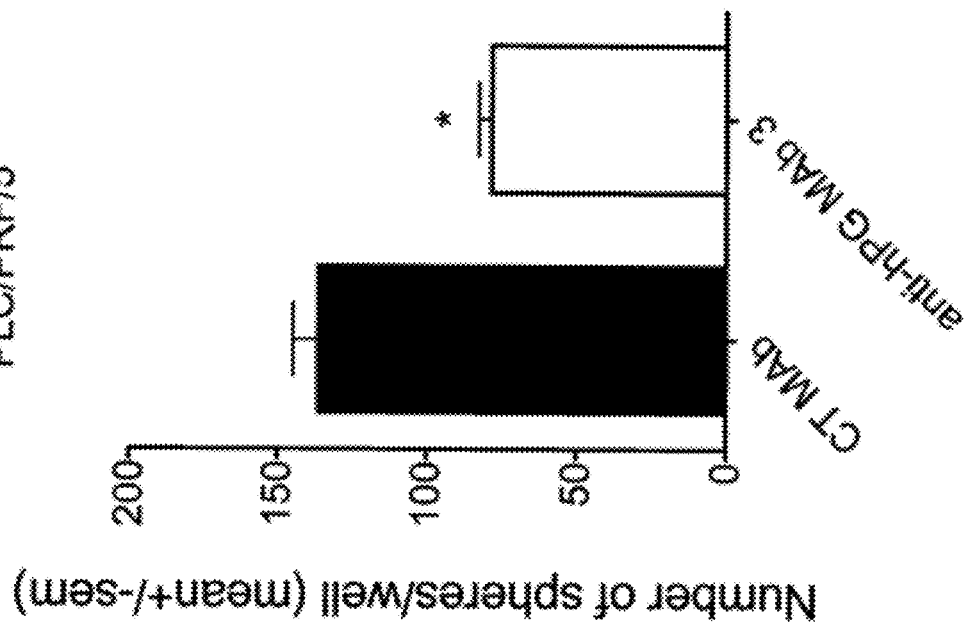

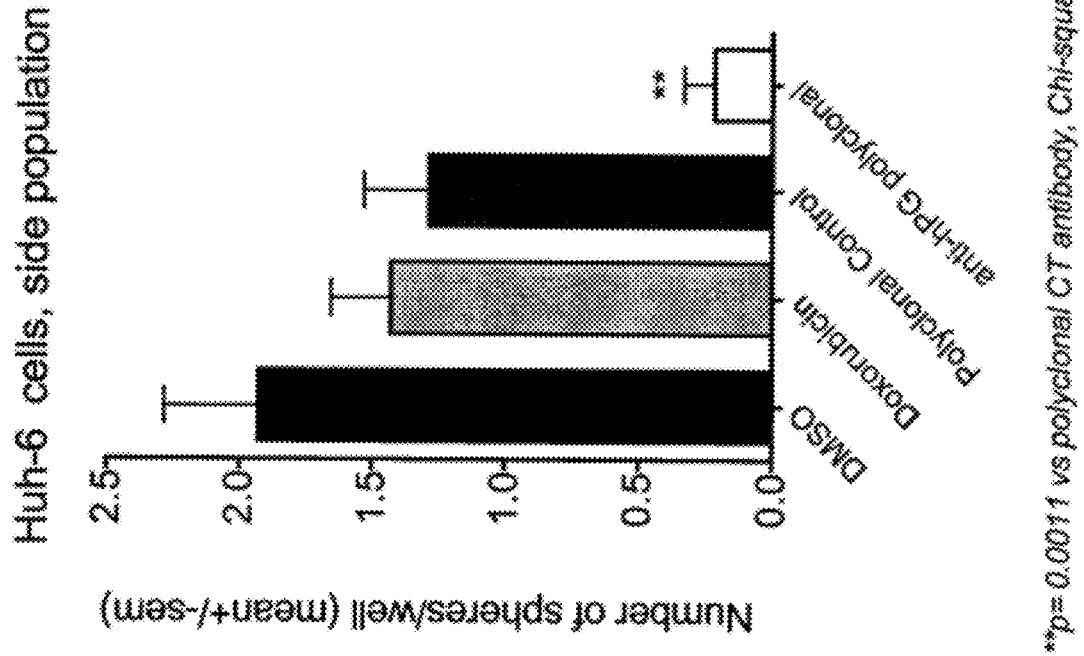

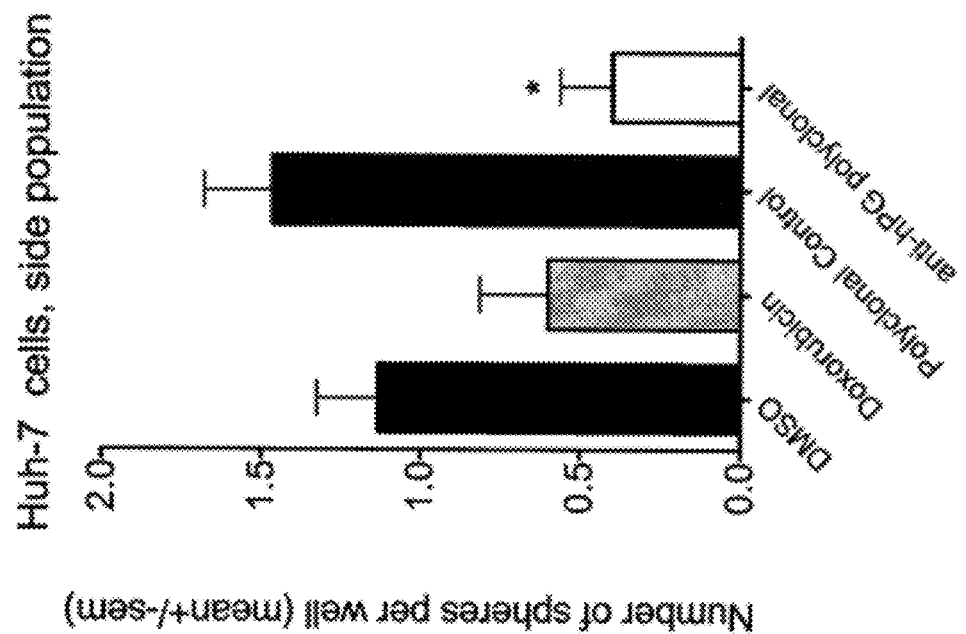

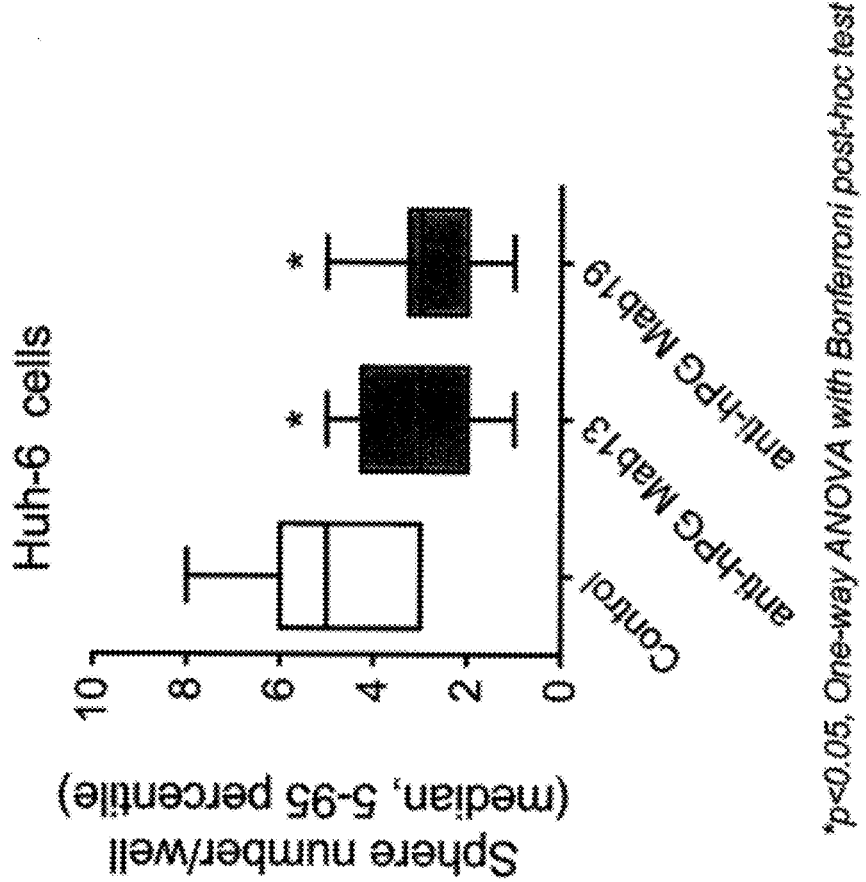

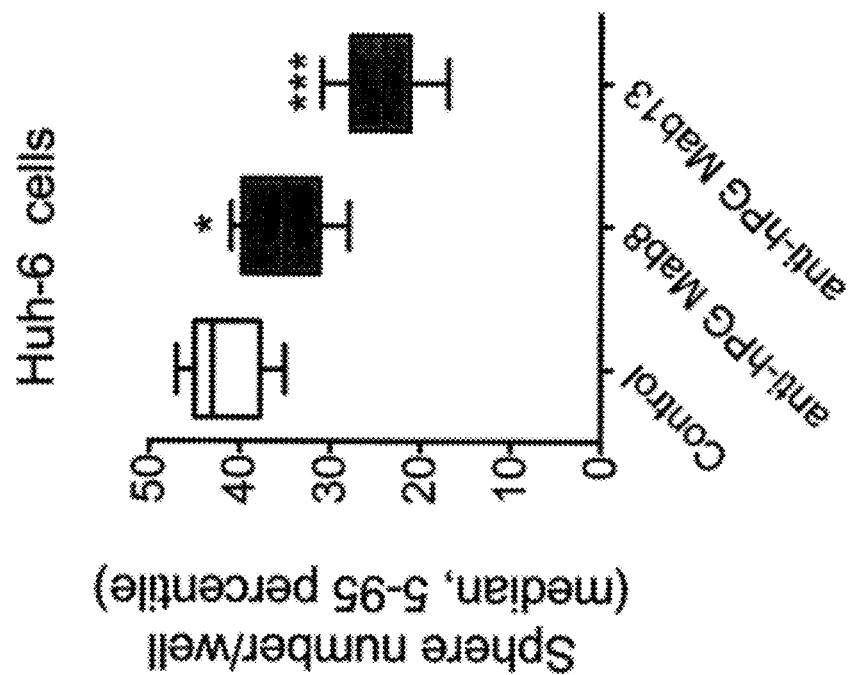

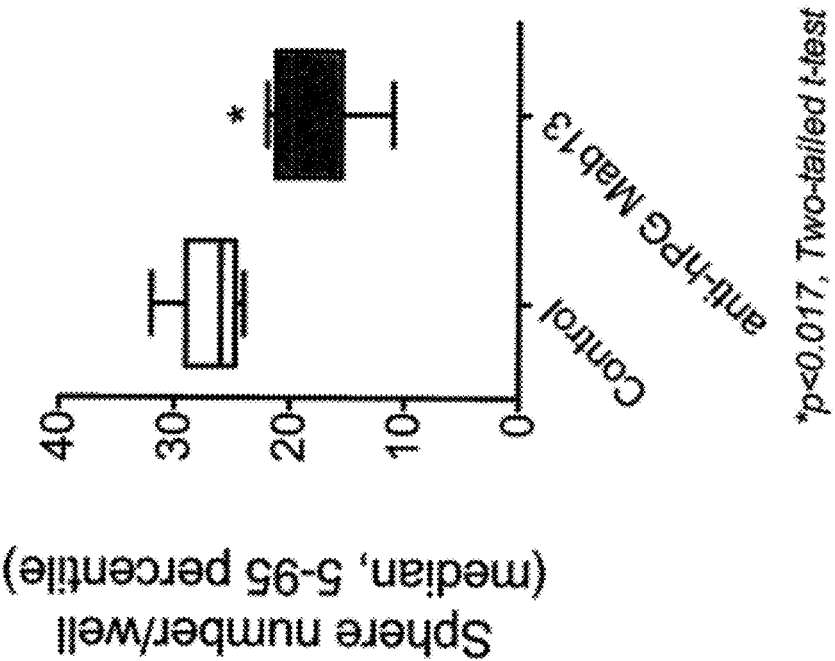

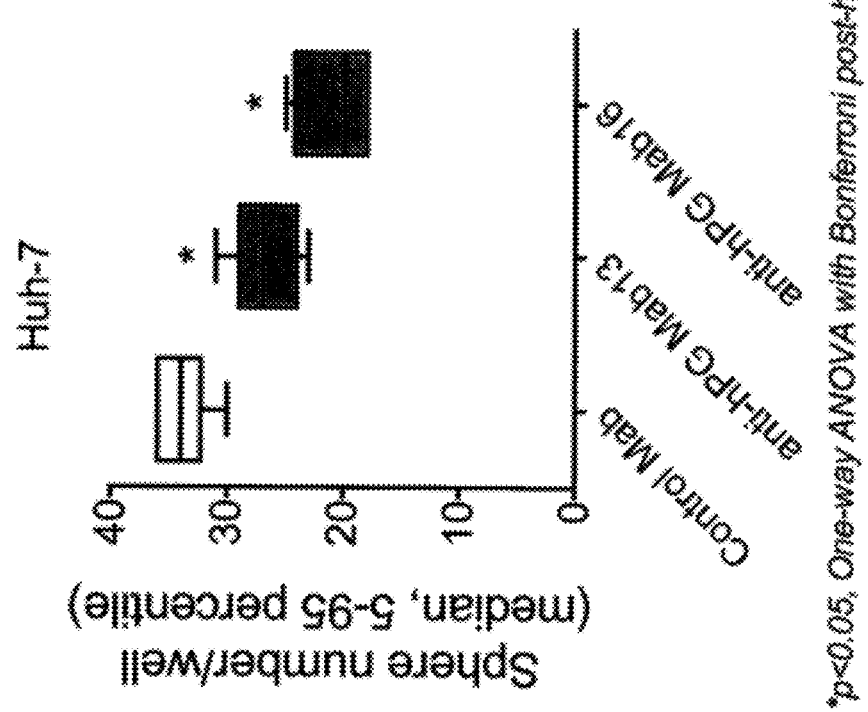

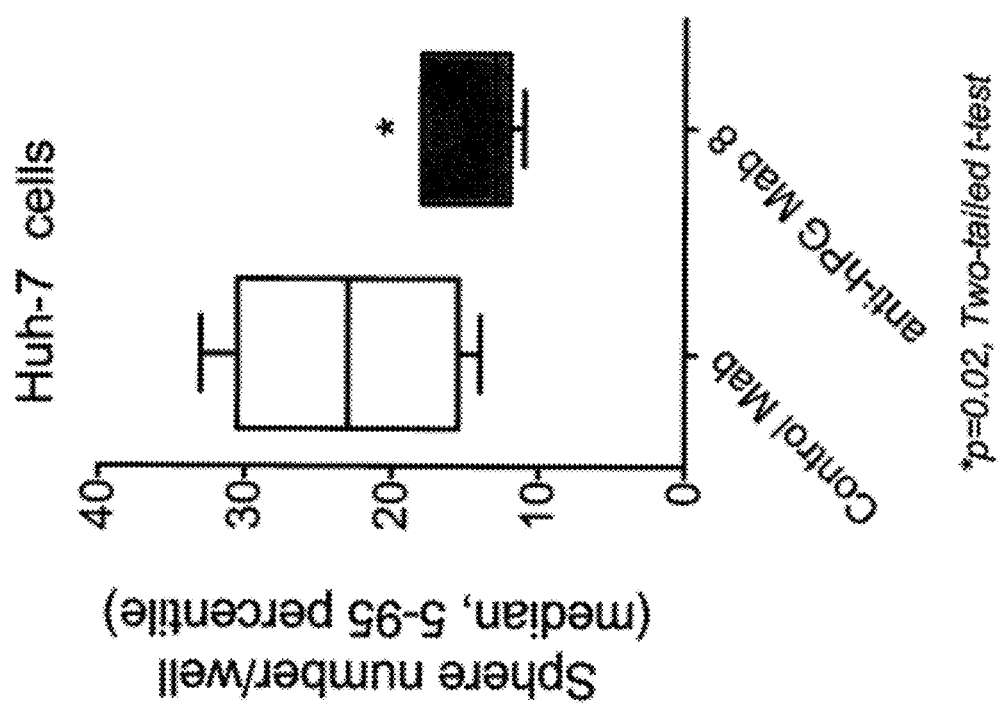

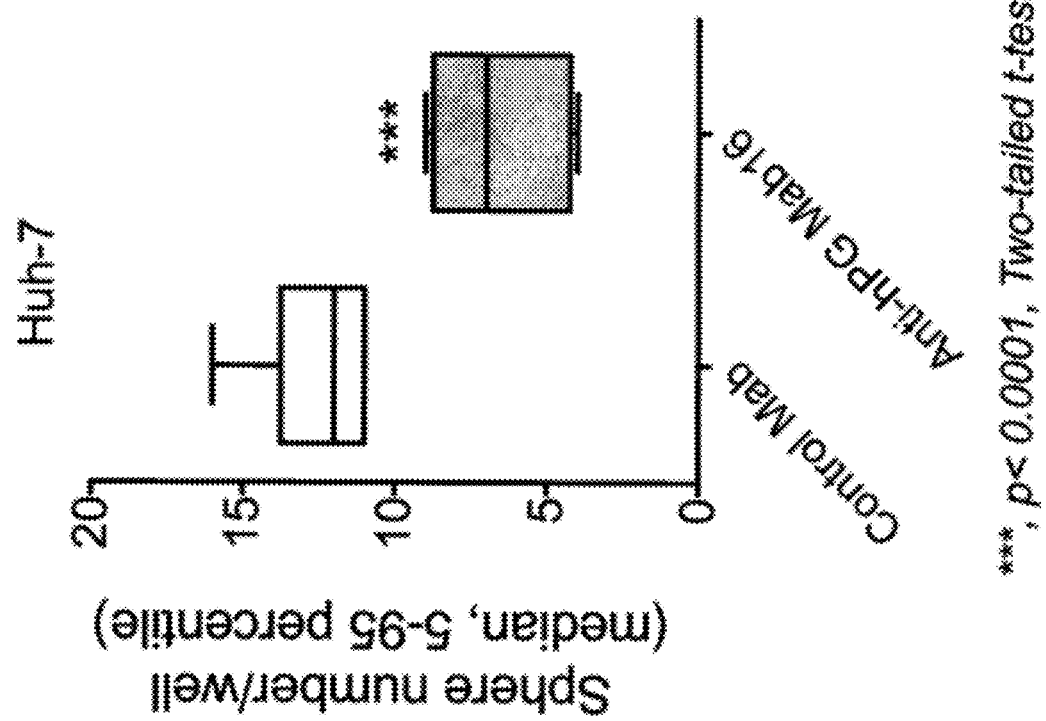

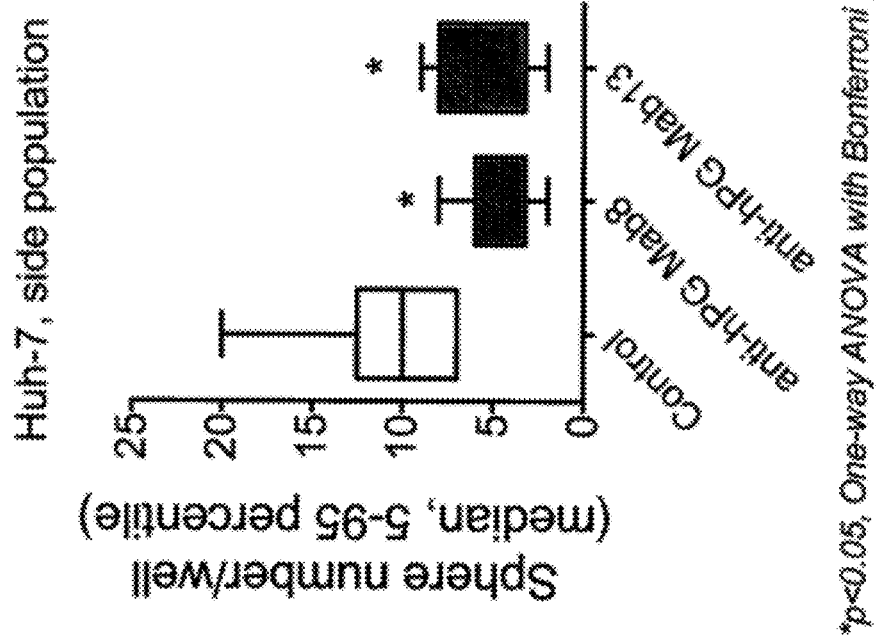

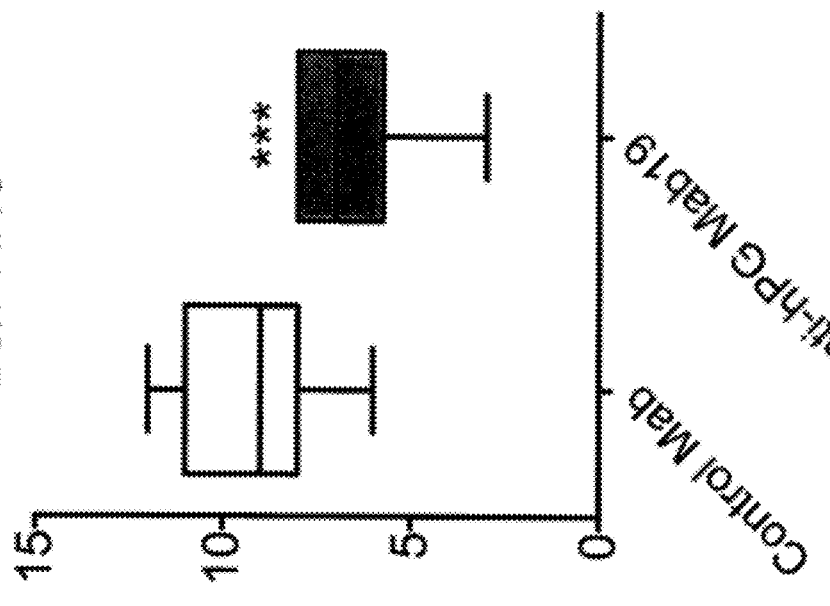

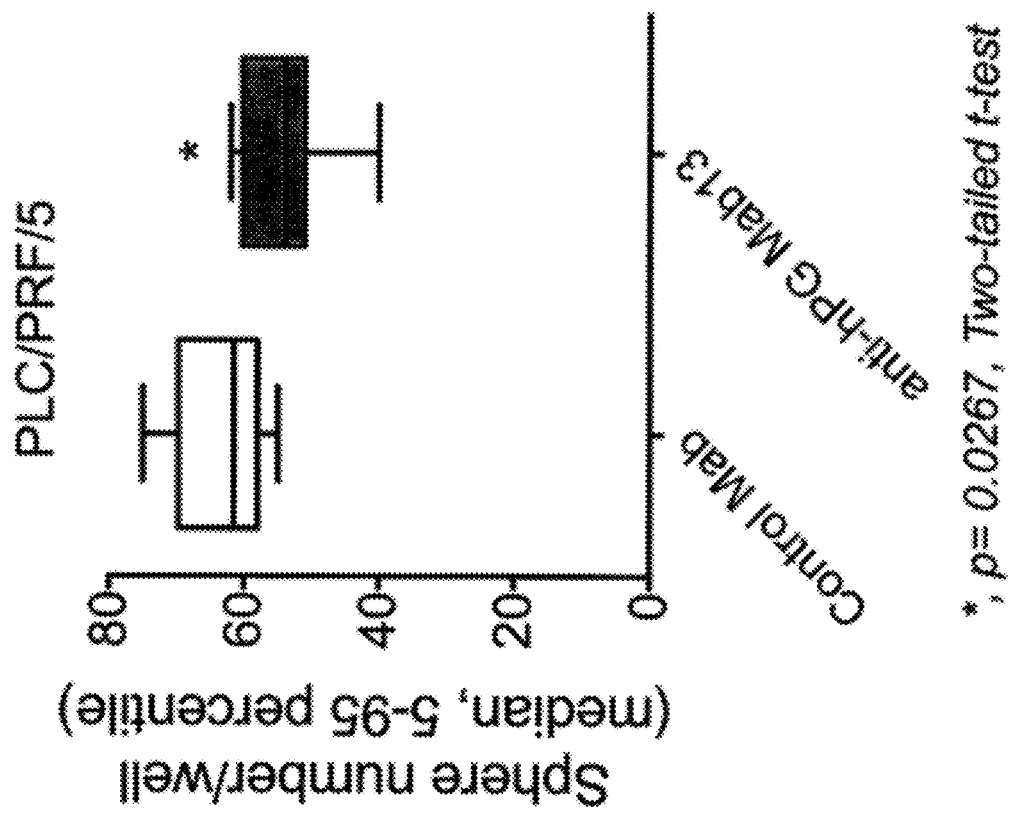

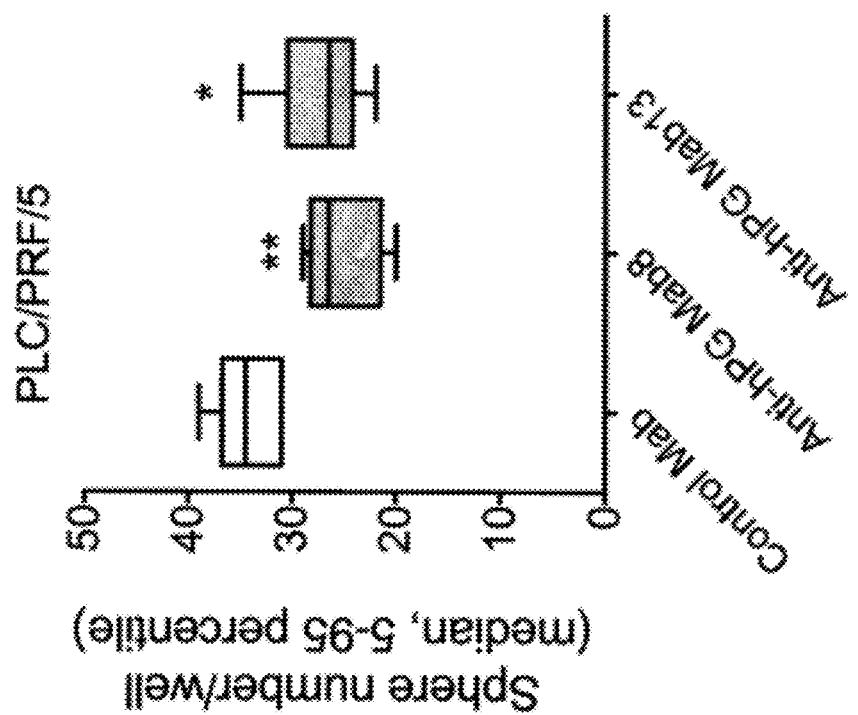

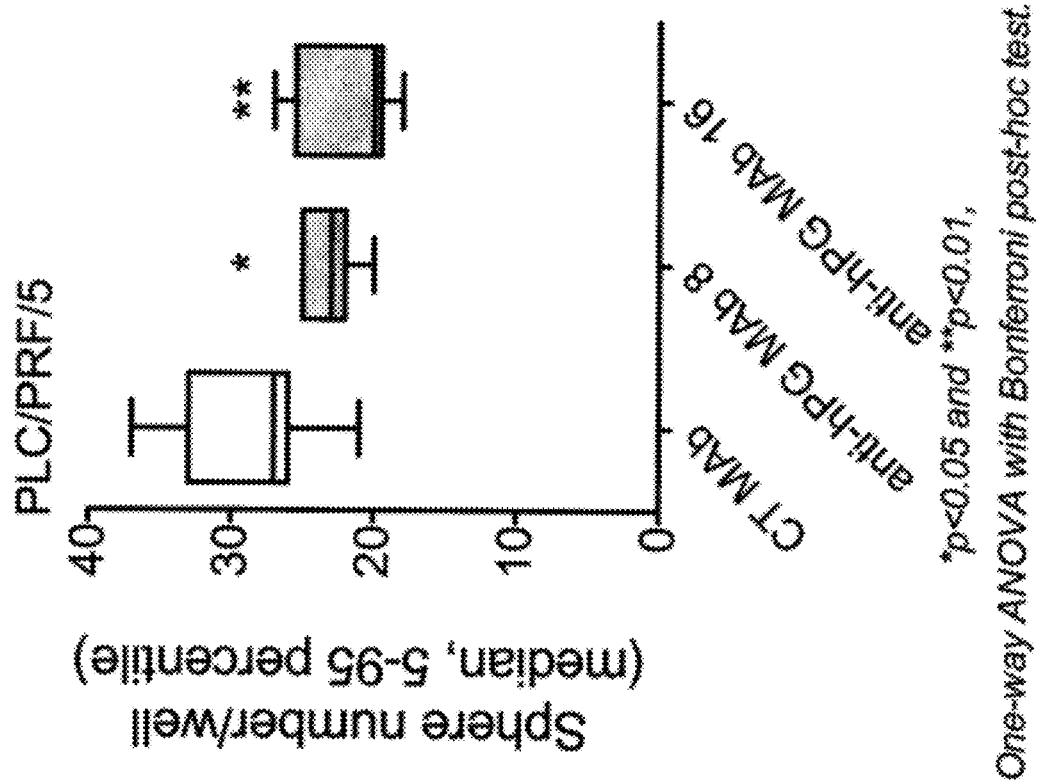

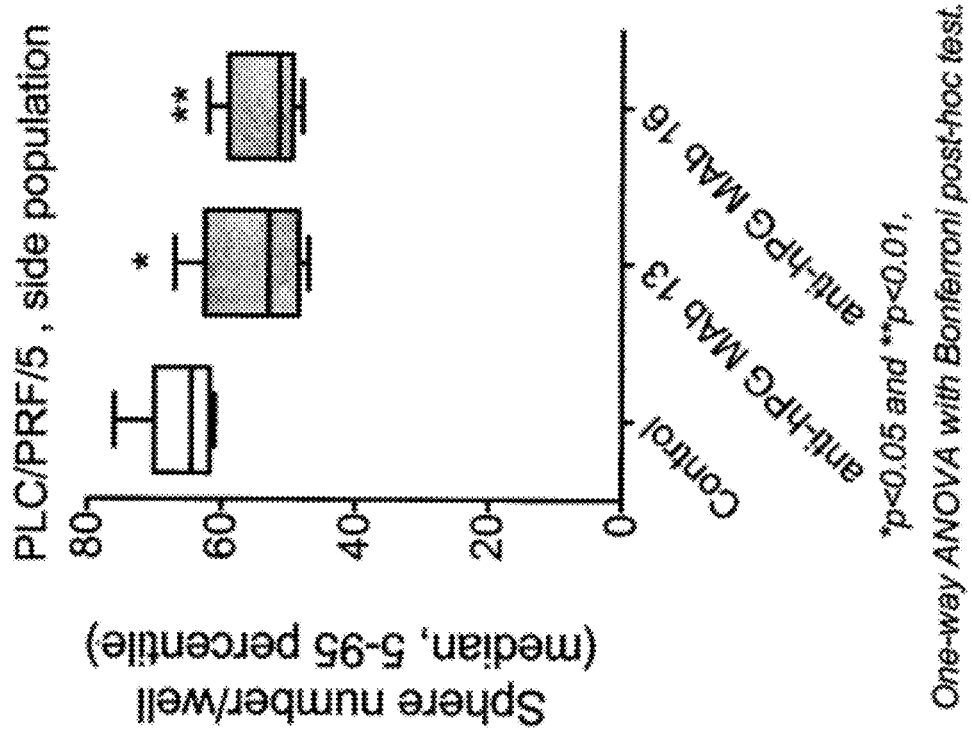

```
                        SEQUENCE LISTING

<160> NUMBER OF SEQ ID NOS: 106

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ile Phe Thr Ser Tyr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Tyr Pro Gly Asn Ser Asp Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Arg Arg Asp Ser Pro Gln Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Gln Ser Ile Val His Ser Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Gln Gly Ser His Val Pro Phe Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Thr Phe Ser Ser Ser Trp
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Leu Pro Gly Ser Gly Ser Thr
1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Thr Asp Gly Asn Tyr Asp Trp Phe Ala Tyr
1               5                   10

<210> SEQ ID NO 10
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 10

Gln Ser Leu Val His Ser Ser Gly Val Thr Tyr
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gln Ser Thr His Val Pro Pro Thr
1               5

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ile Phe Thr Ser Tyr
                20                  25                  30

Trp Val His Trp Val Lys Gln Arg Pro Gly Gln Gly Leu Glu Trp Ile
            35                  40                  45

Gly Gly Phe Tyr Pro Gly Asn Ser Asp Ser Arg Tyr Asn Gln Lys Phe
        50                  55                  60

Lys Gly Lys Ala Thr Leu Thr Ala Val Thr Ser Ala Ser Thr Ala Tyr
65                  70                  75                  80

Met Asp Leu Ser Ser Leu Thr Asn Glu Asp Ser Ala Val Tyr Phe Cys
                85                  90                  95

Thr Arg Arg Asp Ser Pro Gln Tyr Trp Gly Gln Gly Thr Thr Leu Thr
            100                 105                 110

Val Ser Ser
        115

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45
```

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Leu Glu Ala Glu Asp Leu Gly Val Tyr Tyr Cys Phe Gln Gly
                 85                  90                  95

Ser His Val Pro Phe Thr Phe Gly Gly Gly Thr Lys Leu Glu Ile Lys
            100                 105                 110

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Gln Ser Gly Ala Glu Leu Met Lys Pro Gly Ala
  1               5                  10                  15

Ser Val Lys Ile Ser Cys Lys Ala Thr Gly Tyr Thr Phe Ser Ser Ser
                 20                  25                  30

Trp Ile Glu Trp Leu Lys Gln Arg Pro Gly His Gly Leu Glu Trp Ile
             35                  40                  45

Gly Glu Phe Leu Pro Gly Ser Gly Ser Thr Asp Tyr Asn Glu Lys Phe
     50                  55                  60

Lys Gly Lys Ala Thr Phe Thr Ala Asp Thr Ser Ser Asp Thr Ala Tyr
 65                  70                  75                  80

Met Leu Leu Ser Ser Leu Thr Ser Glu Asp Ser Ala Val Tyr Tyr Cys
                 85                  90                  95

Ala Thr Asp Gly Asn Tyr Asp Trp Phe Ala Tyr Trp Gly Gln Gly Thr
            100                 105                 110

Leu Val Thr Val Ser Ala
        115

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Leu Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Val His Ser
                 20                  25                  30

Ser Gly Val Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Pro Thr Phe Gly Ser Gly Thr Lys Leu Glu Ile Lys
            100                 105                 110
```

<210> SEQ ID NO 16
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(345)

<400> SEQUENCE: 16

```
gag gtt cag ctc cag cag tct ggg act gtg ctg gca agg cct ggg gct      48
Glu Val Gln Leu Gln Gln Ser Gly Thr Val Leu Ala Arg Pro Gly Ala
1               5                   10                  15 tcc gtg aag atg tcc tgc aag gct tct ggc tac atc ttt acc agc tac      96
Ser Val Lys Met Ser Cys Lys Ala Ser Gly Tyr Ile Phe Thr Ser Tyr
            20                  25                  30 tgg gta cac tgg gtt aaa cag agg cct gga cag ggt cta gaa tgg att     144
Trp Val His Trp Val Lys Gln Arg Pro Gly Gln Gly Leu Glu Trp Ile
        35                  40                  45 ggt ggt ttt tat cct gga aat agt gat tct agg tac aac cag aaa ttc     192
Gly Gly Phe Tyr Pro Gly Asn Ser Asp Ser Arg Tyr Asn Gln Lys Phe
    50                  55                  60 aag ggc aag gcc aca ctg act gca gtc aca tcc gcc agt act gcc tac     240
Lys Gly Lys Ala Thr Leu Thr Ala Val Thr Ser Ala Ser Thr Ala Tyr
65                  70                  75                  80 atg gac ctc agc agc ctg aca aat gag gac tct gcg gtc tat ttc tgt     288
Met Asp Leu Ser Ser Leu Thr Asn Glu Asp Ser Ala Val Tyr Phe Cys
                85                  90                  95 aca aga aga gat agt ccc cag tac tgg ggc caa ggc acc act ctc aca     336
Thr Arg Arg Asp Ser Pro Gln Tyr Trp Gly Gln Gly Thr Thr Leu Thr
            100                 105                 110 gtc tcc tca                                                          345
Val Ser Ser
        115
```

<210> SEQ ID NO 17
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(336)

<400> SEQUENCE: 17

```
gat gtt ttg atg acc caa act cca ctc tcc ctg cct gtc agt ctt gga      48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt      96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct     144
Asn Gly Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65                  70                  75                  80
```

```
agc aga ctg gag gct gag gat ctg gga gtt tat tac tgc ttt caa ggt    288
Ser Arg Leu Glu Ala Glu Asp Leu Gly Val Tyr Tyr Cys Phe Gln Gly
                85                  90                  95 tca cat gtt ccg ttc acg ttc gga ggg ggg acc aag ctg gaa ata aaa    336
Ser His Val Pro Phe Thr Phe Gly Gly Gly Thr Lys Leu Glu Ile Lys
        100                 105                 110
```

<210> SEQ ID NO 18
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(354)

<400> SEQUENCE: 18

```
cag gtt cag ttg cag cag tct gga gct gag ctg atg aag cca ggg gcc     48
Gln Val Gln Leu Gln Gln Ser Gly Ala Glu Leu Met Lys Pro Gly Ala
1               5                   10                  15 tca gtg aag ata tcc tgc aag gct act ggc tac aca ttc agt agc tcc     96
Ser Val Lys Ile Ser Cys Lys Ala Thr Gly Tyr Thr Phe Ser Ser Ser
                20                  25                  30 tgg ata gag tgg tta aaa cag agg cct gga cat ggc ctt gag tgg att    144
Trp Ile Glu Trp Leu Lys Gln Arg Pro Gly His Gly Leu Glu Trp Ile
            35                  40                  45 gga gag ttt tta cct gga agt ggt agt aca gac tac aat gag aag ttc    192
Gly Glu Phe Leu Pro Gly Ser Gly Ser Thr Asp Tyr Asn Glu Lys Phe
        50                  55                  60 aag ggc aag gcc aca ttc act gca gac aca tcc tcc gac aca gcc tac    240
Lys Gly Lys Ala Thr Phe Thr Ala Asp Thr Ser Ser Asp Thr Ala Tyr
65                  70                  75                  80 atg cta ctc agc agc ctg aca tct gag gac tct gcc gtc tat tac tgt    288
Met Leu Leu Ser Ser Leu Thr Ser Glu Asp Ser Ala Val Tyr Tyr Cys
                85                  90                  95 gca act gat ggt aat tat gac tgg ttt gct tac tgg ggc caa ggg act    336
Ala Thr Asp Gly Asn Tyr Asp Trp Phe Ala Tyr Trp Gly Gln Gly Thr
        100                 105                 110 ctg gtc act gtc tct gca                                            354
Leu Val Thr Val Ser Ala
        115
```

<210> SEQ ID NO 19
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 19

```
gat ctt gtg atg acc caa act cca ctc tcc ctg cct gtc agt ctt gga     48
Asp Leu Val Met Thr Gln Thr Pro Leu Ser Leu Pro Val Ser Leu Gly
1               5                   10                  15 gat caa gcc tcc atc tct tgc aga tct agt cag agc ctt gta cac agt     96
Asp Gln Ala Ser Ile Ser Cys Arg Ser Ser Gln Ser Leu Val His Ser
                20                  25                  30 agt gga gtc acc tat tta cat tgg tac ctg cag aag cca ggc cag tct    144
Ser Gly Val Thr Tyr Leu His Trp Tyr Leu Gln Lys Pro Gly Gln Ser
```

```
cca aag ctc ctg atc tac aaa gtt tcc aac cga ttt tct ggg gtc cca        192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc        240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa agt        288
Ser Arg Val Glu Ala Glu Asp Leu Gly Val Tyr Phe Cys Ser Gln Ser
                85                  90                  95 aca cat gtt cct ccc acg ttc ggc tcg ggg aca aag ttg gaa ata aaa        336
Thr His Val Pro Pro Thr Phe Gly Ser Gly Thr Lys Leu Glu Ile Lys
            100                 105                 110
```

<210> SEQ ID NO 20
<211> LENGTH: 80
<212> TYPE: PRT
<213> ORGANISM: Homo sapiens

<400> SEQUENCE: 20

```
Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Gln Gln Gly Pro Ala
                20                  25                  30

Ser His His Arg Arg Gln Leu Gly Pro Gln Gly Pro Pro His Leu Val
            35                  40                  45

Ala Asp Pro Ser Lys Lys Gln Gly Pro Trp Leu Glu Glu Glu Glu
        50                  55                  60

Ala Tyr Gly Trp Met Asp Phe Gly Arg Arg Ser Ala Glu Asp Glu Asn
65                  70                  75                  80
```

<210> SEQ ID NO 21
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
                20                  25                  30

Trp Val His Trp Val Arg Gln Ala Pro Gly Gln Arg Leu Glu Trp Met
            35                  40                  45

Gly Gly Phe Tyr Pro Gly Asn Ser Asp Ser Arg Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Asp Ser Pro Gln Tyr Trp Gly Gln Gly Thr Leu Val Thr
            100                 105                 110

Val Ser Ser
        115
```

<210> SEQ ID NO 22
<211> LENGTH: 112

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Ser
            20                  25                  30

Trp Met His Trp Val Arg Gln Ala Pro Gly Gln Gly Leu Glu Trp Met
        35                  40                  45

Gly Ile Phe Leu Pro Gly Ser Gly Ser Thr Asp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Asp Gly Asn Tyr Asp Trp Phe Ala Tyr Trp Gly Gln Gly Thr
            100                 105                 110

Leu Val Thr Val Ser Ser
        115

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
```

```
                20                  25                  30
Ser Gly Val Thr Tyr Leu Tyr Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110

<210> SEQ ID NO 25
<211> LENGTH: 14
<212> TYPE: PRT
<213> ORGANISM: Homo sapiens

<400> SEQUENCE: 25

Ser Trp Lys Pro Arg Ser Gln Gln Pro Asp Ala Pro Leu Gly
 1               5                  10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ahx

<400> SEQUENCE: 26

Ser Trp Lys Pro Arg Ser Gln Gln Pro Asp Ala Pro Leu Gly Xaa Cys
 1               5                  10                  15

<210> SEQ ID NO 27
<211> LENGTH: 26
<212> TYPE: PRT
<213> ORGANISM: Homo sapiens

<400> SEQUENCE: 27

Gln Gly Pro Trp Leu Glu Glu Glu Glu Ala Tyr Gly Trp Met Asp
 1               5                  10                  15

Phe Gly Arg Arg Ser Ala Glu Asp Glu Asn
            20                  25

<210> SEQ ID NO 28
<211> LENGTH: 5
<212> TYPE: PRT
<213> ORGANISM: Homo sapiens

<400> SEQUENCE: 28

Asp Ala Pro Leu Gly
 1               5

<210> SEQ ID NO 29
<211> LENGTH: 6
<212> TYPE: PRT
<213> ORGANISM: Homo sapiens

<400> SEQUENCE: 29
```

Pro Asp Ala Pro Leu Gly
1               5

<210> SEQ ID NO 30
<211> LENGTH: 7
<212> TYPE: PRT
<213> ORGANISM: Homo sapiens

<400> SEQUENCE: 30

Pro Arg Ser Gln Gln Pro Asp
1               5

<210> SEQ ID NO 31
<211> LENGTH: 9
<212> TYPE: PRT
<213> ORGANISM: Homo sapiens

<400> SEQUENCE: 31

Trp Lys Pro Arg Ser Gln Gln Pro Asp
1               5

<210> SEQ ID NO 32
<211> LENGTH: 13
<212> TYPE: PRT
<213> ORGANISM: Homo sapiens

<400> SEQUENCE: 32

Trp Lys Pro Arg Ser Gln Gln Pro Asp Ala Pro Leu Gly
1               5                   10

<210> SEQ ID NO 33
<211> LENGTH: 4
<212> TYPE: PRT
<213> ORGANISM: Homo sapiens

<400> SEQUENCE: 33

Phe Gly Arg Arg
1

<210> SEQ ID NO 34
<211> LENGTH: 5
<212> TYPE: PRT
<213> ORGANISM: Homo sapiens

<400> SEQUENCE: 34

Met Asp Phe Gly Arg
1               5

<210> SEQ ID NO 35
<211> LENGTH: 5
<212> TYPE: PRT
<213> ORGANISM: Homo sapiens

<400> SEQUENCE: 35

Ala Glu Asp Glu Asn
1               5

<210> SEQ ID NO 36
<211> LENGTH: 8
<212> TYPE: PRT
<213> ORGANISM: Homo sapiens

<400> SEQUENCE: 36

Gly Trp Met Asp Phe Gly Arg Arg
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Thr Phe Thr Thr Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Phe Ile Phe Ser Ser Tyr Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Tyr Thr Phe Thr Ser Tyr Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Tyr Ser Ile Thr Ser Asp Tyr Ala
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Ser Ser Gly Gly Thr Tyr Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Asn Thr Phe Gly Asp Arg Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Asn Pro Ser Asn Gly Gly Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Phe Ser Gly Tyr Thr
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Thr Gln Gly Asn Tyr Ser Leu Asp Phe
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Arg Gly Thr Gly Thr Tyr
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Arg Gly Gly Tyr Tyr Pro Phe Asp Tyr
1               5                   10

<210> SEQ ID NO 48
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Arg Glu Val Asn Tyr Gly Asp Ser Tyr His Phe Asp Tyr
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ser Leu Arg His Thr Lys Gly Ile Thr Phe
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ser Leu Leu Asp Ser Asp Gly Lys Thr Tyr
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Gln His Arg Thr Tyr Thr
1               5

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Met Ser
1

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Val Ser
```

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Lys Lys Asp Gly Ser His
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Gln Asn Leu Glu Leu Pro Leu Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Gln Gly Thr His Phe Pro Gln Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Gln Gly Thr His Ser Pro Tyr Thr
1               5

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Val Gly Asp Ala Ile Lys Gly Gln Ser Val Phe Val
1               5                   10

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Thr Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Ala Leu Tyr
65                  70                  75                  80

Leu Gln Met Ser Ser Leu Arg Ser Glu Asp Thr Ala Met Tyr Tyr Cys
                85                  90                  95

Ala Thr Gln Gly Asn Tyr Ser Leu Asp Phe Trp Gly Gln Gly Thr Ser
            100                 105                 110

Leu Thr Val Ser Ser
        115

<210> SEQ ID NO 60
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Ser Tyr
            20                  25                  30

Gly Met Ser Trp Val Arg Gln Ser Pro Asp Arg Arg Leu Glu Leu Val
        35                  40                  45

Ala Ser Ile Asn Thr Phe Gly Asp Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Ser Glu Asp Thr Ala Ile Tyr Tyr Cys
                85                  90                  95

Ala Arg Gly Thr Gly Thr Tyr Trp Gly Gln Gly Thr Leu Thr Val
            100                 105                 110

Ser Ser

<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
            35                  40                  45

Gly Glu Ile Asn Pro Ser Asn Gly Gly Thr Asn Phe Asn Glu Lys Phe
 50                      55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Gly Gly Tyr Tyr Pro Phe Asp Tyr Trp Gly Gln Gly Thr Thr
            100                 105                 110

Leu Thr Val Ser Ser
        115

<210> SEQ ID NO 62
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
            35                  40                  45

Met Gly Tyr Ile Ser Phe Ser Gly Tyr Thr Tyr Asn Pro Ser Leu
 50                      55                  60

Lys Ser Arg Ile Ser Val Thr Arg Asp Thr Ser Arg Asn Gln Phe Phe
 65                  70                  75                  80

Leu Gln Leu Thr Ser Val Thr Thr Glu Asp Thr Ala Thr Tyr Tyr Cys
                 85                  90                  95

Ala Arg Glu Val Asn Tyr Gly Asp Ser Tyr His Phe Asp Tyr Trp Gly
            100                 105                 110

Gln Gly Thr Ile Val Thr Val Ser Ser
        115                 120

<210> SEQ ID NO 63
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Val Met Thr Gln Ala Ala Ser Asn Pro Val Thr Leu Gly
 1               5                  10                  15

Thr Ser Ala Ser Ile Ser Cys Arg Ser Lys Ser Leu Arg His Thr
            20                  25                  30

Lys Gly Ile Thr Phe Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
        50                  55                  60

Asp Arg Phe Ser Ser Ser Gly Ser Gly Thr Asp Phe Thr Leu Arg Ile
 65                  70                  75                  80

Ser Arg Val Glu Ala Glu Asp Leu Gly Val Tyr Tyr Cys Ala Gln Asn
             85                  90                  95

Leu Glu Leu Pro Leu Thr Phe Gly Ala Gly Thr Lys Leu Glu Leu Lys
            100                 105                 110

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Val Val Leu Thr Gln Thr Pro Leu Thr Leu Ser Val Thr Ile Gly
1               5                  10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
             85                  90                  95

Thr His Phe Pro Gln Thr Phe Gly Gly Gly Thr Lys Leu Glu Ile Lys
            100                 105                 110

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Val Val Met Thr Gln Thr Pro Leu Thr Leu Ser Val Thr Ile Gly
1               5                  10                  15

Arg Pro Ala Ser Ile Ser Cys Lys Ser Ser Gln Ser Leu Leu Asp Ser
            20                  25                  30

Asp Gly Lys Thr Tyr Leu Tyr Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Ile Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
             85                  90                  95

Thr His Ser Pro Tyr Thr Phe Gly Gly Gly Thr Lys Leu Glu Ile Lys
            100                 105                 110

<210> SEQ ID NO 66
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Leu Ala Leu Thr Gln Ser Ser Ser Ala Ser Phe Ser Leu Gly Ala
1               5                   10                  15

Ser Ala Lys Leu Thr Cys Thr Leu Ser Ser Gln His Arg Thr Tyr Thr
            20                  25                  30

Ile Glu Trp Tyr Gln Gln Ser Leu Lys Pro Pro Lys Tyr Val Met
        35                  40                  45

Glu Val Lys Lys Asp Gly Ser His Ser Thr Gly His Gly Ile Pro Asp
50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
                85                  90                  95

Ala Ile Lys Gly Gln Ser Val Phe Val Phe Gly Gly Thr Lys Val
            100                 105                 110

Thr Val Leu
        115

<210> SEQ ID NO 67
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 67 gaa gtg cag ctg gtg gag tct ggg gga ggc tta gtg aag cct gga ggg        48
Glu Val Gln Leu Val Glu Ser Gly Gly Gly Leu Val Lys Pro Gly Gly
1               5                   10                  15 tcc ctg aaa ctc tcc tgt gca gcc tct gga ttc act ttc act acc tat       96
Ser Leu Lys Leu Ser Cys Ala Ala Ser Gly Phe Thr Phe Thr Thr Tyr
            20                  25                  30 gcc atg tct tgg gtt cgc cag act ccg gag aag agg ctg gag tgg gtc      144
Ala Met Ser Trp Val Arg Gln Thr Pro Glu Lys Arg Leu Glu Trp Val
        35                  40                  45 gca acc att agt agt ggt ggt act tac acc tac tat cca gac agt gtg      192
Ala Thr Ile Ser Ser Gly Gly Thr Tyr Thr Tyr Tyr Pro Asp Ser Val
50                  55                  60 aag ggt cga ttc acc atc tcc aga gac aat gcc aag aac gcc cta tac      240
Lys Gly Arg Phe Thr Ile Ser Arg Asp Asn Ala Lys Asn Ala Leu Tyr
65                  70                  75                  80 ctg caa atg agc agt ctg agg tct gag gac acg gcc atg tat tac tgt      288
Leu Gln Met Ser Ser Leu Arg Ser Glu Asp Thr Ala Met Tyr Tyr Cys
                85                  90                  95 gca aca cag ggg aat tac tct ttg gac ttc tgg ggc caa ggc acc tct      336
Ala Thr Gln Gly Asn Tyr Ser Leu Asp Phe Trp Gly Gln Gly Thr Ser
            100                 105                 110 ctc aca gtc tcc tca                                                  351
Leu Thr Val Ser Ser
        115

<210> SEQ ID NO 68
<211> LENGTH: 342
<212> TYPE: DNA
<213> ORGANISM: Artificial Sequence
<220> FEATURE:
<223> OTHER INFORMATION: Description of Artificial Sequence: Synthetic

```
        polynucleotide
<220> FEATURE:
<221> NAME/KEY: CDS
<222> LOCATION: (1)..(342)

<400> SEQUENCE: 68 gag gtg cag ctg gtg gag tct ggg gga ggc ttg gtg cag cct gga ggg      48
Glu Val Gln Leu Val Glu Ser Gly Gly Gly Leu Val Gln Pro Gly Gly
1               5                   10                  15 tcc ctg aaa ctc tcc tgt gca gcc tct gga ttc att ttc agt agc tat      96
Ser Leu Lys Leu Ser Cys Ala Ala Ser Gly Phe Ile Phe Ser Ser Tyr
            20                  25                  30 ggc atg tct tgg gtt cgc cag tct cca gac agg agg ctg gag ttg gtc     144
Gly Met Ser Trp Val Arg Gln Ser Pro Asp Arg Arg Leu Glu Leu Val
        35                  40                  45 gca agt att aat act ttt ggt gat aga acc tat tat cca gac agt gtg     192
Ala Ser Ile Asn Thr Phe Gly Asp Arg Thr Tyr Tyr Pro Asp Ser Val
    50                  55                  60 aag ggc cga ttc acc atc tcc aga gac aat gcc aag aac acc ctg tac     240
Lys Gly Arg Phe Thr Ile Ser Arg Asp Asn Ala Lys Asn Thr Leu Tyr
65                  70                  75                  80 ctg caa atg acc agt ctg aag tct gag gac aca gcc att tat tac tgt     288
Leu Gln Met Thr Ser Leu Lys Ser Glu Asp Thr Ala Ile Tyr Tyr Cys
                85                  90                  95 gca aga ggg acc gga acc tac tgg ggc caa ggc acc act ctc aca gtc     336
Ala Arg Gly Thr Gly Thr Tyr Trp Gly Gln Gly Thr Thr Leu Thr Val
            100                 105                 110 tcc tca                                                              342
Ser Ser <210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 69 cag gtc caa ctg cag cag tct ggg gct gaa ctg gtg aag cct ggg gct      48
Gln Val Gln Leu Gln Gln Ser Gly Ala Glu Leu Val Lys Pro Gly Ala
1               5                   10                  15 tca gtg aag ttg tcc tgc aag gct tct ggc tac acc ttc acc agc tac      96
Ser Val Lys Leu Ser Cys Lys Ala Ser Gly Tyr Thr Phe Thr Ser Tyr
            20                  25                  30 tat atg tac tgg gtg aag cag agg cct gga caa ggc ctt gag tgg att     144
Tyr Met Tyr Trp Val Lys Gln Arg Pro Gly Gln Gly Leu Glu Trp Ile
        35                  40                  45 gga gag att aat cct agc aat ggt ggt act aac ttc aat gag aag ttc     192
Gly Glu Ile Asn Pro Ser Asn Gly Gly Thr Asn Phe Asn Glu Lys Phe
    50                  55                  60 aag agc aag gcc aca ctg act gta gac aaa tcc tcc agc aca gca tac     240
Lys Ser Lys Ala Thr Leu Thr Val Asp Lys Ser Ser Ser Thr Ala Tyr
65                  70                  75                  80 atg caa ctc agc agc ctg aca tct gag gac tct gcg gtc tat tac tgt     288
Met Gln Leu Ser Ser Leu Thr Ser Glu Asp Ser Ala Val Tyr Tyr Cys
                85                  90                  95 aca aga ggc ggt tac tac ccc ttt gac tac tgg ggc caa ggc acc act     336
Thr Arg Gly Gly Tyr Tyr Pro Phe Asp Tyr Trp Gly Gln Gly Thr Thr
            100                 105                 110
```

```
ctc aca gtc tcc tca                                                     351
Leu Thr Val Ser Ser
        115

<210> SEQ ID NO 70
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 70 gat gtg cag ctt cag gag tcg gga cct ggc ctg gtg aaa cct tct cag        48
Asp Val Gln Leu Gln Glu Ser Gly Pro Gly Leu Val Lys Pro Ser Gln
1               5                   10                  15 tct ctg tcc ctc aca tgc act gtc act ggc tac tca atc acc agt gat        96
Ser Leu Ser Leu Thr Cys Thr Val Thr Gly Tyr Ser Ile Thr Ser Asp
            20                  25                  30 tat gcc tgg aat tgg atc cgg cag ttt cca gga aac aaa ctg gag tgg       144
Tyr Ala Trp Asn Trp Ile Arg Gln Phe Pro Gly Asn Lys Leu Glu Trp
        35                  40                  45 atg ggc tac ata agc ttc agt ggt tac act agt tac aac cca tct ctc       192
Met Gly Tyr Ile Ser Phe Ser Gly Tyr Thr Ser Tyr Asn Pro Ser Leu
    50                  55                  60 aaa agt cga atc tct gtc act cgg gac aca tcc agg aac caa ttc ttc       240
Lys Ser Arg Ile Ser Val Thr Arg Asp Thr Ser Arg Asn Gln Phe Phe
65                  70                  75                  80 ctc cag ttg act tct gtg act act gag gac aca gcc aca tat tac tgt       288
Leu Gln Leu Thr Ser Val Thr Thr Glu Asp Thr Ala Thr Tyr Tyr Cys
                85                  90                  95 gca aga gag gtc aac tat ggg gac tcc tac cac ttt gac tac tgg ggc       336
Ala Arg Glu Val Asn Tyr Gly Asp Ser Tyr His Phe Asp Tyr Trp Gly
            100                 105                 110 caa ggc acc att gtc aca gtc tcc tca                                   363
Gln Gly Thr Ile Val Thr Val Ser Ser
        115                 120

<210> SEQ ID NO 71
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 71 gac att gtg atg acg cag gct gca tcc tct aat cca gtc act ctt gga        48
Asp Ile Val Met Thr Gln Ala Ala Ser Ser Asn Pro Val Thr Leu Gly
1               5                   10                  15 aca tcc gct tcc atc tcc tgc agg tct agt aag agt ctc cga cat act        96
Thr Ser Ala Ser Ile Ser Cys Arg Ser Ser Lys Ser Leu Arg His Thr
            20                  25                  30 aaa ggc atc act ttt ttg tat tgg tat ctg cag aag cca ggc cag tct       144
Lys Gly Ile Thr Phe Leu Tyr Trp Tyr Leu Gln Lys Pro Gly Gln Ser
        35                  40                  45 cct cag ctc ctg att tat cag atg tcc aac ctt gcc tca gga gtc cca       192
Pro Gln Leu Leu Ile Tyr Gln Met Ser Asn Leu Ala Ser Gly Val Pro
```

```
                50                  55                  60
gac agg ttc agt agc agt ggg tca gga act gat ttc aca ctg aga atc        240
Asp Arg Phe Ser Ser Ser Gly Ser Gly Thr Asp Phe Thr Leu Arg Ile
 65                  70                  75                  80 agc aga gtg gag gct gag gat ttg ggt gtt tat tac tgt gct caa aat        288
Ser Arg Val Glu Ala Glu Asp Leu Gly Val Tyr Tyr Cys Ala Gln Asn
                 85                  90                  95 cta gaa ctt ccg ctc acg ttc ggt gct ggg acc aag ctg gag ctg aaa        336
Leu Glu Leu Pro Leu Thr Phe Gly Ala Gly Thr Lys Leu Glu Leu Lys
            100                 105                 110

<210> SEQ ID NO 72
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 72 gat gtt gtg ctg acc cag act cca ctc act ttg tcg gtt acc att gga         48
Asp Val Val Leu Thr Gln Thr Pro Leu Thr Leu Ser Val Thr Ile Gly
  1               5                  10                  15 caa cca gcc tcc atc tcc tgc aag tca agt cag agc ctc tta gat agt         96
Gln Pro Ala Ser Ile Ser Cys Lys Ser Ser Gln Ser Leu Leu Asp Ser
             20                  25                  30 gat gga aag aca tat ttg aat tgg ttg tta cag agg cca ggc cag tct        144
Asp Gly Lys Thr Tyr Leu Asn Trp Leu Leu Gln Arg Pro Gly Gln Ser
         35                  40                  45 cca aag cgc cta atc tat ctg gtg tct aaa ctg gac tct gga gtc cct        192
Pro Lys Arg Leu Ile Tyr Leu Val Ser Lys Leu Asp Ser Gly Val Pro
     50                  55                  60 gac agg ttc act ggc agt gga tca ggg aca gat ttc aca ctg aaa atc        240
Asp Arg Phe Thr Gly Ser Gly Ser Gly Thr Asp Phe Thr Leu Lys Ile
 65                  70                  75                  80 agc aga gtg gag gct gag gat ttg gga gtt tat tat tgc tgg caa ggt        288
Ser Arg Val Glu Ala Glu Asp Leu Gly Val Tyr Tyr Cys Trp Gln Gly
                 85                  90                  95 aca cat ttt cct cag acg ttc ggt gga ggc acc aag ctg gaa atc aaa        336
Thr His Phe Pro Gln Thr Phe Gly Gly Gly Thr Lys Leu Glu Ile Lys
            100                 105                 110

<210> SEQ ID NO 73
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 73 gat gtt gtg atg acc cag act cca ctc act ttg tcg gtt acc att ggg         48
Asp Val Val Met Thr Gln Thr Pro Leu Thr Leu Ser Val Thr Ile Gly
  1               5                  10                  15 cgc cca gcc tcc atc tct tgc aag tca agt cag agc ctc tta gac agt         96
Arg Pro Ala Ser Ile Ser Cys Lys Ser Ser Gln Ser Leu Leu Asp Ser
             20                  25                  30 gat gga aag aca tat ttg tat tgg ttg tta cag agg cca ggc cag tct        144
```

```
                Asp Gly Lys Thr Tyr Leu Tyr Trp Leu Leu Gln Arg Pro Gly Gln Ser
                         35                  40                  45 cca aag cgc cta atc tat ctg gtg tct gag ctg gac tct gga gtc cct      192
Pro Lys Arg Leu Ile Tyr Leu Val Ser Glu Leu Asp Ser Gly Val Pro
         50                  55                  60 gac agg atc act ggc agt ggg tcg ggg aca gat ttc aca ctg aag atc      240
Asp Arg Ile Thr Gly Ser Gly Ser Gly Thr Asp Phe Thr Leu Lys Ile
65                  70                  75                  80 agc aga gtg gag gct gag gat ttg gga gtt tat tat tgc tgg caa gga      288
Ser Arg Val Glu Ala Glu Asp Leu Gly Val Tyr Tyr Cys Trp Gln Gly
                85                  90                  95 aca cat tct ccg tac acg ttc gga ggg ggg acc aag ctg gaa ata aaa      336
Thr His Ser Pro Tyr Thr Phe Gly Gly Gly Thr Lys Leu Glu Ile Lys
            100                 105                 110
```

<210> SEQ ID NO 74
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(345)

<400> SEQUENCE: 74

```
caa ctt gcg ctc act cag tca tct tca gcc tct ttc tcc ctg gga gcc      48
Gln Leu Ala Leu Thr Gln Ser Ser Ser Ala Ser Phe Ser Leu Gly Ala
1               5                   10                  15 tca gca aaa cta acg tgc act ttg agt agt caa cac aga acg tac acc      96
Ser Ala Lys Leu Thr Cys Thr Leu Ser Ser Gln His Arg Thr Tyr Thr
            20                  25                  30 att gaa tgg tat cag caa cag tca ctc aag cct cct aag tat gtg atg      144
Ile Glu Trp Tyr Gln Gln Gln Ser Leu Lys Pro Pro Lys Tyr Val Met
        35                  40                  45 gag gtt aag aaa gat gga agc cac agc aca ggt cat ggg att cct gat      192
Glu Val Lys Lys Asp Gly Ser His Ser Thr Gly His Gly Ile Pro Asp
    50                  55                  60 cgc ttc tct gga tcc agt tct ggt gct gat cgc tac ctc agc att tcc      240
Arg Phe Ser Gly Ser Ser Ser Gly Ala Asp Arg Tyr Leu Ser Ile Ser
65                  70                  75                  80 aac atc cag cct gaa gat gaa gca ata tac atc tgt ggt gtg ggt gat      288
Asn Ile Gln Pro Glu Asp Glu Ala Ile Tyr Ile Cys Gly Val Gly Asp
                85                  90                  95 gca att aag gga caa tct gtg ttt gtt ttc ggc ggt ggc acc aag gtc      336
Ala Ile Lys Gly Gln Ser Val Phe Val Phe Gly Gly Gly Thr Lys Val
            100                 105                 110 act gtc cta                                                          345
Thr Val Leu
        115
```

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Glu Val Gln Leu Val Glu Ser Gly Gly Gly Leu Val Lys Pro Gly Gly
1               5                   10                  15
```

-continued

```
Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Asn Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Asp Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 79
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Thr Ile Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 80
<211> LENGTH: 114
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 81
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

<210> SEQ ID NO 82
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
            35                  40                  45

Ala Ser Ile Asn Thr Phe Gly Asp Arg Thr Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 83
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

```
Thr Arg Gly Gly Tyr Tyr Pro Phe Asp Tyr Trp Gly Gln Gly Thr Thr
                100                 105                 110

Val Thr Val Ser Ser
        115

<210> SEQ ID NO 85
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 86
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 87
<211> LENGTH: 112
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 87

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 88
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 89
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser

```
            35                  40                  45
Pro Arg Arg Leu Ile Tyr Leu Val Ser Glu Arg Asp Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 90
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 91
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
```

Glu Ile Lys
        115

<210> SEQ ID NO 92
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 93
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Ala Trp His Gln Gln Pro Glu Lys Gly Pro Arg Tyr Leu Met Lys
        35                  40                  45

Val Lys Lys Asp Gly Ser His Ser Lys Gly Asp Gly Ile Pro Asp Arg
    50                  55                  60

Phe Ser Gly Ser Ser Ser Gly Ala Glu Arg Tyr Leu Thr Ile Ser Ser
65                  70                  75                  80

Leu Gln Ser Glu Asp Glu Ala Asp Tyr Tyr Cys Gly Val Gly Asp Ala
                85                  90                  95

Ile Lys Gly Gln Ser Val Phe Val Phe Gly Gly Gly Thr Lys Val Glu
            100                 105                 110

Ile Lys
115

<210> SEQ ID NO 94
<211> LENGTH: 121
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 95
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Gln Pro Glu Lys Gly Pro Arg Tyr Leu Met
        35                  40                  45

Glu Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115

<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

```
<400> SEQUENCE: 96

Cys Xaa Xaa Gln Gly Pro Trp Leu Glu Glu Glu Glu Ala Tyr Gly
1               5                   10                  15

Trp Met Asp Phe Gly Arg Arg Ser Ala Glu Asp Glu Asn
            20                  25

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 97

Cys Xaa Xaa Phe Gly Arg Arg Ser Ala Glu Asp Glu Asn
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Ahx

<400> SEQUENCE: 98

Phe Gly Arg Arg Ser Ala Glu Asp Glu Asn Xaa Xaa Cys
1               5                   10

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Ser Gly Gly Gly Ser Gly Gly Gly Gly Ser
1               5                   10                  15

<210> SEQ ID NO 100
<211> LENGTH: 101
<212> TYPE: PRT
<213> ORGANISM: Homo sapiens

<400> SEQUENCE: 100

Met Gln Arg Leu Cys Val Tyr Val Leu Ile Phe Ala Leu Ala Leu Ala
1               5                   10                  15

Ala Phe Ser Glu Ala Ser Trp Lys Pro Arg Ser Gln Gln Pro Asp Ala
            20                  25                  30

Pro Leu Gly Thr Gly Ala Asn Arg Asp Leu Glu Leu Pro Trp Leu Glu
        35                  40                  45

Gln Gln Gly Pro Ala Ser His His Arg Arg Gln Leu Gly Pro Gln Gly
    50                  55                  60
```

```
Pro Pro His Leu Val Ala Asp Pro Ser Lys Lys Gln Gly Pro Trp Leu
 65                  70                  75                  80

Glu Glu Glu Glu Glu Ala Tyr Gly Trp Met Asp Phe Gly Arg Arg Ser
                 85                  90                  95

Ala Glu Asp Glu Asn
            100

<210> SEQ ID NO 101
<211> LENGTH: 80
<212> TYPE: PRT
<213> ORGANISM: Homo sapiens

<400> SEQUENCE: 101

Ser Trp Lys Pro Arg Ser Gln Gln Pro Asp Ala Pro Leu Gly Thr Gly
 1               5                  10                  15

Ala Asn Arg Asp Leu Glu Leu Pro Trp Leu Glu Gln Gln Gly Pro Ala
             20                  25                  30

Ser His His Arg Arg Gln Leu Gly Pro Gln Gly Pro Pro His Leu Val
         35                  40                  45

Ala Asp Pro Ser Lys Lys Gln Gly Pro Trp Leu Glu Glu Glu Glu Glu
 50                  55                  60

Ala Tyr Gly Trp Met Asp Phe Gly Arg Arg Ser Ala Glu Asp Glu Asn
 65                  70                  75                  80

<210> SEQ ID NO 102
<211> LENGTH: 34
<212> TYPE: PRT
<213> ORGANISM: Homo sapiens

<400> SEQUENCE: 102

Gln Leu Gly Pro Gln Gly Pro Pro His Leu Val Ala Asp Pro Ser Lys
 1               5                  10                  15

Lys Gln Gly Pro Trp Leu Glu Glu Glu Glu Glu Ala Tyr Gly Trp Met
             20                  25                  30

Asp Phe

<210> SEQ ID NO 103
<211> LENGTH: 35
<212> TYPE: PRT
<213> ORGANISM: Homo sapiens

<400> SEQUENCE: 103

Gln Leu Gly Pro Gln Gly Pro Pro His Leu Val Ala Asp Pro Ser Lys
 1               5                  10                  15

Lys Gln Gly Pro Trp Leu Glu Glu Glu Glu Glu Ala Tyr Gly Trp Met
             20                  25                  30

Asp Phe Gly
         35

<210> SEQ ID NO 104
<211> LENGTH: 17
<212> TYPE: PRT
<213> ORGANISM: Homo sapiens

<400> SEQUENCE: 104

Gln Gly Pro Trp Leu Glu Glu Glu Glu Glu Ala Tyr Gly Trp Met Asp
 1               5                  10                  15

Phe
```

```
<210> SEQ ID NO 105
<211> LENGTH: 18
<212> TYPE: PRT
<213> ORGANISM: Homo sapiens

<400> SEQUENCE: 105

Gln Gly Pro Trp Leu Glu Glu Glu Glu Ala Tyr Gly Trp Met Asp
1               5                   10                  15

Phe Gly

<210> SEQ ID NO 106
<211> LENGTH: 6
<212> TYPE: PRT
<213> ORGANISM: Homo sapiens

<400> SEQUENCE: 106

Ser Ala Glu Asp Glu Asn
1               5
```

METHODS AND COMPOSITIONS FOR LIVER CANCER THERAPY

CROSS REFERENCE TO RELATED APPLICATIONS

This application claims the benefit under 35 USC § 119(e) of provisional application No. 61/367,851, filed Jul. 26, 2010 and of provisional application No. 61/476,204, filed Apr. 15, 2011, the contents of all of which are incorporated herein by reference in their entirety.

JOINT RESEARCH AGREEMENT

This application contains subject matter developed by, or on behalf of, one or more parties to a joint research agreement. The names of the parties to the joint research agreement are (1) BIOREALITES, S.A.S., (2) CENTRE NATIONAL DE LA RECHERCHE SCIENTIFIQUE (CNRS), (3) L'UNIVERSITE MONTPELLIER 2, and (4) INSTITUT NATIONAL DE LA SANTE ET DE LA RECHERCHE MEDICALE (INSERM).

REFERENCE TO SEQUENCE LISTING, TABLE OR COMPUTER PROGRAM

The instant application contains a Sequence Listing which has been submitted in ASCII format via EFS-Web and is hereby incorporated by reference in its entirety. Said ASCII copy, created on Jul. 14, 2011, is named BR (005US).txt and is 79,913 bytes in size.

FIELD OF INVENTION

The present disclosure is directed to, among other things, methods of treating subjects with liver cancer or at risk for liver cancer recurrence by administering to the subject a composition comprising an antibody specific for progastrin.

BACKGROUND

Liver cancer is the fifth most common cancer worldwide and the third most common cause of cancer-related death. Llovet et al., 2003, "Hepatocellular carcinoma," *Lancet* 362:1907-17. The most common form of liver cancer is hepatocellular carcinoma, also known as HCC, and often develops in the context of other underlying liver damage, typically hepatitis or cirrhosis. Thorgeirsson et al., 2002, "Molecular pathogenesis of human hepatocellular carcinoma," *Nature Genetics* 31:339-346. Other, less common, forms of liver cancer include hepatoblastoma and cholangiocarcinoma.

Standard treatment for liver cancer is surgical resection, whenever possible, and chemotherapy, chemoembolisation, or radiation therapy where surgery is not an option. Surgery is not always an option due to tumor size or location, advanced cirrhosis, and even with surgery, tumor recurrence/relapse complicates 70% of cases at 5 years post-resection. See Llovet et al., supra. Chemotherapeutic treatments also appear to have reduced efficacy in liver cancer, possibly due to increased ability of liver cancer cells to efflux chemotherapeutic agents. Thus, there is a significant and urgent need for more effective treatments of liver cancer.

SUMMARY

Gastrin is a gut peptide hormone that stimulates secretion of gastric acid. In adult mammals, it is produced principally by G cells in the gastric antrum, and to some extent in the upper small intestine and pancreas. Referring to FIG. 1, the gastrin gene is translated into a 101-amino acid polypeptide, called "preprogastrin" which contains a signal sequence (underlined) that is cleaved, giving rise to progastrin ("PG"), an 80-amino acid residue polypeptide. Gastrin, which is found primarily in three forms, G34, G17 and G14 (not illustrated), results from progastrin processing.

The presence of incompletely processed forms of gastrin, including PG, in some liver cancer tissue samples has been reported (see, e.g., Caplin et al., 1999, "Expression and processing of gastrin in hepatocellular carcinoma, fibrolamellar carcinoma and choangiocarcinoma," *J. Hepatol.* 30:519-526). It has now been discovered that anti-progastrin approaches can be used to monitor, treat, and prevent liver cancer and/or its recurrence. As demonstrated for the first time herein, gastrin mRNA is elevated in liver cancer stem cells and the ability of liver cancer cells, or isolated liver cancer stem cells, to form cancer spheres or spheroids under low adherence growth conditions is significantly reduced by anti-progastrin antibodies. While not intending to be bound by any theory of operation, anti-progastrin antibodies with the ability to bind progastrin ("PG") and neutralize PG's biological activity are believed to interfere with the growth of liver cancer cells, especially liver tumor-initiating, or cancer stem, cells. This is thought to reduce liver cancer tumor size and number, and to prevent recurrence of liver cancer. These discoveries provide new tools for the treatment, prevention, and monitoring of treatment of liver cancer.

Accordingly, in one aspect, the present disclosure provides methods and compositions useful for treating liver cancer and preventing recurrence of liver cancer in animals, including humans. As described in greater detail below, the methods of treatment involve administering to a subject diagnosed with liver cancer an amount of an antibody that specifically binds progastrin ("anti-PG antibody") effective to provide a therapeutic benefit. The anti-PG antibody may be administered alone, as monotherapy, or in conjunction with, or adjunctive to, other treatment modalities, such as tumor resection, radiation therapy, chemotherapy, therapy with another antibody, etc.

When used in conjunction with, or adjunctive to, tumor resection, the anti-PG antibody may be administered before and/or after removal of the tumor, and may be continued for a specific period of time following tumor removal, until a plasma and/or serum progastrin level below a specified threshold level is achieved, or until a decrease in plasma and/or serum progastrin levels over a specified period of time is achieved.

When used in conjunction with, or adjunctive to, chemotherapy, the anti-PG antibody may be administered prior to chemotherapy, concomitant with chemotherapy, or after chemotherapy. Again, the anti-PG antibody may be administered for a specified period of time, until a plasma and/or serum progastrin level below a specified threshold level is achieved, or until a decrease in plasma and/or serum progastrin levels or a specified period of time is achieved.

Compositions of the present disclosure contain at least one anti-PG antibody that specifically binds PG and neutralizes its biological activity. Any anti-PG antibody may be used in the methods of the present disclosure, including but not limited to, polyclonal and monoclonal anti-PG antibodies. Anti-PG antibodies useful for use in the methods of treatment and prevention disclosed herein include those described below in Section 7.11. Preferably, the anti-PG antibody is specific to the PG of the species being treated. For example, an anti-human PG antibody is administered to a human subject.

Anti-PG compositions suitable for use in the methods of the present disclosure may comprise a pharmaceutically acceptable carrier, excipient, and/or diluent. Compositions can be formulated for various routes of administration as described herein, and include carriers, excipients, and/or diluents suitable for the chosen route. For treatment purposes, anti-PG antibodies can be packaged in unit doses for ease use. Unit doses can be packaged into kits, containing a diluent and, optionally, instructions for use.

In another aspect, the present disclosure provides a method of monitoring the efficacy of anti-PG treatment, by measuring a concentration, or level, or PG in a blood (serum, plasma, or whole blood) sample from an individual with liver cancer treated with an anti-PG composition, and comparing the measured PG level to a baseline level of PG. The baseline can be a PG level in a blood sample from an earlier timepoint, for example, at the start of the treatment. The measurement that is compared to the baseline level can be from a sample taken during or after a course of treatment. A measured PG level below the baseline level is indicative of treatment efficacy and a measured PG level at or above that of the baseline level is indicative of a lack of efficacy.

BRIEF DESCRIPTION OF THE FIGURES

FIG. 1 provides amino acid sequences of human preprogastrin (SEQ ID NO:100), where the signal peptide sequence is underlined, mature human progastrin (SEQ ID NO:20) and certain products of progastrin processing, including G34 (SEQ ID NO:102), G34-Gly (SEQ ID NO:103), G17 (SEQ ID NO:104), G17-Gly (SEQ ID NO:105) and CTFP (SEQ ID NO:106).

FIG. 2. provides polynucleotide and amino acid sequences of variable light and variable heavy chains of certain exemplary murine anti-hPG monoclonal antibodies. In each case, the three CDRs are shown in bolded-underlined text. Specifically:

FIG. 2A provides the polypeptide sequence of the $V_H$ chain of murine anti-hPG MAb3 (SEQ ID NO:12) and a polynucleotide sequence encoding it (SEQ ID NO:16);

FIG. 2B provides the polypeptide sequence of the $V_L$ chain of murine anti-hPG MAb3 (SEQ ID NO:13) and a polynucleotide sequence encoding it (SEQ ID NO:17);

FIG. 2C provides the polypeptide sequence of the $V_H$ chain of murine anti-hPG MAb4 (SEQ ID NO:14) and a polynucleotide sequence encoding it (SEQ ID NO:18);

FIG. 2D provides the polypeptide sequence of the $V_L$ chain of murine anti-hPG MAb4 (SEQ ID NO:15) and a polynucleotide sequence encoding it (SEQ ID NO:19);

FIG. 2E provides the polypeptide sequence of the $V_H$ chain of murine anti-hPG MAb8 (SEQ ID NO:59) and a polynucleotide sequence encoding it (SEQ ID NO:67);

FIG. 2F provides the polypeptide sequence of the $V_L$ chain of murine anti-hPG MAb8 (SEQ ID NO:63) and a polynucleotide sequence encoding it (SEQ ID NO:71);

FIG. 2G provides the polypeptide sequence of the $V_H$ chain of murine anti-hPG MAb13 (SEQ ID NO:60) and a polynucleotide sequence encoding it (SEQ ID NO:68);

FIG. 2H provides the polypeptide sequence of the $V_L$ chain of murine anti-hPG MAb13 (SEQ ID NO:64) and a polynucleotide sequence encoding it (SEQ ID NO:72);

FIG. 2I provides the polypeptide sequence of the $V_H$ chain of murine anti-hPG MAb16 (SEQ ID NO:61) and a polynucleotide sequence encoding it (SEQ ID NO:69);

FIG. 2J provides the polypeptide sequence of the $V_L$ chain of murine anti-hPG MAb16 (SEQ ID NO:65) and a polynucleotide sequence encoding it (SEQ ID NO:73);

FIG. 2K provides the polypeptide sequence of the $V_H$ chain of murine anti-hPG MAb19 (SEQ ID NO:62) and a polynucleotide sequence encoding it (SEQ ID NO:70); and FIG. 2L provides the polypeptide sequence of the $V_L$ chain of murine anti-hPG MAb19 (SEQ ID NO:66) and a polynucleotide sequence encoding it (SEQ ID NO:74).

FIG. 3 provides projected polypeptide sequences for humanized variable heavy and light chains of selected anti-hPG monoclonal antibodies described herein. In each case, the three CDRs are shown in bolded-underlined text. Specifically:

FIG. 3A provides the projected amino acid sequence of the $V_H$ chain of humanized MAb3 (SEQ ID NO:21);

FIG. 3B provides the projected amino acid sequence of the $V_L$ chain of humanized MAb3 (SEQ ID NO:22);

FIG. 3C provides the projected amino acid sequence of the $V_H$ chain of humanized MAb4 (SEQ ID NO:23);

FIG. 3D provides the projected amino acid sequence of the $V_L$ chain of humanized MAb4 (SEQ ID NO:24);

FIG. 3E provides the projected amino acid sequence of the $V_H$ chain of humanized MAb8(a) (SEQ ID NO:75);

FIG. 3F provides the projected amino acid sequence of the $V_L$ chain of humanized MAb8(a) (SEQ ID NO:76);

FIG. 3G provides the projected amino acid sequence of the $V_H$ chain of humanized MAb8(b) (SEQ ID NO:77);

FIG. 3H provides the projected amino acid sequence of the $V_L$ chain of humanized MAb8(b) (SEQ ID NO:78);

FIG. 3I provides the projected amino acid sequence of the $V_H$ chain of humanized MAb8(c) (SEQ ID NO:79);

FIG. 3J provides the projected amino acid sequence of the $V_L$ chain of humanized MAb8(c) (SEQ ID NO:76);

FIG. 3K provides the projected amino acid sequence of the $V_H$ chain of humanized MAb13(a) (SEQ ID NO:80);

FIG. 3L provides the projected amino acid sequence of the $V_L$ chain of humanized MAb13(a) (SEQ ID NO:81);

FIG. 3M provides the projected amino acid sequence of the $V_H$ chain of humanized MAb13(b) (SEQ ID NO:82);

FIG. 3N provides the projected amino acid sequence of the $V_L$ chain of humanized MAb13(b) (SEQ ID NO:83);

FIG. 3O provides the projected amino acid sequence of the $V_H$ chain of humanized MAb16(a) (SEQ ID NO:84);

FIG. 3P provides the projected amino acid sequence of the $V_L$ chain of humanized MAb16(a) (SEQ ID NO:85);

FIG. 3Q provides the projected amino acid sequence of the $V_H$ chain of humanized MAb16(b) (SEQ ID NO:86);

FIG. 3R provides the projected amino acid sequence of the $V_L$ chain of humanized MAb16(b) (SEQ ID NO:87);

FIG. 3S provides the projected amino acid sequence of the $V_H$ chain of humanized MAb16(c) (SEQ ID NO:88);

FIG. 3T provides the projected amino acid sequence of the $V_L$ chain of humanized MAb16(c) (SEQ ID NO:89);

FIG. 3U provides the projected amino acid sequence of the $V_H$ chain of humanized MAb19(a) (SEQ ID NO:90);

FIG. 3V provides the projected amino acid sequence of the $V_L$ chain of humanized MAb19(a) (SEQ ID NO:91);

FIG. 3W provides the projected amino acid sequence of the $V_H$ chain of humanized MAb19(b) (SEQ ID NO:92);

FIG. 3X provides the projected amino acid sequence of the $V_L$ chain of humanized MAb19(b) (SEQ ID NO:93);

FIG. 3Y provides the projected amino acid sequence of the $V_H$ chain of humanized MAb19(c) (SEQ ID NO:94); and FIG. 3Z provides the projected amino acid sequence of the $V_L$ chain of humanized MAb19(c) (SEQ ID NO:95).

FIG. 5A-B provide bar charts of GAST mRNA levels in three liver cancer cell lines—PLC/PRF/5 (FIG. 5A), Huh6 (FIG. 5B) and Huh7 (FIG. 5B)—compared to levels observed in a colorectal cancer cell line, SW480, known to have elevated GAST expression.

FIG. 6A-B provide bar charts of GAST mRNA levels in Huh-6 (FIG. 6A) and Huh7 (FIG. 6B) "side population" (SP) cells compared to levels observed in an unselected pool of Huh6 or Huh7 cells, grown under low adherence culture conditions.

FIG. 7 provides a graph of the number of spheroid growths per well of PLC/PRL/5 cells grown under low adherence culture conditions, in the presence of an exemplary anti-PG monoclonal antibody or a control antibody.

FIG. 8 provides a graph of the number of spheroid growths per well of Huh6 "side population" (SP) cells grown under low adherence growth conditions in the presence of doxorubicin and dimethyl sulfoxide (DMSO), DMSO alone, an exemplary anti-PG polyclonal antibody, or a control polyclonal antibody.

FIG. 9 provides a graph of the number of spheroid growths per well of Huh7 "side population" cells grown under low adherence growth conditions in the presence of doxorubicin and DMSO, DMSO alone, an exemplary anti-PG polyclonal antibody or a control polyclonal antibody.

FIG. 10 provides a graph of the number of spheroid growths per well of Huh6 cells grown under low adherence growth conditions in media alone ("Control"), or with anti-hPG MAb 13, or anti-hPG MAb19.

FIG. 11 provides a bar chart of the median number of spheroid growths per well of Huh6 cells grown under low adherence growth conditions after growth under regular adherence conditions in media alone ("Control"), or with anti-hPG MAb 8, or anti-hPG MAb13.

FIG. 12A-B provide graphs of the number of spheroid growths per well of Huh7 cells grown under low adherence growth conditions. FIG. 12A shows cells grown in media alone ("Control") versus cells treated with anti-hPG MAb 13. FIG. 12B shows cells treated with one of: a control monoclonal antibody ("Control MAb"), anti-hPG MAb 13, and anti-hPG MAb16.

FIG. 13A-B provide graphs of the number of spheroid growths per well of Huh7 cells grown under low adherence growth conditions after growth under regular adherence conditions with either anti-hPG MAb 8 (FIG. 13A) or anti-hPG MAb 16 (FIG. 13B) as compared to a control monoclonal antibody ("Control MAb").

FIG. 14 provides a graph of the number of spheroid growths per well of Huh7 "side population" cells grown under low adherence growth conditions with media alone ("Control"), or with anti-hPG MAb 8 or anti-hPG MAb13.

FIG. 15A-C provide graphs of the number of spheroid growths per well of PLC/PRL/5 cells treated with anti-hPG MAb 19 (FIG. 15A), anti-hPG MAb 13 (FIG. 15B), or anti-hPG MAb 8 and MAb 13 (FIG. 15C), as compared to a control monoclonal antibody ("Control MAb").

FIG. 16 provides a graph of the number of spheroid growths per well of PLC/PRL/5 cells grown under low adherence growth conditions after growth under regular adherence conditions with one of: a control monoclonal antibody ("CT MAb"), anti-hPG MAb 8, or anti-hPG MAb16.

FIG. 17 provides a graph of the number of spheroid growths per well of PLC/PRL/5 "side population" cells grown under low adherence growth conditions in media alone ("Control") or with anti-hPG MAb13, or anti-hPG MAb16.

DETAILED DESCRIPTION

7.1. Liver Cancer

Figure 4:
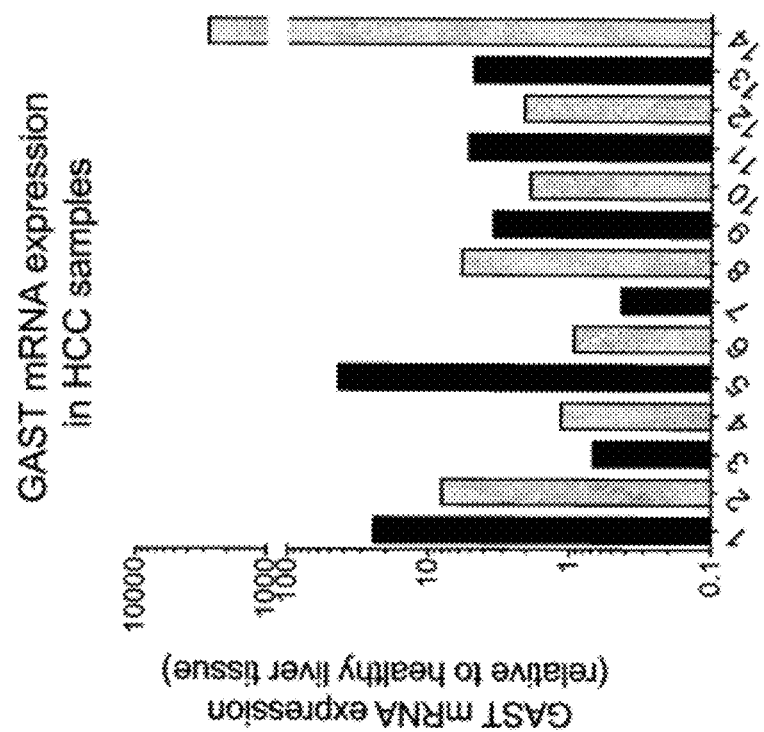
FIG. 4 provides a bar chart of GAST mRNA levels in tumors relative to the average level detected in healthy liver tissue collected from 14 individuals with liver cancer (HCC).

Liver cancer includes hepatocellular carcinoma (HCC), cholangiocarcinoma and hepatoblastoma. Most liver cancers are HCC and often arise in individuals suffering from other underlying liver pathologies, including hepatitis, cirrhosis, and/or aflatoxin B1 poisoning, which cause liver inflammation and chronic injury and regeneration of liver cells. Diagnosis of liver cancer is currently based on a combination of ultrasonography, fine-needle biopsy, and detection of circulating levels of certain marker proteins, including, for example, alpha-fetoprotein. HCC can be classified into early, intermediate, advanced, and end-stage cancer based on tumor size, number and morphology (e.g. encapsulated or invasive), and liver function.

Current treatments for liver cancer include liver transplant, surgical resection, percutaneous ablation, chemotherapy, including chemoembolisation, radiation treatment, antibody treatment. Liver transplant, while completely curative, is not available to most patients because of the stage of their disease and/or the lack of available organs for transplant. The availability of transplants may also be limited for patients infected with the hepatitis B or C viruses, as well as patients suffering from alcoholism. Surgical resection and percutaneous ablation, procedures that remove or kill the cancer tissue, can have good outcomes but are not available to all patients. Tumor location or size can preclude surgical resection, as can cirrhosis or other impairment of liver function, due to the risk of organ failure attendant to the procedure. Even for liver resection, tumor recurrence complicates 70% of cases within 5 years. Percutaneous ablation destroys neoplastic cells and is suited to individuals with one tumor smaller than 3 cm who are not candidates for surgical resection. In individuals whose cancer is more advanced or where liver function is impaired, the standard treatments are chemotherapy and radiation therapy, with or without embolisation (occlusion of an artery to cut off blood supply to, and induce death of, the tumor). Currently available treatments are inadequate to address the need for effective therapy that can be used to treat the majority of individuals affected by liver cancer.

7.2. Liver Cancer Recurrence

Recurrence is especially problematic in liver cancer. A cancer recurrence is generally understood as a return of cancer after treatment and after a period of time during which the earlier cancer cannot be detected. Various explanations have been offered for the high rate of liver cancer recurrence, including failure to remove all cancer cells during surgical procedures, spreading of cancer cells by the instruments during percutaneous ablation, and resistance to chemotherapeutic agents. There is a need for liver cancer therapies that reduce or eliminate recurrence.

7.3. Cancer Stem Cells

Solid tumors are not necessarily homogenous tissues. Rather, some tumors comprise a plurality of aberrant cell types having distinct phenotypic and functional properties. In this respect, such tumors are analogous to abnormal organs. Cells comprising solid tumors differ with respect to the extent to which they are capable of initiating formation of a new tumor when transplanted to a new site in the same host, or to a new host of the same or different species. Cells having this property are known as tumor or cancer initiating cells, or alternatively, tumor or cancer stem cells. See, e.g., Chiba et al., 2009, "Cancer stem cells in hepatocellular carcinoma: Recent progress and perspective," Cancer Letters 286:145-153. Such cells form tumors when transplanted into immunodeficient mice in much smaller numbers than the numbers required for an unselected pool of liver cancer cells to form tumors on such mice (1000 "side population" liver cancer cells versus 1 million unsorted liver cancer cells). See Chiba et al., supra.

Generally, cancer stem cells are defined by two properties: the ability to self-renew and the ability to give rise to daughter cells that differentiate into non-stem cells. Self-renewal is the ability to undergo cell division whereby one or both daughter cells remain undifferentiated, retaining the ability to give rise to yet another cancer stem cell with similar capacity to proliferate as the parental cell. This property allows cancer stem cells to ultimately give rise to the great number cells that comprise the growing tumor. Cancer stem cells also have the ability to produce daughter cells that differentiate, giving rise to a spectrum of more differentiated non-stem, or bulk, tumor cells found in many solid tumors. Thus, when transplanted, cancer stem cells can reconstitute the type of tumor from which they originated, even after multiple, serial transplantations. Furthermore, it is thought that cancer stem cells harbor genetic mutations and/or epigenetic changes that result in altered proliferation patterns and/or low rates of apoptosis.

Cancer stem cells can be identified according to a number of phenotypic characteristics that distinguish them from bulk tumor cells. First, as noted above, liver cancer stem cells have the ability to initiate a new tumor when transplanted into a new host. By contrast, bulk tumor cells are either unable to initiate new tumors, or require many more cells than cancer stem cells to form a new tumor. See Chiba et al., 2009, "Cancer stem cells in hepatocellular carcinoma: Recent progress and perspective," Cancer Letters 286:145-153.

Methods useful for assessing whether a tumor or cell line contains cancer stem cells are familiar to those of skill in the art. As a non-limiting example, a tumor, or portion thereof suspected of containing cancer stem cells, is isolated, such as by surgical resection. Thereafter the tumor tissue is minced and treated with enzymes, or some other treatment, effective to disaggregate the tumor and release its constituent cells. Alternatively, where a cell line is under analysis, it may only be necessary to disassociate the cells with enzymatic or chemical treatment. Or, sub-population of cells may be prepared, selected on the basis of one or more of the phenotypes described herein, such as the presence or absence of marker proteins or the ability to exclude dyes or other substances. Cell populations lacking the marker profile(s), dye exclusion, or other property associated with cancer stem cells can be prepared as a control.

After isolating the relevant cell subpopulations, predetermined numbers of such cells are then implanted into one or more target tissues or organs in a recipient animal. In some embodiments, the recipient animal is an immunodeficient mouse, including but not limited to nude mice, mice with severe combined immunodeficiency (SCID), and nonobese-diabetic SCID (NOD-SCID) mice. Other species can also be used, according to the knowledge of the ordinarily skilled artisan.

Cells can be implanted subcutaneously, or into the liver. Cells can be implanted into other tissues and organs, as well. In some embodiments, the target tissue or organ is chosen to replicate the tissue or organ of origin of the tumor under analysis. However, in other embodiments, distinct tissues or organs are chosen in which to host the implanted cells.

After cells are implanted using techniques familiar to those of ordinary skill, left undisturbed for a period of time, animals can be assessed to determine whether a new tumor has grown at the site of implantation. For cells implanted subcutaneously, tumor growth can be assessed by visual examination and palpation of the site of implantation. If a tumor is detectable, its size can be measured through time using calipers. For cells implanted into an internal organ, the animal may be sacrificed at a predetermined time post-implantation to determine if one or more tumor is present, and if so, the number and size of such tumor(s). Alternatively, according to the knowledge of the ordinary skilled artisan, non-invasive techniques can be used to assess tumor growth.

Second, cancer stem cells are also identifiable by their expression or non-expression of certain markers, whereas bulk tumor cells from the same tumor have different patterns of marker expression. In some embodiments, the absence of expression of a marker is indicative of the cancer stem cell phenotype. Such markers include proteins expressed within the cell, or on the cell surface, and can be detected using a variety of techniques, including, but not limited to, immunohistochemistry, immunofluorescence, and FACS analysis. Liver cancer stem cells have been identified by cell surface markers. Liver cancer cells bearing one or more cell surface marker, including CD133, CD90, and CD44, appear to have increased tumor initiating properties, and have been characterized as liver cancer stem cells.

Third, liver cancer stem cells have also been identified by their ability to efflux dyes and drugs via protein transporters. Tumor-initiating liver cancer cells have been identified based on the ability to exclude Hoechst 33342 dye via an ABC transporter. Such cells can be identified by exposing them to the fluorescent dye and using FACS analysis to separate cells that take up such dyes from those that exclude them. These dye-excluding cancer cells are referred to as side population (SP) cells. SP cells can initiate tumors from as few as 1000 cells (Chiba et al., 2006 "Side-population purified from hepatocellular carcinoma cells harbors cancer stem cell-like properties" Hepatology 44: 240-251). Other techniques for detecting liver cancer stem cells are also possible, according to the knowledge of those ordinarily skilled in the art.

In addition to the ability to initiate tumors in vivo, where bulk tumor cells are either incapable or have significantly less ability to do so, cancer stem cells also exhibit an increased ability to grow under serum-free low-adherence culture conditions, as compared to bulk tumor cells and can, depending on the type of cancer, form so-called spheroids under low-adherence culture conditions. Spheroids are compacted balls of cells that form as certain cells grow in culture after being seeded as disaggregated suspensions. The formation of such spheroids is promoted when the cells are grown in serum-free medium, generally in the presence of specific growth factors (including, but not limited to, Epidermal Growth Factor (EGF) and basic Fibroblast Growth Factor (bFGF)), and in tissue culture dishes having surfaces to which mammalian cells poorly adhere. Similar to stem cells from normal tissues, it has been discovered that cancer stem cells preferentially grow as spheroids under the appropriate culture conditions. See, e.g., Rappa, G., et al., Exp. Cell Res., 314:2110 (2008); Singh, S. K., et al., Cancer Res., 63:5821 (2003); Fang, D., et al., Cancer Res., 65:9328 (2005). Assays for spheroid growth under low adherence culture conditions, or spheroid growth conditions, are described in the Examples below and are also within the knowledge of those skilled in the art.

7.4. Role of Cancer Stem Cells in Liver Cancer Recurrence

Tumor cells with properties of cancer stem cells have been identified that exhibit enhanced resistance to radiation and/or chemotherapeutic agents. Eyler, C. E., et al., 2008, *J. Clin. Oncol.*, 26:2839-2845. The increased resistance of cancer stem cells to radiation and chemotherapy not only reduces the efficacy of such therapies but may also allow such cells to persist even after tumors are no longer detectable and the therapy has been successful. In such patients, treatment is initially effective, causing the tumors to shrink or disappear in diagnostic scans, but the tumors reappear some time after treatment ceases. This, in turn, could explain the phenomenon of recurrence in individuals previously treated for liver cancer. Eyler, supra Inhibiting growth of, or killing, liver cancer stem cells in a subject who has previously been treated for liver cancer, where there is no present sign of liver cancer, may therefore prevent a recurrence.

7.5. Anti-PG Antibodies and their Effect on Liver Cancer Stem Cells

As shown in the Examples below, liver cancer tumors and HCC cell lines show increased expression of the gastrin gene (GAST) which encodes progastrin. This expression is even further elevated in "side population" cells—which bear the characteristics of liver cancer stem cells—in two different liver cancer cells lines. While not intending to be bound by any theory of operation, it is thought that one way to treat liver cancer, initial or recurring, is to administer an agent that inhibits the growth of liver cancer stem cells, and preferably inhibits the ability of tumor initiating cells to form tumors.

Applicants have discovered that anti-progastrin antibodies are such agents. As disclosed herein, it was surprisingly discovered that the growth of liver cancer stem cells can be inhibited by treatment with antibodies that specifically recognize human progastrin ("hPG"). Based on these surprising results, it is expected that administering a therapeutically effective amount of anti-hPG antibodies to a patient having cancer containing liver cancer stem cells would have therapeutic benefit by, for example, but not by way of limitation, reducing the ability of such cells to contribute to liver cancer or its recurrence.

It is believed that the anti-PG antibodies of the present disclosure are effective to inhibit the growth of liver cancer stem cells, by binding to progastrin, thereby preventing it from interacting with its putative receptor or receptors, even if unknown, on cancer stem cells. Progastrin, whether produced by the cancer stem cells themselves, or by healthy tissues, is therefore prohibited from mediating its growth promoting biological effects on such cells. As a consequence, it is thought that neutralizing PG, as anti-PG antibodies of the present disclosure do, blocks PG's interaction with its receptor or receptors on such cells and may causes the cells to die, possibly as a result of apoptosis, and/or to stop or slow cellular division. Other mechanisms by which anti-PG antibodies interfere with the survival and/or growth of cancer stem cells are also possible, and are not intended to limit the scope of the inventions disclosed herein. The ability of an anti-PG antibody to neutralize PG's activity can be determined using assays known to the person of skill, including in vitro cell growth inhibition assays such as those described in the Examples below.

7.6. Methods of Treating Liver Cancer

The present disclosure provides methods of treating liver cancer in a subject by administering an effective amount of an anti-progastrin ("anti-PG") antibody, having a therapeutic benefit. The methods of treating liver cancer according to the present disclosure are accomplished by administering one or more anti-PG antibody capable of neutralizing PG, described in detail below at Section 7.11, to individuals with liver cancer. Any antibody that neutralizes PG may be used in the methods of the present disclosure, including, but not limited to, polyclonal and monoclonal (e.g., chimeric, humanized, fully human, full-length, Fab, single-chain) anti-PG antibodies. Suitable anti-PG antibodies are capable of inhibiting the growth of liver cancer cells in vitro. In some embodiments, the anti-PG antibodies are capable of inhibiting the growth of spheroids under low adherence culture conditions by liver cancer cells with tumor-initiating properties, including liver cancer stem cells, liver cancer cells bearing one or more cell surface markers selected from the group consisting of CD133, CD44, and CD90, and liver cancer cells capable of exporting Hoechst 33342 dye.

Subjects in need of treatment for liver cancer are individuals diagnosed with liver cancer. The liver cancer can be a first occurrence or a recurrence. Suitable subjects include individuals with elevated blood concentration of PG, individuals whose liver cancer is not treatable by other means, such as individuals with inoperable tumors or individuals in whom other types of therapy have failed, and individuals receiving other treatment for liver cancer, including surgical resection, chemotherapy, chemoembolization, radiation therapy, or antibody therapy with an antibody other than the anti-PG antibodies of the present disclosure. Suitable subjects also include individuals previously treated for liver cancer, who, after a period of remission, have recurring liver cancer. The liver cancer can be at any stage of progression. The subject can be a human or a non-human, including a domesticated or a non-domesticated animal.

Anti-PG treatment can be administered alone, as monotherapy, or in combination with, or adjunctive to, one or more other treatments for liver cancer. Other treatments include, without limitation, surgical resection, and treatment with a second therapeutic agent, such as a chemotherapeutic agent, an irradiating agent, or an antibody, as described herein. Combination treatment as provided herein involves the administration of at least two treatments to a patient, one of which is anti-PG treatment with at least one anti-PG antibody, and the other of which is treatment with a therapeutic agent or procedure.

Anti-PG treatment can be combined with surgical procedures, such as surgical resection or percutaneous ablation. Anti-PG antibodies can be administered to subjects with primary or recurrent liver cancer, in combination with surgical resection or percutaneous ablation of the affected portion(s) of the liver. Anti-PG treatment can be initiated before, concurrently with, or after surgical resection.

Anti-PG treatment can be combined with radiation therapy. Radiation therapy is the use of high-energy radiation from x-rays, gamma rays, neutrons, protons, and other sources to kill cancer cells and shrink tumors. Radiation may come from a machine outside the body (external-beam radiation therapy), or it may come from radioactive material placed in the body near cancer cells (internal radiation therapy, or brachytherapy). For example, liver cancer has been treated by internal radiation with $^{131}$I. Systemic radiation therapy uses a radioactive substance, such as a radiolabeled monoclonal antibody, that travels in the blood to tissues throughout the body. Radiation therapy may also be called irradiation and radiotherapy. Other radiation therapies include three-dimensional conformal radiation therapy (3D-

CRT) and intensity modulated radiation therapy (IMRT). Other radiation therapies are also possible.

Anti-PG antibody treatment can also be combined with a chemotherapeutic agent. Chemotherapy is the use of small molecule drugs that kill (cytotoxic or cytocidal) or prevent the growth (cytostatic) of cancer cells. For liver cancer, chemotherapeutic agents are often combined with embolisation treatments, such as, for example, the combination of gelatin for embolisation and doxorubicin, mitomycin, or cisplatin as chemotherapeutic agents. Chemotherapeutic agents include, but are not limited to, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, oxaliplatin, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, sorafenib, streptozotocin, tamoxifen, taxol, tegafur, teniposide, tenoposide, testolactone, tetracaine, thiotepa chlorambucil, thioguanine, thiotepa, topotecan HCL, toremifene citrate, trastuzumab, tretinoin, valrubicin, vinblastine sulfate, vincristine sulfate, and vinorelbine tartrate.

Anti-PG antibodies can also be administered with a combination of chemotherapeutic agents. Exemplary combinations of chemotherapeutic agents include 5-fluorouracil (5FU) in combination with leucovorin (folinic acid or LV); capecitabine, in combination with uracil (UFT) and leucovorin; tegafur in combination with uracil (UFT) and leucovorin; oxaliplatin in combination with 5FU, or in combination with capecitabine; irinotecan in combination with capecitabine, mitomycin C in combination with 5FU, irinotecan or capecitabine. Use of other combinations of chemotherapeutic agents disclosed herein is also possible.

Standard dosing regimens for chemotherapeutic agents used for patients who have liver cancer may be used in the methods of the present disclosure. As is known in the relevant art, chemotherapy regimes for liver cancer using combinations of different chemotherapeutic agents have been standardized in clinical trials. See Llovet et al., supra, for a summary of clinical trials using chemotherapeutic agents.

Anti-PG antibodies can also be used in combination with other antibodies, including but not limited to, monoclonal antibodies that directly or indirectly kill, slow or stop the growth of cancer cells. Such antibodies can function through a variety of distinct mechanisms. For example, certain antibodies can mark cancer cells for attack by the patient's immune system via antibody-dependent cell-mediated cytotoxicity (ADCC) or other mechanisms. It is believed that rituximab (Rituxan®), which binds the CD20 antigen found on B cells, and edrecolomab, which binds the 17-1A antigen, can function this way. Other antibodies bind to and alter or inhibit the function of antigens that cancer cells require for survival or growth. A number of antibodies are believed to function this way, including, for example, cetuximab (Erbitux®) and panitumumab (Vectibix®), each of which binds to the EGF receptor (EGFR); and bevacizumab (Avastin®), which binds to the growth factor VEGF. Other mechanisms are also possible, and particular antibodies may be able to work via one or more mechanisms of action. Yet other antibodies can be conjugated to radioactive or chemotoxic moieties and target them to cancer cells which preferentially express antigens specifically recognized by the antibodies.

The anti-PG antibody and a second agent can be administered simultaneously, successively, or separately. As used herein, the anti-PG antibody and the second agent are said to be administered successively if they are administered to the patient on the same day, for example during the same patient visit. Successive administration can occur 1, 2, 3, 4, 5, 6, 7 or 8 hours apart. In contrast, the anti-PG antibody and the second agent are said to be administered separately if they are administered to the patient on different days, for example, the anti-PG antibody and the second therapeutic agent can be administered at a 1-day, 2-day or 3-day, one-week, 2-week or monthly intervals. In the methods of the present disclosure, administration of the anti-PG antibody of the disclosure can precede or follow administration of the second agent. As a non-limiting example, the anti-PG antibody and second agent can be administered concurrently for a period of time, followed by a second period of time in which the administration of anti-PG antibody and the second agent are alternated.

7.7. Methods of Preventing Liver Cancer Recurrence

In another aspect, the present disclosure provides a method of preventing liver cancer recurrence, comprising administering an effective amount of an anti-PG antibody to a subject in need of prevention. Methods of preventing liver cancer recurrence according to the present disclosure are accomplished by administering one or more anti-PG antibody capable of neutralizing PG, described in detail below at Section 7.11, to individuals at risk for liver cancer recurrence.

Subjects in need of prevention of liver cancer recurrence are individuals previously treated for liver cancer, who are at risk of, but have not, been diagnosed with liver cancer again. Suitable subjects include individuals previously treated for liver cancer by any means, including surgical resection, chemotherapy, or any other therapy.

Effective prevention of liver cancer recurrence includes, but is not limited to, a complete and ongoing absence of liver cancer recurrence. In some embodiments, effective prevention is measured by an absence of liver cancer tumors or liver cancer stem cells obtained from a subject at risk for liver cancer recurrence. In some embodiments, effective prevention is determined by a lack of increase in blood concentration of PG in a subject at risk for liver cancer recurrence.

Anti-PG treatment can be administered alone, as monotherapy, or in combination with, or adjunctive to, one or more other treatments. Other treatments include, without limitation, surgical resection, and treatment with a second therapeutic agent, such as a chemotherapeutic agent, an irradiating agent, or an antibody, as described herein. Combination treatment as provided herein involves the administration of at least two treatments to a patient, one of which is anti-PG treatment with at least one anti-PG antibody, and the other of which is treatment with a therapeutic agent or procedure.

The anti-PG antibody and a second agent can be administered simultaneously, successively, or separately. As used herein, the anti-PG antibody and the second agent are said to be administered successively if they are administered to the patient on the same day, for example during the same patient visit. Successive administration can occur 1, 2, 3, 4, 5, 6, 7 or 8 hours apart. In contrast, the anti-PG antibody and the second agent are said to be administered separately if they are administered to the patient on different days, for example, the anti-PG antibody and the second therapeutic agent can be administered at a 1-day, 2-day or 3-day, one-week, 2-week or monthly intervals. In the methods of the present disclosure, administration of the anti-PG antibody of the disclosure can precede or follow administration of the second agent. As a non-limiting example, the anti-PG antibody and second agent can be administered concurrently for a period of time, followed by a second period of time in which the administration of anti-PG antibody and the second agent are alternated.

7.8. Pharmaceutical Compositions

Anti-PG antibodies useful in the methods of the present disclosure can be formulated in compositions. Optionally, the compositions can comprise one or more additional agent(s), such as the second agents described above. The compositions will usually be supplied as part of a pharmaceutical composition, which is sterile and will normally include a pharmaceutically acceptable carrier. This pharmaceutical composition can be in any suitable form (depending upon the desired method of administering it to an individual).

Anti-PG antibodies can be administered to an individual by a variety of routes such as orally, transdermally, subcutaneously, intranasally, intravenously, intra-arterially, intramuscularly, intraocularly, topically, intrathecally and intracerebroventricularly. The most suitable route for administration in any given case will depend on the particular antibody, the subject, and the nature and severity of the disease and the physical condition of the subject. Antibodies can be formulated as an aqueous solution and administered by subcutaneous injection. Pharmaceutically acceptable carriers for use in the disclosure can take a wide variety of forms depending, e.g., on the condition to be treated or route of administration.

Pharmaceutical compositions can be conveniently presented in unit dose forms containing a predetermined amount of an anti-PG antibody per dose. Such a unit can contain for example 5 mg to 5 g, for example 10 mg to 1 g, or 20 to 50 mg of anti-PG antibody per unit dose. Pharmaceutical compositions can comprise anti-PG antibodies capable of binding more than one PG epitope. Alternatively, pharmaceutical compositions may comprise a combination of anti-PG antibodies, each capable of binding a different PG epitope.

Pharmaceutical compositions of the disclosure can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, e.g., Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188, etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, for example about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

Anti-PG antibodies can be administered singly, as mixtures of one or more anti-PG antibodies, in mixture or combination with other agents useful in treating liver cancer. Examples of suitable combination and adjunctive therapies are provided above.

7.9. Effective Dosages

The anti-PG antibodies of the present disclosure, or compositions thereof, will generally be used in an amount effective to achieve the intended result, for example an amount effective to treat liver cancer in a subject with liver cancer, or an amount effective to prevent recurrence in a subject at risk for liver cancer recurrence. An effective amount is an amount that confers a therapeutic benefit.

In the context of methods of treating liver cancer, a therapeutic benefit means any tendency to partially or completely treat liver cancer. Therapeutic benefit may be evidenced by any of the following, alone or in combination: reducing the size, number, or morphology (e.g. encapsulated versus invasive) of liver tumors; eliminating liver tumors; reducing in the severity of the liver cancer; inducing remission of the liver cancer; halting or delaying aggravation of the symptoms or signs associated with liver cancer; increasing patient comfort, reducing patient pain; reducing or eliminating the number of side population cells, liver cancer cells bearing one or more cell surface markers CD133, CD44, or CD90, or liver cancer stem cells; reducing blood concentration of PG in a subject with liver cancer. Tumor size, number and metabolism can be measured using various scanning techniques, such as, but not limited to, CT, MRI, functional MRI, SPECT and PET, as well as other methods known to those of ordinary skill in the art. A complete cure, while desirable, is not required for therapeutic benefit to exist.

In the context of preventing liver cancer recurrence, a therapeutic benefit means any tendency to partially of completely prevent the reappearance or regrowth of cancer in a subject some time after cancer has become undetectable. Therapeutic benefit may be evidenced by any of the following alone, or in combination: maintaining remission from liver cancer; increasing a subject's life expectancy; delaying the growth of liver tumors; inhibiting the growth of liver cancer stem cells, side population cells, or liver cancer cells bearing one or more cell surface markers CD133, CD44, or CD90; reducing or eliminating the number of side population cells, liver cancer cells bearing one or more cell surface markers CD133, CD44, or CD90, or liver cancer stem cells.

In some contexts, therapeutic benefit can be correlated with one or more surrogate end points, in accordance with the knowledge of one of ordinary skill in the art. By way of example and not limitation, plasma and/or serum PG concentrations can be measured in a subject over time, with a reduction in PG levels, or a level below a threshold level, for example, below about 50 pM, 40 pM, 30 pM, 20 pM, 10 pM or 5 pM, being indicative of therapeutic benefit.

In other embodiments, therapeutic benefit of an anti-PG antibody composition can be determined by its capability of killing cancer stem cells, inhibiting cancer stem cell growth or proliferation, or increasing cancer stem cell apoptosis. As discussed elsewhere in this disclosure, liver cancer stem cells can be identified as having one or more phenotypic characteristics associated with cancer stem cells, including, but not limited to, expression of certain cell markers, ability to grow as spheroids under low adherence culture conditions, and the ability to initiate new tumor growth after transplantation.

Binding all free PG is not required to achieve therapeutic efficacy. Free PG means PG that is available to be bound by an anti-PG antibody. Rather, reducing the concentration of free PG within a tumor, systemically, in particular body fluids, or elsewhere, to a more limited extent may also be effective. Exemplary tissues and body fluids in which free PG concentration may be reduced by administration of the anti-PG antibody compositions described herein include, but are not limited to, cancer biopsy removed from a patient, ascites fluid, fluid from pleural effusions, cerebrospinal fluid, lymph, blood, plasma, serum and others. The concentration of PG in one or more of these tissues or body fluids can be quantified using an ELISA technique or other techniques familiar to those of ordinary skill in the art.

In accordance with the knowledge of those ordinarily skilled in the art, the dose of an anti-PG antibody can be titrated in a patient so as to reduce the free PG concentration in a tissue or body fluid of interest at a predetermined time after administration at least about 10%, 20%, 30%, 40%, 50%, 60%, 70%, 80%, 90, or 100%, or about 5%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, or about 90%-95%, or a percentage reduction in free PG concentration ranging between any of the foregoing values.

Compositions comprising anti-PG antibodies can be administered to individuals (e.g., human subjects) at effective dosages. The amount of anti-PG antibody administered will depend on a variety of factors, including the size and weight of patients to be treated, the form, route and site of administration, the treatment regimen (e.g., whether a second therapeutic agent is used), the age and condition of the particular subject being treated, the sensitivity of the individual to anti-PG antibodies. The appropriate dosage can be readily determined by a person skilled in the art. Ultimately, a physician will determine appropriate dosages to be used. This dosage can be repeated as often as appropriate. If side effects develop the amount and/or frequency of the dosage can be altered or reduced, in accordance with normal clinical practice. The proper dosage and treatment regimen can be established by monitoring the progress of treatment using conventional techniques known to the people skilled of the art.

Effective dosages can be estimated initially from in vitro assays. For example, an initial dose for use in animals may be formulated to achieve a circulating blood or serum concentration of anti-PG antibody that is at or above the binding affinity of the antibody for progastrin as measured in vitro. Calculating dosages to achieve such circulating blood or serum concentrations taking into account the bioavailability of the particular antibody is well within the capabilities of skilled artisans. For guidance, the reader is referred to Fingl & Woodbury, "General Principles" in *Goodman and Gilman's The Pharmaceutical Basis of Therapeutics*, Chapter 1, latest edition, Pagamonon Press, and the references cited therein.

Initial dosages can be estimated from in vivo data, such as from animal models. Animal models useful for testing the efficacy and safety of compounds to treat liver cancer are known in the art, such as, but not limited to, xenografts of human hepatocellular carcinoma cells in mice or other animals. Ordinarily skilled artisans can routinely adapt such information to determine dosages suitable for human administration.

In specific embodiments, an intravenous dose may be determined for an individual subject by measuring the serum or plasma PG concentration of the individual a few times a few days to a few weeks prior to treatment and calculating an amount of anti-PG antibody that would be saturating, i.e., an amount that would be sufficient to bind all of the PG. As will be appreciated by skilled artisans, the amount of any specific antibody necessary to achieve saturation for a given serum or plasma concentration of PG will depend, in part, on the affinity constant of the particular antibody. Methods for calculating saturating quantities for specific anti-PG antibodies of interest are well-known.

To insure saturation, an amount that is greater than the calculated saturating amount may be administered, for example, at least 2-, 3-, 4-, 5-, 6-, 7-, 8-, 9- or even 10-fold greater than the calculated saturating amount may be administered. For modes of administration other than i.v., the amount can be adjusted based upon pharmacokinetic and bioavailability, as is well known in the art.

The effective dose of an anti-PG antibody of the disclosure can range from about 0.001 to about 250 mg/kg per single (e.g., bolus) administration, multiple administrations or continuous (e.g., infusion) administration, or to achieve a serum concentration of 0.01-5000 µg/ml serum concentration per single administration, multiple administrations or continuous administration, or any effective range or value therein depending on the condition being treated, the route of administration and the age, weight and condition of the subject. In certain embodiments, each dose can range from about 0.1 mg/kg to about 0.5 mg/kg; about 0.25 mg/kg to about 0.75 mg/kg; about 0.5 mg/kg to about 1 mg/kg; about 1 mg/kg to about 2 mg/kg; about 1.5 mg/kg to about 2.5 mg/kg; about 2 mg/kg to about 3 mg/kg; about 2.5 mg/kg to about 3.5 mg/kg; about 3 mg/kg to about 4 mg/kg; about 3.5 mg/kg to about 4.5 mg/kg; about 4 mg/kg to about 5 mg/kg; about 5 mg/kg to about 7 mg/kg; about 6 mg/kg to about 8 mg/kg; about 7 mg/kg to about 9 mg/kg; about 8 mg/kg to about 10 mg/kg; about 10 mg/kg to about 15 mg/kg; about 12.5 mg/kg to about 17.5 mg/kg; about 15 mg/kg to about 20 mg/kg; about 17.5 mg/kg to about 22.5 mg/kg; about 20 mg/kg to about 25 mg/kg; about 22.5 mg/kg to about 27.5 mg/kg; about 25 mg/kg to about 30 mg/kg; about 30 mg/kg to about 40 mg/kg; about 35 mg/kg to about 45 mg/kg; about 40 mg/kg to about 50 mg/kg; about 45 mg/kg to about 55 mg/kg; about 50 mg/kg to about 60 mg/kg; about 55 mg/kg to about 65 mg/kg; about 60 mg/kg to about 70 mg/kg; about 65 mg/kg to about 75 mg/kg. Other dosage ranges are also possible.

Amount, frequency, and duration of administration will depend on a variety of factors, such as the individual's age, weight, and disease condition. Anti-PG treatment is indicated in subjects with liver cancer, including HCC and hepatoblastoma, either primary or recurring. Treatment is indicated at any stage of liver cancer, and especially in individuals for whom transplant or surgical resection is not available or contra-indicated.

A treatment regimen for administration can continue for 1 day or more, 2 days or more, 3 days or more, 4 days or more, 5 days or more, 6 days or more, 1 week or more, 2 weeks to indefinitely, for 2 weeks to 6 months, from 3 months to 5 years, from 6 months to 1 or 2 years, from 8 months to 18 months, or the like. Optionally, the treatment regimen provides for repeated administration, e.g., once daily, twice daily, every two days, three days, five days, one week, two weeks, or one month. The repeated administration can be at the same dose or at a different dose. The administration can be repeated once, twice, three times, four times, five times, six times, seven times, eight times, nine times, ten times, or more. A therapeutically effective amount of anti-PG antibody can be administered as a single dose or over the course of a therapeutic regimen, e.g., over the course of a week, two weeks, three weeks, one month, three months, six months, one year, or longer.

7.10. Methods of Monitoring Treatment Efficacy

The present disclosure also provides methods of monitoring a subject being treated with an anti-PG antibody to determine whether the treatment is effective. The level of PG can be measured in the patient receiving anti-PG treatment, and used as an indication of whether the treatment is effective based on whether the measured level is above or below a baseline PG level. See, e.g., U.S. Provisional Patent Application No. 61/293,557, entitled "PROGASTRIN AND LIVER PATHOLOGIES," filed Jan. 8, 2010, and U.S. patent application Ser. No. 12/984,507, entitled "PROGASTRIN AND LIVER PATHOLOGIES," filed Jan. 4, 2011, the entirety of each of which is hereby incorporated by reference. This information can be used by care providers to decide whether to continue administering an anti-PG antibody or modify treatment. These methods can be used to monitor anti-PG treatment, used alone, or in combination with other treatments, as described above.

For purposes of monitoring efficacy of therapy, blood, plasma or serum PG levels can be measured at specified time points. A decrease in concentration over time, and/or a measured level below a threshold value at a particular point in time, is indicative of efficacy. The threshold value may be that discussed above, or could be a subject-specific value obtained from the subject being treated prior to initiation of therapy, or at some point early during a round therapy.

Without wishing to be bound by any particular theory of operation, it is believed that as the numbers and/or sizes of tumors in a patient are reduced as a result of the round of therapy, the total amount of PG produced by the tumors also declines. By contrast, no substantial change, or a rise in PG levels after a round of therapy is completed, may indicate that the therapy was not effective. This information can be used by care providers to decide whether a new round of therapy should be started.

PG levels can be measured using techniques familiar to those of ordinary skill in the art, such as, but not limited to, RIA and ELISA. Anti-hPG antibodies useful for measuring PG levels of human subjects are described in a later section. Examples of assays for measuring PG levels are described in U.S. Provisional Patent Application No. 61/293,557, supra, Examples 1-2.

In a specific embodiment, PG levels may be measured using a sandwich ELISA with one anti-PG antibody targeting the N-terminus of progastrin and a second anti-PG antibody targeting the C-terminus of progastrin. Exemplary N- and C-terminal anti-PG antibodies useful for such a sandwich assay are described in a later section. In such an assay, a surface, such as the wells in a 96-well plate, is prepared to which a known quantity of a first, "capture," N-terminal or C-terminal anti-PG antibody is bound. A test sample is then applied to the surface followed by an incubation period. The surface is then washed and a solution containing a second, "detection," anti-PG antibody is applied, where the detection antibody binds a different epitope of PG (for example, if the capture antibody is a C-terminal anti-PG antibody, an N-terminal anti-PG antibody is used as the detection antibody, and vice versa). PG levels are then measured either directly (if, for example, the detection antibody is conjugated to a detectable label) or indirectly (through a labeled secondary antibody that binds the detection anti-PG antibody). For this assay, antibodies should be used in excess such that all PG is bound and quantified. A specific sandwich assay for measuring plasma and/or serum PG levels is provided in Example 1.

Multiple measurements at different intervals may be taken, and then graphed to determine if a trend exists. In some embodiments, a time-dependent decrease in blood concentration of PG indicates the treatment for liver cancer is effective. In a non-limiting example, PG levels can be determined at weekly, monthly, or annual intervals while a patient is received anti-PG antibodies. Other intervals are also possible.

In an embodiment involving a round of therapy using an anti-PG antibody, one or more measurements may also be taken during the course of therapy so that the effect of the antibodies on PG levels can be estimated. In other such embodiments, where residual anti-PG antibodies are present in a patient during sampling, the data may show a reduction in PG levels, due to sequestration of PG by the antibodies, followed by a rise, as this effect abates, followed by a subsequent decline, if the treatment was effective. In yet other embodiments, post-therapy measurements can be taken after it is estimated that the anti-PG antibodies have been cleared from the patient so that binding of PG by such antibodies does not affect the accuracy of the measurement of PG concentration.

In some embodiments of the methods, the PG level in one or more bodily fluids, such as whole blood, plasma, serum, of a subject receiving anti-PG antibody treatment can be measured and then compared to a baseline level. Typically, PG level is the concentration of PG in the sample, expressed in molar (M) amounts or moles/liter (mol/liter). An above-baseline PG level is indicative of lack of treatment efficacy. By contrast, a PG level equal to or below the baseline level is indicative of treatment efficacy.

Different baselines may be used against which to compare PG levels detected in a patient. The baseline level can be a single number or a range of numbers. The baseline can be based on one or more measurements taken from the patient or based on measurements of PG in samples from a population of individuals. In some embodiments of the methods, the baseline is a PG level from the same patient, taken at one or more interval, for example before the initiation of anti-PG treatment, during the course of treatment, or after treatment has been stopped. In some embodiments, the baseline can be an average PG level in a population of individuals with characteristics similar to those of the individual undergoing monitoring. Such characteristics may include, but are not necessarily limited to sex, age, type and stage of liver cancer, history of surgery, anti-PG treatment, or other treatment. In some embodiments, the baseline is a specific PG level, such as about 50 pM, about 40 pM, about 30 pM, about 20 pM, about 10 pM, about 5 pM, about 2 pM, about 1 pM, or even lower. In some embodiments, the baseline is a range.

In other embodiments, the baseline can be established from average PG levels in a population of patients with characteristics similar to those of the patient undergoing monitoring. Such characteristics may include, but are not necessarily limited to sex, age, primary cancer type, exposure to certain types of treatments, any combination of these, and others. In yet other embodiments, more than one baseline can be used in the monitoring of a particular patient. For example, both a patient-specific baseline, as well as a population-derived baseline can be used.

In some embodiments, where the average PG concentration in a formerly treated cancer patient is in the normal range for the relevant population to which the patient is being compared, and remains steady, the patient would be scored as not having recurrence, and thus does not require new treatment. By contrast, where the PG concentration is seen to rise over a period of time in a formerly treated cancer patient, and in certain embodiments, exceed a threshold derived from population data, the patient may be scored as possibly having recurrence, and thus be a candidate for new treatment against cancer recurrence.

Because eating usually increases gastrin synthesis and secretion, it may also cause transient increases in blood PG levels, which may interfere with the accurate measurement of PG levels in patients being monitored. To avoid this effect, particularly where PG concentration in blood samples is to be determined, samples can be taken from the patient either after fasting, or a sufficient length of time after a meal that any transient effects on PG concentration will have dissipated.

7.11. Anti-PG Antibodies

Antibodies useful in the methods disclosed herein are those that specifically bind human progastrin over other products of the gastrin gene. Referring to FIG. 1, the gastrin gene is translated into a 101-amino acid polypeptide, called pre-progastrin, which contains a signal sequence (underlined) that is cleaved, giving rise to progastrin, an 80-amino-acid polypeptide. Progastrin, in turn, is cleaved to generate a 34-amino-acid product, corresponding in sequence to residues 38-71 of progastrin, which is then extended at its carboxy terminus with a glycine residue, generating glycine-extended G34 ("G34-Gly"). A by-product of this cleavage is a 6-amino-acid peptide, called the C-terminal flanking peptide, or CTFP, which corresponds in sequence to residues 75-80 of progastrin. G34-Gly is then further cleaved to generate a 17-residue polypeptide corresponding in sequence to residues 55-71 of progastrin and referred to as G17-Gly. Removal of the C-terminal glycines of G34-Gly and G17-Gly, followed by C-terminal amidation, yields G34 and G17, respectively, both of which are C-terminal amidated.

As used herein, an antibody is "highly specific for" hPG or "highly specifically binds" hPG if it binds to full-length progastrin but does not bind at all to CTFP, to amidated gastrin, or to glycine-extended gastrin, and is "specific for" hPG or "specifically binds" hPG if it exhibits at least about 5-fold greater binding of hPG than CTFP and the other products of the gastrin gene, as measured in standard binding assays. A specific ELISA assay that can be used to assess the specificity of a particular anti-hPG antibody is provided in Example 2.

Such highly specific and/or specific anti-hPG antibodies (referred to herein as "anti-hPG antibodies") may be polyclonal ("anti-hPG PAbs") or monoclonal ("anti-hPG MAbs"), although for therapeutic uses and, in some instances, diagnostic or other in vitro uses, monoclonal antibodies are preferred.

The epitope bound by the anti-hPG antibodies is not critical. Useful anti-hPG antibodies may bind an N-terminal region of hPG, a C-terminal region of hPG, or a different region of hPG. Recently, it has been discovered that, at least for monoclonal anti-hPG antibodies, the selection of antigen used to raise the anti-hPG antibodies may be important (see, International Application No. PCT/EP2010/006329 filed Oct. 15, 2010 and U.S. application Ser. No. 12/906,041 filed Oct. 15, 2010, the disclosures and specifically disclosed anti-hPG antibodies of which are incorporated herein by reference; hereinafter referred to as the '329 and '041 applications, respectively). As disclosed in the '329 and '041 applications, not all antigens derived from hPG stimulate production of monoclonal antibodies that specifically bind hPG under physiological conditions. Indeed, certain antigens that have been used to successfully raise polyclonal anti-hPG antibodies, such as full-length recombinant hPG (see, e.g., WO 08/076,454 to Singh) and a peptide corresponding to the last ten amino acids at the C-terminal end of hPG (see WO 07/135,542 to Hollande et al.) failed to generate monoclonal antibodies. As noted in the '329 and '041 applications, antigenic N-terminal and C-terminal sequences within the hPG sequence have been identified that can be used to generate monoclonal antibodies that specifically bind hPG. Interestingly, the antigenic sequence need not be limited to regions of the hPG sequence that are unique to it. Peptide antigens having regions of sequence in common with other products of the gastrin gene, for example, G17, G34 and CTFP, yield monoclonal antibodies that not only bind hPG, but bind it specifically.

Anti-hPG antibodies obtainable using a peptide antigen having a sequence corresponding to an N-terminal region of hPG and/or that bind an N-terminal region of hPG are referred to herein as "N-terminal anti-PG antibodies." A specific exemplary antigenic region of hPG that can be used to construct an immunogen suitable for obtaining both polyclonal and monoclonal antibodies specific for hPG corresponds to residue 1 to 14 of hPG: SWKPRSQQPDAPLG (SEQ ID NO:25). Exemplary immunogens useful for obtaining N-terminal anti-hPG antibodies, as well as CDR and $V_H$ and $V_L$ sequences of N-terminal anti-hPG monoclonal antibodies obtained with these exemplary immunogens, are provided in TABLE 1A, below, and the Example sections:

TABLE 1A

N-Terminal Anti-hPG Monoclonal Antibodies

| Immunogen | Hybridoma (Deposit #) | MAb | Murine CDR Sequences | | Murine $V_H$ and $V_L$ Sequences | Humanized $V_H$ and $V_L$ Sequences (projected) |
|---|---|---|---|---|---|---|
| N1 | 43B9G11 | MAb1 | | | | |
| N1 | WE5H2G7 | MAb2 | | | | |
| N2 | 6B5B11C10 | MAb3 | $V_H$ CDR 1.3 | GYIFTSYW (SEQ ID NO: 1) | m$V_H$.3 (SEQ ID NO. 12) | h$V_H$.3 (SEQ ID NO: 21) |
| | | | $V_H$ CDR 2.3 | FYPGNSDS (SEQ ID NO: 2) | | |
| | | | $V_H$ CDR 3.3 | TRRDSPQY (SEQ ID NO: 3) | | |
| | | | $V_L$ CDR 1.3 | QSIVHSNGNTY (SEQ ID NO: 4) | m$V_L$.3 (SEQ ID NO: 13) | h$V_L$.3 (SEQ ID NO: 22) |
| | | | $V_L$ CDR 2.3 | KVS (SEQ ID NO: 5) | | |
| | | | $V_L$ CDR 3.3 | FQGSHVPFT (SEQ ID NO: 6) | | |
| N2 | 20D2C3G2 | MAb4 | $V_H$ CDR 1.4 | GYTFSSSW (SEQ ID NO: 7) | m$V_H$.4 (SEQ ID NO: 14) | h$V_H$.4 (SEQ ID NO: 23) |
| | | | $V_H$ CDR 2.4 | FLPGSGST (SEQ ID NO: 8) | | |
| | | | $V_H$ CDR 3.4 | ATDGNYDWFAY (SEQ ID NO: 9) | | |
| | | | $V_L$ CDR 1.4 | QSLVHSSGVTY (SEQ ID NO: 10) | m$V_L$.4 (SEQ ID NO: 15) | h$V_L$.4 (SEQ ID NO: 24) |
| | | | $V_L$ CDR 2.4 | KVS (SEQ ID NO: 5) | | |
| | | | $V_L$ CDR 3.4 | SQSTHVPPT (SEQ ID NO: 11) | | |
| N2 | 1E9A4A4 (I-4376) | MAb15 | | | | |

TABLE 1A-continued

N-Terminal Anti-hPG Monoclonal Antibodies

| Immunogen | Hybridoma (Deposit #) | MAb | Murine CDR Sequences | | Murine $V_H$ and $V_L$ Sequences | Humanized $V_H$ and $V_L$ Sequences (projected) |
|---|---|---|---|---|---|---|
| N2 | 1E9D9B6 | MAb16 | $V_H$ CDR 1.16 | GYTFTSYY (SEQ ID NO: 39) | $mV_H$.16 (SEQ ID NO: 61) | $hV_H$.16a (SEQ ID NO: 84) |
| | | | $V_H$ CDR 2.16 | INPSNGGT (SEQ ID NO: 43) | | $hV_H$.16b (SEQ ID NO: 86) |
| | | | $V_H$ CDR 3.16 | TRGGYYPFDY (SEQ ID NO: 47) | | $hV_H$.16c (SEQ ID NO: 88) |
| | | | $V_L$ CDR 1.16 | QSLLDSDGKTY (SEQ ID NO: 50) | $mV_L$.16 (SEQ ID NO: 65) | $hV_L$.16a (SEQ ID NO: 85) |
| | | | $V_L$ CDR 2.16 | LVS (SEQ ID NO: 53) | | $hV_L$.16b (SEQ ID NO: 87) |
| | | | $V_L$ CDR 3.16 | WQGTHSPYT (SEQ ID NO: 57) | | $hV_L$.16c (SEQ ID NO: 89) |
| N2 | 1C8D10F5 | MAb17 | | | | |
| N2 | 1A7C3F11 | MAb18 | | | | |
| N2 | 1B3B4F11 | MAb19 | $V_H$ CDR 1.19 | GYSITSDYA (SEQ ID NO: 40) | $mV_H$.19 (SEQ ID NO: 62) | $hV_H$.19a (SEQ ID NO: 90) |
| | | | $V_H$ CDR 2.19 | ISFSGYT (SEQ ID NO: 44) | | $hV_H$.19b (SEQ ID NO: 92) |
| | | | $V_H$ CDR 3.19 | AREVNYGDSYHFDY (SEQ ID NO: 48) | | $hV_H$.19c (SEQ ID NO: 94) |
| | | | $V_L$ CDR 1.19 | SQHRTYT (SEQ ID NO: 51) | $mV_L$.19 (SEQ ID NO: 66) | $hV_L$.19a (SEQ ID NO: 91) |
| | | | $V_L$ CDR 2.19 | VKKDGSH (SEQ ID NO: 54) | | $hV_L$.19b (SEQ ID NO: 93) |
| | | | $V_L$ CDR 3.19 | GVGDAIKGQSVFV (SEQ ID NO: 58) | | $hV_L$.19c (SEQ ID NO: 95) |
| N2 | 1C11F5E8 | MAb20 | | | | |

Immunogen N1 = SWKPRSQQPDAPLG-Ahx-Cys-BSA, also represented as (SEQ ID NO: 25)-Ahx-Cys-BSA
Immunogen N2 = SWKPRSQQPDAPLG-Ahx-Cys-KLH, also represented as (SEQ ID NO: 25)-Ahx-Cys-KLH
In TABLE 1A, all amino acid sequences are represented using conventional N→C orientation. For each immunogen, the progastrin peptide was synthesized with a C-terminal linker of one aminohexanoic acid (Ahx) residue followed by a cysteine (Cys) residue, which was then conjugated to a either a bovine serum albumin ("BSA") or keyhole limpet hemocyanin("KLH")carrier via the Cys linker residue.

Anti-hPG antibodies obtainable using a peptide antigen having a sequence corresponding to a C-terminal region of hPG, and/or that bind a C-terminal region of hPG, are referred to herein as "C-terminal anti-hPG antibodies." A specific exemplary antigenic region that can be used to construct an immunogen useful for obtaining both polyclonal and monoclonal C-terminal anti-hPG antibodies corresponds to residues 55 to 80 of hPG: QGPWLEEEEEAYG-WMDFGRRSAEDEN (SEQ ID NO:27). Exemplary immunogens including this antigen useful for obtaining C-terminal anti-hPG antibodies, as well as CDR and $V_H$ and $V_L$ sequences of C-terminal anti-hPG monoclonal antibodies obtained with these exemplary immunogens, are provided in TABLE 1B, below, and the Examples section.

TABLE 1B

C-Terminal Anti-hPG Monoclonal Antibodies

| Immunogen | Hybridoma (Deposit #) | MAb | Murine CDR Sequences | | Murine $V_H$ and $V_L$ Sequences | Humanized $V_H$ and $V_L$ Sequences (projected) |
|---|---|---|---|---|---|---|
| C1 | 1B4A11D11 (I-4371) | MAb5 | | | | |
| C1 | 1B6A11F2 (I-4372) | MAb6 | | | | |
| C1 | 1B11E4B11 (I-4373) | MAb7 | | | | |
| C1 | 1C10D3B9 | MAb8 | $V_H$ CDR 1.8 | GFTFTTYA (SEQ ID NO: 37) | $mV_H$.8 (SEQ ID NO: 59) | $hV_H$.8a (SEQ ID NO: 75) |
| | | | $V^H$ CDR 2.8 | ISSGGTYT (SEQ ID NO: 41) | | $hV_H$.8b (SEQ ID NO: 77) |
| | | | $V_H$ CDR 3.8 | ATQGNYSLDF (SEQ ID NO: 45) | | $hV_H$.8c (SEQ ID NO: 79) |

TABLE 1B-continued

C-Terminal Anti-hPG Monoclonal Antibodies

| Immunogen | Hybridoma (Deposit #) | MAb | Murine CDR Sequences | | Murine $V_H$ and $V_L$ Sequences | Humanized $V_H$ and $V_L$ Sequences (projected) |
|---|---|---|---|---|---|---|
| | | | $V_L$ CDR 1.8 | KSLRHTKGITF (SEQ ID NO: 49) | $mV_L.8$ (SEQ ID NO: 63) | $hV_L.8a$ (SEQ ID NO: 76) |
| | | | $V_L$ CDR 2.8 | QMS (SEQ ID NO: 52) | | $hV_L.8b$ (SEQ ID NO: 78) |
| | | | $V_L$ CDR 3.8 | AQNLELPLT (SEQ ID NO: 55) | | $hV_L.8c$ (SEQ ID NO: 76) |
| C1 | 1D8F5B3 | MAb9 | | | | |
| C1 | 1E1C7B4 | MAb10 | | | | |
| C1 | 2B4C8C8 (I-4374) | MAb11 | | | | |
| C1 | 2B11E6G4 (I-4375) | MAb12 | | | | |
| C1 | 2C6C3C7 | MAb13 | $V_H$ CDR 1.13 | GFIFSSYG (SEQ ID NO: 38) | $mV_H.13$ (SEQ ID NO: 60) | $hV_H.13a$ (SEQ ID NO: 80) |
| | | | $V_H$ CDR 2.13 | INTFGDRT (SEQ ID NO: 42) | | $hV_H.13b$ (SEQ ID NO: 82) |
| | | | $V_H$ CDR 3.13 | ARGTGTY (SEQ ID NO: 46) | | |
| | | | $V_L$ CDR 1.13 | QSLLDSDGKTY (SEQ ID NO: 50) | $mV_L.13$ (SEQ ID NO: 64) | $hV_L.13a$ (SEQ ID NO: 81) |
| | | | $V_L$ CDR 2.13 | LVS (SEQ ID NO: 53) | | $hV_L.13b$ (SEQ ID NO: 83) |
| | | | $V_L$ CDR 3.13 | WQGTHFPQT (SEQ ID NO: 56) | | |
| C1 | 2H9F4B7 | MAb14 | | | | |
| C2 | 1F11F5E10 | MAb21 | | | | |
| C2 | 1F11F5G9 | MAb22 | | | | |
| C2 | 1A11F2C9 | MAb23 | | | | |

Immunogen C1 = KLH-Cys-Ahx-Ahx-QGPWLEEEEEAYGWMDFGRRSAEDEN, also represented as KLH-Cys-Ahx-Ahx-(SEQ ID NO: 27)
Immunogen C2 = DT-Cys-Ahx-Ahx-QGPWLEEEEEAYGWMDFGRRSAEDEN, also represented as DT-Cys-Ahx-Ahx-(SEQ ID NO: 27)
In TABLE 1B, all amino acid sequences are represented using conventional N→C orientation. For each immunogen, the progastrin peptide was synthesized with an N-terminal Ahx-Ahx-Cys linker, which was then conjugated to a either a keyhole limpet hemocyanin ("KLH") or a diphtheria toxin ("DT") carrier via the Cys linker residue.

The specific epitopes bound by the exemplary anti-hPG monoclonal antibodies MAb1-MAb23 provided in TABLES 1A and 1B were mapped using the SPOT technique and alanine scanning, as described in Laune et al., 2002, J. Immunol. Methods 267:53-70 and Laune, 1997, J. Biol. Chem. 272:30937-30944, respectively (see also, Example 6 of the '329 application).

In the SPOT technique, 15 amino acid peptide sequences spanning a putative epitope are generated and spotted onto a nitrocellulose membrane which is then probed with the test antibody to determine the minimal epitope sequence recognized by the antibody. Alanine scanning is used to determine residues within an epitope that are critical for antibody binding. Each residue within a putative epitope is mutated, one by one, to an alanine, and the alanine-containing peptides are then probed with the test antibody.

For N-terminal anti-hPG monoclonal antibodies MAbs1-4 and 15-20, epitopes comprise at least the following sequences: DAPLG (SEQ ID NO:28), PDAPLG (SEQ ID NO:29), PRSQQPD (SEQ ID NO:30), WKPRSQQPD (SEQ ID NO:31), or WKPRSQQPDAPLG (SEQ ID NO:32), as shown in TABLE 2A below.

TABLE 2A

| MAb# | PG peptide antigen: SWKPRSQQPDAPLG | SEQ ID NO |
|---|---|---|
| MAb2 | WKPRSQQPDAPLG | 32 |
| MAb4 | WKPRSQQPDAPLG | 32 |
| MAb1 | PDAPLG | 29 |
| MAb3 | DAPLG | 28 |
| MAb17 | WKPRSQQPD | 31 |
| MAb18 | WKPRSQQPD | 31 |
| MAb19 | WKPRSQQPD | 31 |
| MAb20 | WKPRSQQPD | 31 |
| MAb15 | PRSQQPD | 30 |
| MAb16 | PRSQQPD | 30 |

For C-terminal anti-hPG monoclonal antibodies MAbs5-7, 9-12, 14 and 21-23, epitopes comprise at least the following sequences: FGRR (SEQ ID NO:33), MDFGR (SEQ ID NO:34), AEDEN (SEQ ID NO:35), and GWMD-FGRR (SEQ ID NO:36), as shown in TABLE 2B, below.

TABLE 2B

| MAb# | PG peptide antigen: QGPWLEEEEEAYGWMDFGRRSAEDEN | SEQ ID NO |
|---|---|---|
| MAb14 | GWMDFGRR | 36 |
| MAb11 | MDFGR | 34 |
| MAb5 | FGRR | 33 |
| MAb6 | FGRR | 33 |
| MAb7 | FGRR | 33 |
| MAb9 | FGRR | 33 |
| MAb10 | FGRR..E | 33 |
| MAb12 | FGRR | 33 |
| MAb23 | AEDEN | 35 |

The epitope mapping experiments reveal that anti-hPG MAb2 and MAb4 bind the same epitope; anti-hPG MAb1 and MAb3 bind approximately the same epitope; MAb17, MAb18, MAb19, and MAb20 bind approximately the same epitope; MAb15 and MAb16 bind approximately the same epitope; anti-hPG MAb5, MAb6, MAb7, MAb9, and MAb12 bind the same epitope and bind approximately the same epitope as anti-hPG MAb10; and anti-hPG MAb11 and MAb14 bind approximately the same epitope.

Specific embodiments of N-terminal anti-PG antibodies useful in the methods and kits described herein include antibodies that bind an epitope that includes residues 10 to 14 of hPG (SEQ ID NO:28), residues 9 to 14 of hPG (SEQ ID NO:29), residues 4 to 10 of hPG (SEQ ID NO:30), residues 2 to 10 of hPG (SEQ ID NO:31), or residues 2 to 14 of hPG (SEQ ID NO:32).

Specific embodiments of C-terminal anti-PG antibodies useful in the methods and kits described herein include antibodies that bind an epitope that includes residues 71 to 74 of hPG (SEQ ID NO:33), residues 69 to 73 of hPG (SEQ ID NO:34), residues 76 to 80 of hPG (SEQ ID NO:35), or residues 67 to 74 of hPG (SEQ ID NO:36).

N-terminal and C-terminal anti-hPG antibodies useful in the methods and kits disclosed herein in addition to those provided in TABLES 1A & 1B can be identified in competitive binding assays with exemplary MAbs 1-23, or with other reference antibodies that bind N- or C-terminal epitopes, as will be described in more detail in a later section.

As also reported in the '329 and '041 applications, not all anti-hPG antibodies, even those that exhibit a high degree of specificity and affinity for hPG, may neutralize the biological activity of hPG. For example, although anti-hPG MAb14 binds hPG with a $K_D$ of about 6 pM, it did not inhibit the growth of colorectal cancer cells in an in vitro assay, whereas other anti-hPG monoclonal antibodies exhibited significant inhibitory activity (see, e.g., Example 7 of the '329 application). While both non-neutralizing and neutralizing antibodies that specifically bind hPG are useful for the various diagnostic and monitoring methods described herein, anti-hPG antibodies useful for therapeutic methods should exhibit neutralizing activity.

As used herein, a "neutralizing anti-hPG antibody" is an anti-hPG antibody that yields a statistically significant reduction in the number of live Huh7 cells in a test sample treated with the anti-hPG antibody as compared to a control sample treated with a non-specific antibody. A specific assay for assessing the ability of any particular anti-hPG antibody to neutralize hPG is described in Example 3. Those anti-hPG antibodies that exhibit at least about a 50% reduction in the number of live cells in this assay are believed to be especially useful in treating liver cancer, although anti-hPG antibodies exhibiting lower levels of neutralizing activity, for example, a statistically significant reduction of 40%, 30%, 20%, 15%, or even 10%, in the number of live cells in this assay are expected to provide therapeutic benefits.

Accordingly, in some embodiments, for example therapeutic embodiments, useful anti-hPG antibodies are neutralizing. As disclosed in the '329 and '041 applications, the ability of an anti-hPG monoclonal antibody is not epitope-dependent, as both N-terminal and C-terminal anti-hPG monoclonal antibodies exhibited neutralizing activity in assays with liver cancer cells. Thus, in some specific embodiments, the neutralizing anti-hPG antibodies are N-terminal neutralizing anti-hPG antibodies. In other embodiments, the neutralizing anti-hPG antibodies are C-terminal neutralizing anti-hPG antibodies.

The affinity of any specific anti-hPG antibody is not critical. However, for some uses, antibodies exhibiting affinities of at least about 1 µM may be preferred. For therapeutic uses, an affinity of at least about 90 nM, 80 nM, 70 nM, 60 nM, 50 nM, 40 nM, 30 nM, 20 nM, 15 nM, 10 nM, 7 nM, 6 nM, 5 nM, 4 nM, 3 nM, 2 nM, 1 nM, 0.1 nM, 0.01 nM, or even greater, may be desirable. The measured affinities of the anti-hPG monoclonal antibodies identified in TABLES 1A & 1B range from $10^{-6}$ to $10^{-12}$ M, as noted in TABLE 3, below:

TABLE 3

| MAb# | Affinity (measured $K_D$) |
|---|---|
| MAb1 | 2.5 µM (2.5 × $10^{-6}$M) |
| MAb2 | 185 nM (1.85 × $10^{-7}$M) |
| MAb3 | 6.4 nM (6.4 × $10^{-9}$M) |
| MAb4 | 3.5 nM (3.5 × $10^{-9}$M) |
| MAb5 | 13 pM (1.30 × $10^{-11}$M) |
| MAb6 | 0.6 nM (6.38 × $10^{-10}$M) |
| MAb7 | 58 pM (5.84 × $10^{-11}$M) |
| MAb8 | 0.1 nM (1.08 × $10^{-10}$M) |
| MAb10 | 3.6 nM (3.62 × $10^{-9}$M) |
| MAb11 | 0.3 nM (3.12 × $10^{-10}$M) |
| MAb12 | 0.4 nM (4.43 × $10^{-10}$M) |
| MAb13 | 0.6 nM (6.12 × $10^{-10}$M) |
| MAb14 | 6.8 pM (6.86 × $10^{-12}$M) |
| MAb15 | 0.2 nM (2.11 × $10^{-10}$M) |
| MAb16 | 0.2 nM (2.78 × $10^{-10}$M) |
| MAb17 | 8.3 nM (8.29 × $10^{-9}$M) |
| MAb18 | 1.2 nM (1.24 × $10^{-9}$M) |
| MAb19 | 0.7 nM (7.79 × $10^{-10}$M) |
| MAb20 | 0.2 nM (2.47 × $10^{-10}$M) |
| MAb21 | 3.9 nM (3.90 × $10^{-9}$M) |
| MAb22 | 5 nM (4.94 × $10^{-9}$M) |
| MAb23 | 0.4 µM (3.99 × $10^{-7}$M) |

An anti-PG monoclonal antibody having an affinity especially suited for a particular desired application can be readily selected from amongst these, or generated or designed using the various immunogens, complementarity determining region (CDR) sequences, variable heavy ($V_H$) and variable light ($V_L$) chain sequences of anti-hPG antibodies described herein. The affinity of any particular anti-PG monoclonal antibody can be determined using techniques well known in the art or described herein, such as for example, ELISA, isothermal titration calorimetry (ITC), BIAcore, or fluorescent polarization assays. A specific assay is provided in Example 4.

As noted in TABLES 1A & 1B, several N-terminal and C-terminal monoclonal anti-hPG antibodies have been identified. All of these antibodies are specific for hPG as measured by the assay described in Example 2, and, with the exception of MAb14, all exhibited neutralizing activity in tests with colorectal cancer cells. All of the antibodies tested with liver cancer cells (MAbs 3, 8, 13, 16 and 19) exhibited neutralizing activity. Several of the hybridomas useful for obtaining the antibodies were deposited on Oct. 6, 2010 with the Collection Nationale de Cultures de Microorganisms (CNCM, Institut Pasteur, 25 rue du Docteur Roux, F-75724 Paris Cedex 15, France), in accordance with the Treaty of Budapest. The designated names of the hybridomas producing anti-hPG MAbs1-23 and the depository registration numbers of those hybridomas deposited are provided in TABLES 1A & 1B. In addition, for several of the antibodies, the amino acid sequences of their variable heavy chains ($V_H$), variable light chains ($V_L$), $V_L$ complementarity determining regions (CDRs) and $V_H$ CDRs have been determined. These amino acid sequences, and the shorthand nomenclature used to reference them throughout the disclosure, are also provided in TABLES 1A & 1B. Briefly, murine heavy and light chain variable domains are referred to herein as $mV_H$ and $mV_L$ followed by the number of the corresponding monoclonal antibody, for example $mV_H$.3 and $mV_L$.3 for the variable light and variable heavy chains of anti-hPG MAb3, respectively. Similarly, human heavy and light chain variable domains are referred to herein as $hV_H$ and $hV_L$ followed by the number of the corresponding monoclonal antibody. The three variable heavy chain CDRs and three variable light chain CDRs are referred to as $V_H$ CDR 1, 2, or 3, and $V_L$ CDR 1, 2, or 3, respectively, followed by the number of the specific anti-hPG monoclonal antibody. For example, $V_H$ CDR 1 of MAb3 is denoted $V_H$ CDR 1.3 and $V_L$ CDR 1 of MAb3 is denoted $V_L$ CDR 1.3. $V_H$ CDR 2 of MAb3 is denoted $V_H$ CDR 2.3, and $V_L$ CDR 2 of MAb3 is denoted $V_L$ CDR 2.3.

It is expected that corresponding CDRs and/or $V_H$ and $V_L$ chains of anti-hPG monoclonal antibodies that bind approximately the same epitopes could be interchanged to yield new anti-hPG monoclonal antibodies useful in the methods and kits described herein. For example, as noted above, exemplary anti-hPG monoclonal antibodies MAb5 and MAb6 bind the same epitope. An anti-hPG monoclonal antibody can be designed that includes, in its $V_L$ chain, various combinations of the $V_L$ CDRs of these two antibodies, and/or in its $V_H$ chain various combinations of the $V_H$ CDRs of these two antibodies. As a specific non-limiting example to illustrate the various combinations possible, such an antibody could include in its $V_L$ chain, CDRs 1 and 2 of MAb5 ($V_L$ CDR 1.5 and $V_L$ CDR 2.5, respectively) and CDR 3 of MAb6 ($V_L$ CDR 3.6), and in its $V_H$ chain, CDR 1 of MAb6 ($V_H$ CDR 1.6) and CDRs 2 and 3 of MAb5 ($V_H$ CDR 2.5 and $V_H$ CDR 3.5, respectively). Amino acid sequences of CDRs of antibodies (also known as hypervariable regions) produced by hybridomas that have been deposited can be obtained using conventional means.

As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The anti-PG antibodies described herein may contain modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions in the order FR1-CDR1-FR2-CDR2-FR3-CDR3-FR4 and, with the CDRs from the other chain, contribute to the formation of the target binding site of antibodies (see Kabat et al., 1987, *Sequences of Proteins of Immunological Interest*, National Institute of Health, Bethesda, Md.). As used herein, numbering of immunoglobulin amino acid residues is done according to the immunoglobulin amino acid residue numbering system of Kabat et al., unless otherwise indicated.

With reference to TABLE 1A, specific embodiments of N-terminal anti-hPG antibodies useful in the methods and kits described herein include, but are not limited to, the following:

(a) antibodies having $V_L$ CDRs that correspond in sequence to the $V_L$ CDRs of MAb1, MAb2, MAb3, MAb4, MAb15, MAb16, MAb17, MAb18, MAb19 or MAb20, and $V_H$ CDRs that correspond in sequence to the $V_H$ CDRs of MAb1, MAb2, MAb3, MAb4, MAb15, MAb16, MAb17, MAb18, MAb19 or MAb20;

(b) antibodies having $V_L$ CDRs and $V_H$ CDRs that correspond in sequence to the $V_L$ and $V_H$ CDRs of MAb1, MAb2, MAb3, MAb4, MAb15, MAb16, MAb17, MAb18, MAb19 or MAb20;

(c) antibodies in which:
  (i) $V_L$ CDR 1 is selected from QSIVHSNGNTY ("$V_L$ CDR 1.3"; SEQ ID NO:4), QSLVHSSGVTY ("$V_L$ CDR 1.4"; SEQ ID NO:10), QSLLDSDGKTY ("$V_L$ CDR 1.16"; SEQ ID NO:50), and SQHRTYT ("$V_L$ CDR 1.19"; SEQ ID NO:51);
  (ii) $V_L$ CDR 2 is selected from KVS ("$V_L$ CDR 2.3" or "$V_L$ CDR 2.4"; SEQ ID NO:5), LVS ("$V_L$ CDR 2.16"; SEQ ID NO:53), and VKKDGSH ("$V_L$ CDR 2.19"; SEQ ID NO:54);
  (iii) $V_L$ CDR 3 is selected from FQGSHVPFT ("$V_L$ CDR 3.3"; SEQ ID NO:6), SQSTHVPPT ("$V_L$ CDR 3.4"; SEQ ID NO:11), WQGTHSPYT ("$V_L$ CDR 3.16"; SEQ ID NO:57), and GVGDAIKGQSVFV ("$V_L$ CDR 3.19"; SEQ ID NO:58);
  (iv) $V_H$ CDR 1 is selected from GYIFTSYW ("$V_H$ CDR 1.3"; SEQ ID NO:1), GYTFSSSW ("$V_H$ CDR 1.4"; SEQ ID NO:7), GYTFTSYY ("$V_H$ CDR 1.16"; SEQ ID NO:39), and GYSITSDYA ("$V_H$ CDR 1.19"; SEQ ID NO:40);
  (v) $V_H$ CDR 2 is selected from FYPGNSDS ("$V_H$ CDR 2.3"; SEQ ID NO:2), FLPGSGST ("$V_H$ CDR 2.4"; SEQ ID NO:8), INPSNGGT ("$V_H$ CDR 2.16"; SEQ ID NO:43), and ISFSGYT ("$V_H$ CDR 2.19"; SEQ ID NO:44); and
  (vi) $V_H$ CDR 3 is selected from TRRDSPQY ("$V_H$ CDR 3.3"; SEQ ID NO:3), ATDGNYDWFAY ("$V_H$ CDR 3.4" SEQ ID NO:9), TRGGYYPFDY ("$V_H$ CDR 3.16"; SEQ ID NO:47), and AREVNYGDSYHFDY ("$V_H$ CDR 3.19"; SEQ ID NO:48);

(d) antibodies having a $V_L$ that corresponds in sequence to the $V_L$ of MAb1, MAb2, MAb3, MAb4, MAb15, MAb16, MAb17, MAb18, MAb19 or MAb20 and a $V_H$ that corresponds in sequence to the $V_H$ of MAb1, MAb2, MAb3, MAb4, MAb15, MAb16, MAb17, MAb18, MAb19 or MAb20; and (e) antibodies having a $V_L$ and a $V_H$ that corresponds in sequence to the $V_L$ and $V_H$ of MAb1, MAb2, MAb3, MAb4, MAb15, MAb16, MAb17, MAb18, MAb19 or MAb20.

With reference to TABLE 1B, specific embodiments of C-terminal anti-hPG antibodies useful in the methods and kits described herein include, but are not limited to, the following:

(a) antibodies having $V_L$ CDRs that correspond in sequence to the $V_L$ CDRs of MAb5, MAb6, MAb7, MAb8, MAb9, MAb10, MAb11, MAb12, MAb13, MAb14, MAb21, MAb22 or MAb23 and $V_H$ CDRs that correspond in sequence to the $V_H$ CDRs of MAb5, MAb6, MAb7, MAb8, MAb9, MAb10, MAb11, MAb12, MAb13, MAb14, MAb21, MAb22 or MAb23;

(b) antibodies having $V_L$ CDRs and $V_H$ CDRs that correspond in sequence to the $V_L$ and $V_H$ CDRs of MAb5, MAb6, MAb7, MAb8, MAb9, MAb10, MAb11, MAb12, MAb13, MAb14, MAb21, MAb22 or MAb23;

(c) antibodies in which:
  (i) $V_L$ CDR 1 is selected from KSLRHTKGITF ("$V_L$ CDR 1.8"; SEQ ID NO:49) and QSLLDSDGKTY ("$V_L$ CDR 1.13"; SEQ ID NO:50);
  (ii) $V_L$ CDR 2 is selected from QMS ("$V_L$ CDR 2.8"; SEQ ID NO:52) and LVS ("$V_L$ CDR 2.13"; SEQ ID NO:53);
  (iii) $V_L$ CDR 3 is selected from AQNLELPLT ("$V_L$ CDR 3.8"; SEQ ID NO:55) and WQGTHFPQT ("$V_L$ CDR 3.13"; SEQ ID NO:56);
  (iv) $V_H$ CDR 1 is selected from GFTFTTYA ("$V_H$ CDR 1.8"; SEQ ID NO:37) and GFIFSSYG ("$V_H$ CDR 1.13"; SEQ ID NO:38);
  (v) $V_H$ CDR 2 is selected from ISSGGTYT ("$V_H$ CDR 2.8"; SEQ ID NO:41) and INTFGDRT ("$V_H$ CDR 2.13"; SEQ ID NO:42); and
  (vi) $V_H$ CDR 3 is selected from ATQGNYSLDF ("$V_H$ CDR 3.8"; SEQ ID NO:45) and ARGTGTY ("$V_H$ CDR 3.13"; SEQ ID NO:46);

(d) antibodies having a $V_L$ that corresponds in sequence to the $V_L$ of MAb5, MAb6, MAb7, MAb8, MAb9, MAb10, MAb11, MAb12, MAb13, MAb14, MAb21, MAb22 or MAb23 and a $V_H$ that corresponds in sequence to the $V_H$ of MAb5, MAb6, MAb7, MAb8, MAb9, MAb10, MAb11, MAb12, MAb13, MAb14, MAb21, MAb22 or MAb23; and (e) antibodies having a $V_L$ and a $V_H$ that correspond in sequence to the $V_L$ and $V_H$ that correspond in sequence to the $V_L$ and $V_H$ of MAb5, MAb6, MAb7, MAb8, MAb9, MAb10, MAb11, MAb12, MAb13, MAb14, MAb21, MAb22 or MAb23.

As will be appreciated by skilled artisans, anti-hPG antibodies useful in the diagnostic methods can be of any origin, including, for example, mammalian (e.g., human, primate, rodent, goat or rabbit), non-mammalian, or chimeric in nature (derived from more than one species of origin). Antibodies suitable for therapeutic uses in animals, including humans, are preferably derived from the same species intended to be treated, or have been modified or designed to be non-immunogenic or have reduced immunogenicity in the animal being treated. A specific class of anti-hPG antibodies useful for therapeutic uses in humans is the class of humanized antibodies, discussed in more detail, below. Anti-hPG antibodies useful in the methods and kits described herein can also be of, or derived from, any isotype, including, for example, IgA (e.g., IgA1 or IgA2), IgD, IgE, IgG (e.g., IgG1, IgG2, IgG3 or IgG4) or IgM. Anti-hPG antibodies designed for therapeutic uses are preferably of the IgG isotype.

In some embodiments, anti-hPG antibodies useful for therapeutic methods described herein are humanized. In general, humanized antibodies comprise substantially all of at least one, and typically two, variable domains, in which all or substantially all of the CDR regions correspond to those of a non-human immunoglobulin and all or substantially all of the framework regions are those of a human immunoglobulin consensus sequence, and can be referred to as "CDR-grafted." The humanized antibody can also comprise at least a portion of an immunoglobulin constant region (Fc), typically that of a human immunoglobulin consensus sequence. Methods for humanizing antibodies, including methods for designing humanized antibodies, are well-known in the art. See, e.g., Lefranc et al., 2003, Dev. Comp. Immunol. 27:55-77; Lefranc et al., 2009, Nucl. Acids Res. 37:D1006-1012; Lefranc, 2008, Mol. Biotechnol. 40: 101-111; Riechmann et al., 1988, Nature 332:323-7; U.S. Pat. Nos. 5,530,101, 5,585,089, 5,693,761, 5,693,762 and 6,180,370 to Queen et al.; EP239400; PCT publication WO 91/09967; U.S. Pat. No. 5,225,539; EP592106; EP519596; Padlan, 1991, Mol. Immunol. 28:489-498; Studnicka et al., 1994, Prot. Eng. 7:805-814; Roguska et al., 1994, Proc. Natl. Acad. Sci. 91:969-973; and U.S. Pat. No. 5,565,332, the disclosures of which are hereby incorporated by reference in their entireties.

Humanized versions of antibodies having CDR sequences corresponding to the CDRs of non-human anti-hPG antibodies, including by way of example and not limitation, the various N-terminal anti-hPG monoclonal antibodies provided in TABLE 1A and the various C-terminal anti-hPG monoclonal antibodies provided in TABLE 1B, can be obtained using these well-known methods. Projected sequences for humanized $V_L$ and $V_H$ chains of selected anti-hPG antibodies are provided in TABLES 1A and 1B. Specific examples of humanized antibodies include antibodies comprising:

(a) any three $V_L$ CDRs and any three $V_H$ CDRs disclosed herein;

(b) a heavy chain variable region comprising an amino acid sequence corresponding to SEQ ID NO:21 and a light chain variable region comprising an amino acid sequence corresponding to SEQ ID NO:22;

(c) a heavy chain variable region comprising an amino acid sequence corresponding to SEQ ID NO:23 and a light chain variable region comprising an amino acid sequence corresponding to SEQ ID NO:24;

(d) a heavy chain variable region comprising an amino acid sequence selected from the group consisting of SEQ ID NO:75, 77, and 79 and a light chain variable region comprising an amino acid sequence selected from the group consisting of SEQ ID NO:76 and 78;

(e) a heavy chain variable region comprising an amino acid sequence selected from the group consisting of SEQ ID NO:80 and 82 and a light chain variable region comprising an amino acid sequence selected from the group consisting of SEQ ID NO:81 and 83;

(f) a heavy chain variable region comprising an amino acid sequence selected from the group consisting of SEQ ID NO:84, 86, and 88 and a light chain variable region comprising an amino acid sequence selected from the group consisting of SEQ ID NO:85, 87, and 89; and (g) a heavy chain variable region comprising an amino acid sequence selected from the group consisting of SEQ ID NO:90, 92, and 94 and a light chain variable region comprising an amino acid sequence selected from the group consisting of SEQ ID NO:91, 93, and 95.

As will be recognized by skilled artisans, anti-hPG antibodies having specific binding properties, such as the ability to bind a specific epitope of interest, can be readily obtained using the various antigens and immunogens described herein and assessing their ability to compete for binding hPG with a reference antibody of interest. Any of the anti-hPG antibodies described herein can be utilized as a reference antibody in such a competition assay. A specific assay useful for assessing the ability of an antibody to compete for binding hPG with a biotinylated reference anti-hPG antibody of interest is provided in Example 5.

In conducting an antibody competition study between a reference anti-hPG antibody and any test antibody (irrespective of species or isotype), one may first label the reference with a label detectable either directly, such as, for example, a radioisotope or fluorophore, or indirectly, such as, for example biotin (detectable via binding with fluorescently-labeled streptavidin) or an enzyme (detectable via an enzymatic reaction), to enable subsequent identification. In this case, a labeled reference anti-hPG antibody (in fixed or increasing concentrations) is incubated with a known amount of hPG, forming an hPG:labeled anti-hPG antibody complex. The unlabeled test antibody is then added to the complex. The intensity of the complexed label is measured. If the test antibody competes with the labeled reference anti-hPG antibody for hPG by binding to an overlapping epitope, the intensity of the complexed label will be decrease relative to a control experiment carried out in the absence of test antibody.

Numerous methods for carrying out binding competition assays are known and can be adapted to yield results comparable to the assay described above and in Example 5.

An antibody is considered to compete for binding hPG with a reference anti-hPG antibody, and thus considered to bind approximately the same or an overlapping epitope of hPG as the reference anti-hPG antibody, if it reduces binding of the reference anti-hPG antibody to hPG in a competitive binding assay, and specifically the competitive binding assay of Example 5, by at least 50%, at a test antibody concentration in the range of 0.01-100 µg/mL (e.g., 0.01 µg/mL, 0.08 µg/mL, 0.4 µg/mL, 2 µg/mL, 10 µg/mL, 50 µg/mL or 100 µg/mL or other concentration within the stated range), although higher levels of reduction, for example, 60%, 70%, 80%, 90% or even 100%, may be desirable.

Skilled artisans will appreciate that is some contexts, for example, diagnostic and monitoring contexts, it may be desirable to label the anti-PG antibodies. Such labels are useful for detection and quantification. Suitable labels are well known in the art, and can be "direct" in that they are directly observable or detectable (for example, fluorophores or radioisotopes) or "indirect" in that they interact with something else that produces and observable or detectable signal (for example, an enzyme that acts on a substrate to produce a detectable signal, or a binding molecule such as biotin that binds a labeled, streptavidin molecule). Numerous labeling systems, as well as means for labeling antibodies with them, are known in the art, and are contemplated for use herein.

Although the various anti-hPG antibodies useful in the methods described herein have been exemplified with full length antibodies, skilled artisans will appreciate that binding fragments, or surrogate antibodies designed or derived from full-length antibodies or binding fragments, may also be used. Suitable fragments, surrogates, etc., include, but are not limited to, Fab', F(ab')2, Fab, Fv, vIgG, scFv fragments and surrobodies. Unless specified otherwise, the term "antibody" as used herein is intended to include all forms of antibodies and "antibody-like" surrogate molecules, including single chain antibodies, surrobodies and binding fragments. Antibodies having structures typical of naturally occurring antibodies are referred to herein as "native antibodies."

7.12. Methods of Producing Anti-PG Antibodies

Anti-PG antibodies useful in the methods described herein may be obtained using standard, well-known methods. To express anti-PG antibodies useful in the methods described herein, DNAs encoding partial or full-length light and heavy chains are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-PG antibody light or heavy chain sequences, the expression vector can already carry antibody constant region sequences. For example, one approach to converting the anti-PG antibody $V_H$ and $V_L$ sequences to full-length antibody genes is to insert them into expression vectors already encoding heavy chain constant and light chain constant regions, respectively, such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, *Gene Expression Technology: Methods in Enzymology* 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, puromycin, blasticidin, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies described herein in either prokaryotic or eukaryotic host cells. In certain embodiments, expression of antibodies is performed in eukaryotic cells, e.g., mammalian host cells, for optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub & Chasin, 1980, Proc. Natl. Acad. Sci. USA 77:4216-4220, used with a DHFR selectable marker, e.g., as described in Kaufman & Sharp, 1982, Mol. Biol. 159:601-621), NS0 myeloma cells, COS cells, 293 cells and SP2/0 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as $F_{ab}$ fragments or $scF_v$ molecules. It is understood that variations on the above procedure are within the scope of the present disclosure. For example, it can be desirable to transfect a host cell with DNA encoding either the light chain or the heavy chain (but not both) of an anti-PG antibody described herein.

Recombinant DNA technology can also be used to remove some or all of the DNA encoding either or both of the light and heavy chains that is not necessary for binding to PG. The molecules expressed from such truncated DNA molecules are also useful in the methods described herein.

For recombinant expression of an anti-PG antibody, the host cell can be co-transfected with two expression vectors, the first vector encoding a heavy chain derived polypeptide and the second vector encoding a light chain derived polypeptide. Typically, the two vectors each contain a separate selectable marker. Alternatively, a single vector can be used which encodes both heavy and light chain polypeptides.

Anti-PG antibodies can also be produced by chemical synthesis (e.g., by the methods described in *Solid Phase Peptide Synthesis*, 2nd ed., 1984 The Pierce Chemical Co., Rockford, Ill.). Variant antibodies can also be generated using a cell-free platform (see, e.g., Chu et al., 2001, Biochemia No. 2 (Roche Molecular Biologicals)).

Once an anti-PG antibody has been produced by recombinant expression or synthetic means, it can be purified by any method known in the art for purification of an immunoglobulin molecule, for example, by chromatography (e.g., ion exchange, affinity, particularly by affinity for PG after Protein A or Protein G selection, and sizing column chromatography), centrifugation, differential solubility, or by any other standard technique for the purification of proteins. Further, the anti-PG antibodies or binding fragments thereof can be fused to heterologous polypeptide sequences described herein or otherwise known in the art to facilitate purification.

EXAMPLES

The following examples are illustrative and not intended to be limiting.

Example 1: Quantification of Plasma or Serum PG Levels

Plasma and/or serum levels of PG can be conveniently determined using the following assay. 96-well microtiter plates are coated with between 0.5 and 10 µg/mL of a C-terminal anti-hPG antibody, for example, a rabbit C-terminal anti-hPG polyclonal antibody, or a C-terminal anti-hPG antibody described herein, and then incubated overnight. Plates are then washed three times in PBS-Tween (0.05%) and blocked with 2% (w/v) nonfat dried milk in PBS-Tween (0.05%). Separately, test samples, control samples (blank or PG-negative plasma or serum samples), and between about 5 pM ($0.5 \times 10^{-11}$ M) and about 0.1 nM ($1 \times 10^{-10}$ M) of an hPG reference standard (lyophilized hPG diluted in PG-negative plasma or serum) are prepared in an appropriate diluent (e.g., PBS-Tween 0.05%). Samples are incubated on the coated plates for between 2 and 4 hours at 37° C., or alternatively between 12 and 16 hours at 21° C. After incubation, plates are washed three times with PBS-Tween (0.05%) and incubated with between 0.001 and 0.1 µg/mL of an N-terminal anti-hPG antibody, for example, a polyclonal N-terminal anti-hPG antibody or an N-terminal monoclonal anti-hPG antibody as described herein, coupled to horseradish peroxidase (HRP) (see, Nakane et al., 1974, J. Histochem. Cytochem. 22(12):1084-1091) for 30 minutes at 21° C. Plates are then washed three times in PBS-Tween (0.05%) and HRP substrate is added for 15 minutes at 21° C. The reaction is stopped by added 100 µl, of 0.5M sulfuric acid and an optical density measurement is taken at 405 nm. Test sample hPG levels are determined by comparison to a standard curve constructed from the measurements derived from the hPG reference standard.

Example 2: ELISA Assay for Assessing Specificity of Anti-hPG Antibodies

Specificity of anti-hPG antibodies can be conveniently determined using an ELISA assays as follows. 96-well plates are incubated overnight at 4° C. with appropriate concentration(s) of test polypeptide (e.g., 25 and 50 ng recombinant human PG, and 50 and 250 ng CTFP or other gastrin-derived gene products) in Phosphate-Buffered Saline (PBS), after which the wells are washed three times with wash solution (PBS and 0.1% Tween-20), and then incubated for 2 hours at 22° C. with 100 μL blocking solution (PBS, 0.1% Tween-20, 0.1% Bovine Serum Albumin or casein hydrolysate) per well. After blocking, the wells are washed three times and the antibody to be assayed (test antibody) is added. 100 μL of the test antibody (at 0.3 to 1 ng/mL) in PBS and 0.1% Tween-20 are added to each well. Plates are then incubated for 2 hours at 22° C., after which the test antibody solution is discarded and replaced, after a wash step (3×100 μl, wash solution, as noted above), with blocking solution containing a secondary antibody, a goat anti-mouse IgG (Fc) antibody coupled to horseradish peroxidase. After a 1-hour incubation with secondary antibody, 100 μL of substrate solution (e.g. Fast OPD, or O-Phenylenediamine dihydrochloride, available from Sigma-Aldrich Co., prepared according to manufacturer's directions) is added to each well and incubated in the dark for 20 minutes at 22° C. The reaction is stopped by adding 50 μL of 4N sulfuric acid and the amount of substrate catalyzed determined by measuring the optical density (O.D.) at 492 nm. Substrate conversion is proportional to the amount of primary (test) antibody bound to the antigen. Experiments are run in duplicate and OD measurements plotted as a function of antigen concentration. Test antibodies are scored as specific for PG if the measured O.D. is between 0.2 and 1.5 for hPG and there is no statistically significant signal above background with CTFP or any of the other gastrin-gene derived peptides, where the background is the average signal from control wells containing only PBS.

Example 3: Assay for Assessing Neutralizing Activity of Anti-hPG Antibodies

A specific test for assessing whether a particular anti-hPG antibody is neutralizing can be performed as follows. Huh7 hepatocellular carcinoma cells are seeded in ultra low-adherence 24-well plates (500 cells/well) in serum-free M11 medium. Cells are grown at 37° C. and treated twice daily for 7 days with the test anti-hPG antibody or a control, non-specific monoclonal antibody, at antibody concentrations of about 5 μg/mL. At the end of the experiment, photomicrographs are taken, and the number of spheres per well is counted and the median and percentile distribution calculated. A test antibody is defined as neutralizing in the assay, if the number of spheroids formed by Huh7 cells under low adherence culture conditions shows a statistically significant reduction of at least 20% as compared to cells treated with the control antibody, using an unpaired t-test when testing one anti-hPG antibody or one-way ANOVA with Bonferroni post-hoc test when testing multiple antibodies (with difference considered as significant when p<0.05).

Example 4: Assay for Assessing Affinity of an Anti-hPG Antibody

Affinity constants of anti-hPG antibodies can be measured using the Proteon Technique (BioRad), according to Nahshol et al., 2008, Analytical Biochemistry 383:52-60, hereby incorporated by reference in its entirety. Briefly, for murine anti-PG antibodies, an anti-mouse IgG antibody (50 μg/ml) is first coated on a sensor chip, making sure that the signal detected by the chip after injection of the antibody falls between 10,000 and 11,500 response units (RU). The murine anti-hPG antibody of interest (test antibody) is then injected (at a typical concentration of 30 μg/ml). If the test antibody binds sufficiently, and additional signal of at least 500 RU will be observed. A time-course of binding between test antibody and hPG is then obtained by injecting varying concentrations of hPG, for example 200 nM, 100 nM, 50 nM, 25 nM, and 12.5 nM, and detecting the level of association. Typically, several channels are available to test multiple antibodies in parallel in a single experiment, making it possible to assay binding of a single test antibody at different concentrations of hPG in parallel. One channel should be injected with a murine monoclonal antibody that is not specific to hPG as a control for non-specific binding and another channel should be injected with dilution buffer alone as a baseline for the background signal. Generally, no binding is detectable in the channel injected with non-specific murine antibody. Antibodies displaying a high level of association in this setting, which may result in saturation of the trapped monoclonal antibody by hPG, can be tested against lower hPG concentrations (50 nM, 25 nM, 12.5 nM, 6.25 nM and 3.125 nM), allowing for a more refined measurement.

Affinity constants ($K_D$) are calculated as the ratio between the dissociation constant ($k_d$) and the association constant ($k_a$). Experimental values can be validated by analyzing the statistically relevant similarity between experimental curves based on binding measurements and theoretical profiles.

Affinity constants of non-murine anti-hPG antibodies can be assessed in a similar format using an IgG specific for the species of origin of the anti-hPG test antibody.

Example 5: Assay for Assessing Competitive Binding with a Reference Anti-hPG Antibody A specific assay for assessing whether an antibody of interest (test antibody) competes for binding hPG with a biotinylated reference anti-hPG antibody can be performed as follows. 96-well plates are coated with a capture anti-hPG antibody (polyclonal or monoclonal antibody recognizing an N or C-terminal region of hPG that differs from the epitope recognized by the biotinylated reference anti-hPG antibody), at a concentration to be chosen within the range of 1-10 μg/ml, overnight at 4° C. (0.1 to 1 μg/well). After blocking with blocking buffer (0.1% Tween-20, 0.1% BSA in PBS) for 2 hr at 22° C., recombinant hPG is added at a concentration ranging between 10 pM to 1 nM (10 to 1000 pg/well) and incubated for 2 hr at 22° C. Thereafter, the biotinylated reference anti-hPG antibody (or a mixture containing the biotinylated reference anti-hPG antibody) is added, along with increasing concentrations of unlabeled test antibody, and incubated for 1 hr at 22° C. After washing to remove unbound antibodies, detection of bound labeled reference anti-hPG antibody is performed by incubating the mixture with 50 ng/ml streptavidin-HRP for 1 hr at 22° C., followed by incubation with a chemiluminescent substrate for horseradish peroxidase for 5 nm at 22° C., and then quantifying the relative light units (RLU) in a luminometer. Assays are performed in duplicate.

Antibodies that compete with a reference anti-hPG antibody inhibit the binding of the reference antibody to hPG. An antibody that binds to substantially the same epitope, or with an overlapping epitope, as the reference antibody significantly reduces (for example, by at least 50%) the amount of reference anti-hPG antibody bound, as evidenced by a reduction observed RLUs.

A high control value is obtained from a control experiment carried out by incubating the labeled reference antibody with recombinant hPG without test antibody. A low control value is obtained from a control experiment carried out by incubating the labeled reference antibody with recombinant hPG in the presence of excess concentrations of the unlabeled reference antibody (the unlabeled reference antibody thus competing with the labeled antibody for binding to hPG). The capacity of test antibodies to compete with the reference anti-hPG antibody is then determined by incubating the labeled reference antibody with recombinant hPG in the presence of increasing concentrations of the unlabeled test antibody.

In a test assay, a significant reduction in the observed RLUs in the presence of a test antibody indicates that the test antibody recognizes substantially the same epitope as the reference anti-hPG antibody.

The inhibition of binding can be expressed as an inhibition constant, or $K_i$, which is calculated according to the following formula:

$$K_i = IC_{50}/[1+(\text{reference anti-hPG Ab concentration}/K_D^{\text{reference anti-hPG Ab}})]$$

where "$IC_{50}$" is the concentration of test antibody that yields a 50% reduction in binding of the reference antibody and $K_D^{\text{reference anti-hPG Ab}}$ is the dissociation constant of the reference anti-hPG antibody, a measure of its affinity for hPG. Useful test antibodies that compete with a reference anti-hPG antibody (for example, one of the anti-hPG antibodies described herein) will typically have $K_i$s ranging from 10 pM to 100 nM under assay conditions described herein.

Example 6: Hepatocellular Carcinomas from Liver Cancer Tumors Show Elevated Levels of GAST Gene Expression This example describes the observation that liver tumor samples from patients with hepatocellular carcinoma (HCC) express elevated levels of the GAST gene relative to normal tissue.

A. Methods

Primary liver tumors and normal control tissue were surgically resected from 14 patients. RNA was prepared from both tumor and healthy liver tissue samples and mRNA integrity was controlled using an Agilent Bioanalyser. GAST mRNA expression was measured by quantitative reverse-transcription polymerase chain reaction (RT-PCR) and normalized with HPRT mRNA expression. For RT-PCR, total RNA from HCC samples was extracted using FastRNA Pro Green Kit (MP BioMed) according to the manufacturer's protocol. RNA was reverse transcribed using Superscript II RT (Invitrogen) in the presence of random primer (R&D Systems). Real-time RT-PCR was performed using the Quantifast SYBR Green PCR kit (Qiagen) and the Eppendorf Mastercycler ep realplex (Eppendorf). Primers for GAST and HPRT gene amplification were obtained from Sigma Life Science. Each PCR amplification was performed in triplicate wells using the following conditions: 5 min. at 95° C., followed by a total of 45 two-temperature cycles (10 sec. at 95° C. and 30 sec. at 60° C.).

B. Results

As shown in FIG. 4, GAST mRNA expression was elevated in HCC tumor samples relative to normal liver tissue in 10 of 14 subjects with liver cancer. In the samples where GAST mRNA expression was elevated, the expression ranged 2 to 2800 fold higher compared to normal tissue.

Example 7: Liver Cancer Cell Lines Grown Under Low Adherence Culture Conditions Show Elevated Levels of GAST Gene Expression This example describes the observation that liver cancer cell lines grown under low adherence culture conditions express elevated levels of the GAST gene relative to colorectal cancer cell line.

A. Methods

Two hepatocellular carcinoma cell lines, Huh7 and PLC/PRF/5, a hepatoblastoma cell line, Huh6, and a colorectal cancer cell line, SW480, each were seeded into ultra low adherence flasks in M11 medium, and grown until sphere formation was achieved. Spheres were then processed for RNA extraction. RT-PCR was performed as described in Example 1, except that total RNA was extracted using QIAGEN Rneasy Mini-kit according to the manufacturer's protocol. GAST mRNA expression levels from the liver cancer cell lines were then normalized relative to expression in SW480 cells, which served as a positive control.

B. Results

Figure 5B:
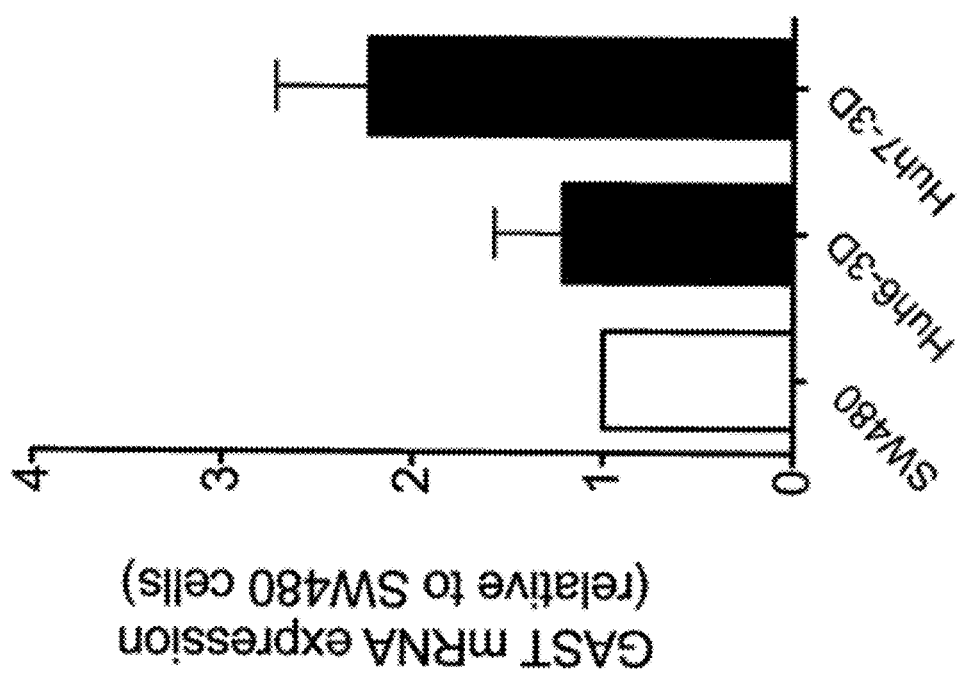

As shown in FIG. 5A-5B, all liver cell lines tested, Huh6, Huh7 and PLC/PRF/5, expressed elevated levels of GAST mRNA compared to the colorectal tumor cell line SW480 when grown under low adherence culture conditions. Results are expressed relative to gastrin gene expression levels in SW480 cells.

Example 8: Side Population Cells Isolated from Liver Cancer Cell Lines and Grown Under Low Adherence Culture Conditions Show Elevated Levels of GAST Gene Expression This example describes the observation that the dye-excluding "side population" cells from two liver cancer cell lines, Huh6 and Huh7, express elevated levels of GAST mRNA compared to the general population of such cells (i.e., side population and non-side population) grown under low adherence culture conditions.

A. Methods

The dye-excluding "side population" cells from Huh6 and Huh7 liver cancer cell lines were isolated from the general population of such cells using FACS. Specifically, cells were dissociated by treatment with trypsin and EDTA. Cells were then incubated in 1 ml staining medium (DMEM, 2% Fetal Bovine Serum, 2 mM EDTA) for 10 min. at 37° C. To a negative control sample was added 1 µl of 50 mM verapamil solution (final concentration 50 µM). Control and test samples were then incubated for 10 min at 37° C. Dye solution was then added to the test samples (2.5 µl of 2 mg/ml Hoechst 33342; final dye concentration of 5 µg/ml), followed by gentle mixing. All samples were then incubated for 50 min at 37° C. with regular gentle mixing. After being incubated on ice for 5-10 min., samples were then centrifuged for 5 min. at 1000 rpm. Cell pellets were then resuspended in 1 ml of a 1:40 dilution of 25 µg/ml propidium iodide solution in M11 medium. Aggregated cells were removed by filtration through a sieve in a 5 ml tube. Samples were then stored on ice until cytometry was performed using a FACSAria cytometer with signal detection at 450 nm and 488 nm. RNA was then purified and GAST mRNA expression levels quantitated as in Examples 6 and 7, and then compared against GAST gene expression levels from Huh6 and Huh7 cells grown as spheroids under low adherence culture conditions, and SW480 colorectal cancer cells. GAST mRNA expression levels from the liver cancer cell lines were then normalized relative to expression in SW480 cells, which served as a positive control.

B. Results

As shown in FIG. 6, the dye-excluding "side population" of Huh6 and Huh7 cells expressed elevated levels of GAST mRNA compared to the general population of such cells grown as spheroids under low adherence culture conditions (FIGS. 6A and 6B, respectively). The side population of Huh7 cells expressed more gastrin mRNA compared to the side population of Huh6 cells. Results are expressed relative to GAST gene expression levels in SW480 cells.

Example 9: PLC/PRL/5 Hepatocellular Carcinoma Cells Grown Under Spheroid Growth Conditions Form Fewer Spheroids when Treated with an Anti-PG Antibody This example shows the effect on growth as spheroids under low adherence culture conditions of PLC/PRL/5 liver cancer cells of treatment with anti-hPG monoclonal antibodies.

A. Methods

PLC/PRL/5 hepatocellular carcinoma cells were seeded in ultra low-adherence 24-well plates (220 cells/well) in serum-free M11 medium (DMEM/F12 with 20 ng/ml EGF, 10 ng/ml FGF, 20 µg/ml insulin, N2 supplement, 2 µg/ml ciprofloxacin, 5 µg/ml gentamycin and 3 µg/ml glucose). Cells were grown for 10 days at 37° C., with the daily addition of control or anti-hPG MAb3 monoclonal antibodies (1 µg/ml). At the end of the experiment, photomicrographs were taken, and the number of spheres per well counted and the mean and standard deviation calculated.

B. Results

As shown in FIG. 7, treatment with anti-hPG monoclonal antibodies of PLC/PRF/5 cells substantially reduced the number of spheroids that formed during growth under low adherence culture conditions compared to control monoclonal antibody.

Example 10: Side Population Cells Purified from Huh6 Hepatoblastoma Cell Line Grown Under Spheroid Growth Conditions Form Fewer Spheroids when Treated with an Anti-PG Antibody This example shows the effect on growth as spheroids under low adherence culture conditions of the dye excluding side population of Huh6 liver cancer cells of treatment with anti-hPG polyclonal antibodies.

A. Methods

The dye excluding side population cells of Huh6 cells were isolated as described above. Side population cells were then seeded into ultra low adherence 96-well plates (200 cells/well) in M11 medium, and grown for 13 days at 37° C. in the presence of control or anti-progastrin polyclonal antibodies (1 µg/ml), 5 nM doxorubicin (a chemotherapeutic agent used in certain liver cancer therapy), or DMSO (vehicle for doxorubicin) (15 wells per condition). The composition of M11 medium was as follows: DMEM/F12-Glutamax (Catalog #31331 Invitrogen); 20 ng/ml EGF (R&D systems); 10 ng/ml FGF (R&D systems); 20 microg/ml Insulin (Sigma); 1/100 dilution of N2 supplement (Catalog #P1510, Gibco); 2 µg/ml ciprofloxacin, 5 µg/ml gentamycin and 3 µg/ml glucose. At the end of the experiment, photomicrographs were taken, and the number of spheres per well counted and the mean and standard deviation calculated.

B. Results

As shown in FIG. 8, treatment with anti-hPG polyclonal antibodies of side population cells purified from the Huh6 cell line substantially reduced the number of spheroids that formed during growth under low adherence culture conditions compared to control antibodies, doxorubicin and DMSO control.

Example 11: Side Population Cells Purified from Huh7 Hepatocellular Cell Line Grown Under Spheroid Growth Conditions Form Fewer Spheroids when Treated with an Anti-hPG Antibody This example shows the effect of treatment with anti-hPG polyclonal antibodies on growth as spheroids under low adherence culture conditions of the dye excluding side population of Huh7 liver cancer cells.

A. Methods

The dye excluding side population cells of Huh7 cells were isolated as described in Example 8. Side population cells were then seeded into ultra low adherence 96-well plates (200 cells/well) in M11 medium, and grown for 9 days at 37° C. in the presence of control or anti-progastrin polyclonal antibodies (1 µg/ml), 5 nM doxorubicin (a chemotherapeutic agent used in certain liver cancer therapy), or DMSO (vehicle for doxorubicin) (15 wells per condition). The composition of M11 medium was as follows: DMEM/F12-Glutamax (Catalog #31331 Invitrogen); 20 ng/ml EGF (R&D systems); 10 ng/ml FGF (R&D systems); 20 microg/ml Insulin (Sigma); 1/100 dilution of N2 supplement (Catalog #P1510, Gibco); 2 µg/ml ciprofloxacin, 5 µg/ml gentamycin and 3 µg/ml glucose. At the end of the experiment, photomicrographs were taken, and the number of spheres per well counted and the mean and standard deviation calculated.

B. Results

As shown in FIG. 9, treatment with anti-hPG polyclonal antibodies of side population cells purified from the Huh7 cell line substantially reduced the number of spheroids that formed during growth under low adherence culture conditions compared to control antibodies and DMSO control. Doxorubicin was also seen to reduce the number of spheroids that formed in culture.

Example 12: Huh6 Hepatoblastoma Cells Form Fewer Spheroids Under Low Adherence Growth Conditions when Treated with an Anti-hPG Monoclonal Antibody This example shows the effect of anti-hPG monoclonal antibodies on the growth of Huh6 spheroids under low adherence growth conditions.

A. Methods

Huh-6 hepatoblastoma cells were seeded in ultra low-adherence 96-well plates (85 cells/well) in serum-free M11 medium (DMEM/F12 with 20 ng/ml EGF, 10 ng/ml FGF, 20 µg/ml insulin, N2 supplement, 2 µg/ml ciprofloxacin, 5 µg/ml gentamycin and 3 µg/ml glucose). Cells were treated twice daily for 7 days at 37° C. with vehicle (PBS, Control) or with anti-hPG MAb13 or MAb19 monoclonal antibodies (3 µg/ml). At the end of the experiment, photomicrographs were taken, and the number of spheroids per well counted and the median and percentile distribution calculated and graphed.

B. Results

As shown in FIG. 10, treatment of Huh6 cells with anti-hPG monoclonal antibodies substantially reduced the number of spheroids that formed during growth under low adherence culture conditions as compared to untreated control cells.

Example 13: Huh6 Cells Pre-Treated with Anti-hPG Monoclonal Antibodies Form Fewer Spheroids when Grown Under Low Adherence Conditions This example demonstrates the inhibitory effect of pre-treatment with an anti-hPG monoclonal antibody on the subsequent ability of Huh6 hepatoblastoma cells to grow as spheroids under low adherence culture conditions.

A. Methods 100,000 Huh6 hepatoblastoma cells/well were first seeded into 6-well plates in DMEM with 10% FCS, serum starved overnight and grown for 48 hours in DMEM in the presence of 10 µg/mL anti-progastrin monoclonal antibody MAb8 or MAb13 or a control monoclonal antibody (PCX63Ag8, ATCC, Ref TIB-9). At the end of treatment, for each treatment group, 500 cells/well were plated into eight wells of ultra low-adherence 24-well plates in 500 µl of serum-free M11 medium containing bFGF and EGF, and grown for a further 5 days without treatment. At the end of this period, photographs were taken, the number of spheres per well was counted, and sphere surface was measured. Photos were taken at the end of the 5-day "washout" period, during which Huh-6 cells from all original treatment conditions were grown in the same M11 medium. Thereafter, an operator who was blinded to the identity of all wells counted the spheres.

B. Results

As shown in FIG. 11, the ability of Huh6 hepatoblastoma cells to grow as spheroids in low-adherence plates was significantly reduced by the prior 48-hour treatment with a monoclonal antibody against progastrin.

Example 14: Huh7 Hepatocellular Carcinoma Cells Grown Under Spheroid Growth Conditions Form Fewer Spheroids when Treated with an Anti-PG Monoclonal Antibody This example shows the effect of anti-hPG monoclonal antibodies on the formation of spheroids of Huh7 cells in low adherence culture conditions.

A. Methods

In a first experiment, Huh7 hepatocellular carcinoma cells were seeded in ultra low-adherence 24-well plates (500 cells/well) in serum-free M11 medium (DMEM/F12 with 20 ng/ml EGF, 10 ng/ml FGF, 20 µg/ml insulin, N2 supplement, 2 µg/ml ciprofloxacin, 5 µg/ml gentamycin and 3 µg/ml glucose). Cells were treated twice daily for 7 days at 37° C. with vehicle (PBS, Control) or with 3 µg/ml anti-hPG MAb13 monoclonal antibody (anti-hPG MAb 13). At the end of the experiment, photomicrographs were taken, and the number of spheres per well counted and the median and percentile distribution calculated.

In a second experiment, Huh7 hepatocellular carcinoma cells were seeded in ultra low-adherence 24-well plates (500 cells/well) in serum-free M11 medium (DMEM/F12 with 20 ng/ml EGF, 10 ng/ml FGF, 20 µg/ml insulin, N2 supplement, 2 µg/ml ciprofloxacin, 5 µg/ml gentamycin and 3 µg/ml glucose). Cells were treated twice daily for 7 days at 37° C. with 6 µg/ml of one of: a control monoclonal antibody (Control MAb, (P3X63Ag8, ATCC, Ref TIB-9), anti-hPG MAb13, or anti-hPG MAb16 monoclonal antibodies. At the end of the experiment, photomicrographs were taken, and the number of spheres per well counted and the median and percentile distribution calculated.

B. Results

In the first experiment, shown in FIG. 12A, treatment of Huh7 cells with anti-hPG monoclonal antibody MAb13 substantially reduced the number of spheroids that formed during growth under low adherence culture conditions as compared to untreated control cells.

In the second experiment, shown in FIG. 12B, treatment of Huh7 cells with anti-hPG monoclonal antibody MAb13 or antibody MAb16 substantially reduced the number of spheroids that formed during growth under low adherence culture conditions as compared to cells treated with a control monoclonal antibody.

Example 15: Huh7 Hepatocellular Carcinoma Cells Pre-Treated with Anti-hPG Monoclonal Antibodies Form Fewer Spheroids when Grown Under Low Adherence Conditions This example shows the inhibitory effect of pre-treatment with an anti-progastrin monoclonal antibody on the ability of Huh7 hepatocellular carcinoma cells to form spheroids under low adherence culture conditions.

A. Methods

In one experiment, 75,000 Huh7 hepatocellular carcinoma cells/well were first seeded into 6-well plates in MEMα with 10% FCS, serum starved overnight and grown for 60 hours in MEMα+0.5% Pannexin H in the presence of 10 µg/mL anti-progastrin monoclonal antibody MAb8 or control monoclonal antibody (P3X63Ag8, ATCC, Ref TIB-9). At the end of treatment, for each treatment group, 500 cells/well were plated into eight wells of ultra low-adherence 24-well plates in 500 µl of serum-free M11 medium containing bFGF and EGF, and grown for a further 5 days without treatment. At the end of this period, photographs were taken, the number of spheres per well was counted, and sphere surface was measured. Photos were taken at the end of the 5-day "washout" period, during which Huh-7 cells from all original treatment conditions were grown in the same M11 medium. Thereafter, an operator who was blinded to the identity of all wells counted the spheroids.

In a second experiment, 75,000 Huh7 hepatocellular carcinoma cells/well were first seeded into 6-well plates in MEMα with 10% FCS, serum starved overnight and grown for 60 hours in MEMα+0.5% Pannexin H in the presence of 10 µg/mL anti-progastrin monoclonal antibody MAb16 or a control monoclonal antibody (P3X63Ag8, ATCC, Ref TIB-9). At the end of treatment, for each treatment group, 500 cells/well were plated into eight wells of ultra low-adherence 24-well plates in 500 µl of serum-free M11 medium containing bFGF and EGF, and grown for a further 5 days without treatment. At the end of this period, photographs were taken, the number of spheres per well was counted, and sphere surface was measured. Photos were taken at the end of the 5-day "washout" period, during which Huh-7 cells from all original treatment conditions were grown in the same M11 medium. Thereafter, an operator who was blinded to the identity of all wells counted the spheroids.

B. Results

Results are shown in FIG. 13A-B. As shown in FIG. 13A, the ability of Huh7 cells to grow as spheroids in low-adherence plates was significantly reduced by a 48-hour pre-treatment with anti-hPG MAb8. As shown in FIG. 13B, the ability of Huh7 cells to grow as spheroids in low-adherence plates was significantly reduced by a 48-hour pre-treatment with anti-hPG MAb16.

Example 16: Huh7 Hepatocellular Carcinoma "Side Population" Cells Form Fewer Spheroids Under Low-Adherence Culture Conditions when Treated with an Anti-PG Antibody This example shows the effect of treatment with anti-hPG monoclonal antibodies on the growth of spheroids under low adherence culture conditions of dye-excluding "side population" cells from the Huh7 liver cancer cell line.

A. Methods

The dye excluding side population cells of Huh7 cells were isolated as described in Example 8. Side population cells were then seeded into ultra low adherence 24-well plates (1000 cells/well) in M11 medium, and grown for 7 days at 37° C. in the presence of control medium or anti-progastrin monoclonal antibodies MAb8 or MAb13 (6 µg/ml) (8 wells per condition). The composition of M11 medium was as follows: DMEM/F12-Glutamax (Catalog #31331 Invitrogen); 20 ng/ml EGF (R&D systems); 10 ng/ml FGF (R&D systems); 20 microg/ml Insulin (Sigma); 1/100 dilution of N2 supplement (Catalog #P1510, Gibco); 2 µg/ml ciprofloxacin, 5 µg/ml gentamycin and 3 µg/ml glucose. At the end of the experiment, photomicrographs were taken, and the number of spheres per well counted and the mean and standard deviation calculated.

B. Results

As shown in FIG. 14, treatment with anti-hPG monoclonal antibodies of side population cells purified from the Huh7 cell line substantially reduced the number of spheroids that formed during growth under low adherence culture conditions compared to cells grown in control medium.

Example 17: PLC/PRL/5 Hepatocellular Carcinoma Cells Treated with an Anti-PG Antibody Form Fewer Spheroids Under Low Adherence Growth Conditions This example shows the effect of anti-hPG monoclonal antibodies on the formation of spheroids of PLC/PRL/5 cells under low adherence culture conditions.

A. Methods

In one experiment, PLC/PRL/5 hepatocellular carcinoma cells were seeded in ultra low-adherence 96-well plates (35 cells/well) in serum-free M11 medium (DMEM/F12 with 20 ng/ml EGF, 10 ng/ml FGF, 20 µg/ml insulin, N2 supplement, 2 µg/ml ciprofloxacin, 5 µg/ml gentamycin, and 3 µg/ml glucose). Cells were treated twice daily for 8 days at 37° C. with 3 µg/ml of either a control monoclonal antibody (Control MAb, P3X63Ag8, ATCC, Ref TIB-9) or anti-hPG MAb19 monoclonal antibodies. At the end of the experiment, photomicrographs were taken, and the number of spheres per well counted and the median and percentile distribution calculated.

In another experiment, PLC/PRL/5 hepatocellular carcinoma cells were seeded in ultra low-adherence 24-well plates (200 cells/well) in serum-free M11 medium (DMEM/F12 with 20 ng/ml EGF, 10 ng/ml FGF, 20 µg/ml insulin, N2 supplement, 2 µg/ml ciprofloxacin, 5 µg/ml gentamycin and 3 µg/ml glucose). Cells were treated twice daily for 7 days at 37° C. with 6 µg/ml of either Control MAb or anti-hPG MAb13 monoclonal antibodies. At the end of the experiment, photomicrographs were taken, and the number of spheres per well counted and the median and percentile distribution calculated.

In a further experiment, PLC/PRL/5 hepatocellular carcinoma cells were seeded in ultra low-adherence 24-well plates (200 cells/well) in serum-free M11 medium (DMEM/F12 with 20 ng/ml EGF, 10 ng/ml FGF, 20 µg/ml insulin, N2 supplement, 2 µg/ml ciprofloxacin, 5 µg/ml gentamycin and 3 µg/ml glucose). Cells were treated twice daily for 7 days at 37° C. with 6 µg/ml of one of: Control MAb, anti-hPG MAb8 or anti-hPG MAb13 monoclonal antibodies. At the end of the experiment, photomicrographs were taken, and the number of spheres per well counted and the median and percentile distribution calculated.

B. Results

Results are shown in FIG. 15A-C. As shown in FIG. 15A, treatment with anti-hPG MAb19 significantly reduced the number of spheroids formed by PLC/PRL/5 cells during growth under low adherence culture conditions compared to cells treated with control MAb. As shown in FIG. 15B, treatment with anti-hPG MAb13 significantly reduced the number of spheroids formed by PLC/PRL/5 cells under low adherence culture conditions as compared to cells treated with control MAb. As shown in FIG. 15C, treatment with anti-hPG MAb8 or MAb13 significantly reduced the number of spheroids formed by PLC/PRL/5 cells under low adherence culture conditions as compared to cells treated with control MAb.

Example 18: PLC/PRF/5 Cells Pre-Treated with Anti-hPG Monoclonal Antibodies Form Fewer Spheroids when Grown Under Low Adherence Conditions This example shows the inhibitory effect of anti-hPG monoclonal antibody pretreatment on the ability of hepatocellular carcinoma cells to form spheroids under low adherence culture conditions.

A. Methods 50,000 PLC/PRF/5 hepatocellular carcinoma cells/well were first seeded into 6-well plates in EMEM with 10% FCS, serum starved overnight and grown for 72 hours in EMEM+0.5% Pannexin H in the presence of 10 µg/mL anti-hPG MAb8, anti-hPG MAb16 or a control monoclonal antibody (Control MAb, P3X63Ag8, ATCC, Ref TIB-9). At the end of treatment, for each treatment group, 200 cells/well were plated into eight wells of ultra low-adherence 24-well plates in 500 µl of serum-free M11 medium containing bFGF and EGF, and grown for a further 5 days without treatment. At the end of this period, photographs were taken, the number of spheres per well was counted, and sphere surface was measured. Photos were taken at the end of the 5-day "washout" period, during which PLC/PRF/5 cells from all original treatment conditions were grown in the same M11 medium. Thereafter, an operator who was blinded to the identity of all wells counted the spheroids.

B. Results

As shown in FIG. 16, the ability of PLC/PRF/5 hepatocellular carcinoma cells to form spheroids in low-adherence plates was significantly reduced by the prior 72-hour treatment with two different monoclonal antibodies against progastrin as compared to Control MAb.

Example 19: PLC/PRL/5 Hepatocellular Carcinoma "Side Population" Cells Form Fewer Spheroids Under Low-Adherence Culture Conditions when Treated with an Anti-PG Antibody This example shows the effect of anti-hPG monoclonal antibodies on the formation of spheroids under low adherence culture conditions by dye-excluding "side population" cells isolated from PLC/PRL/5 liver cancer cells.

A. Methods

The dye excluding side population cells of PLC/PRL/5 cells were isolated as described in Example 8. Side population cells were then seeded into ultra low adherence 24-well plates (400 cells/well) in M11 medium, and grown for 7 days at 37° C. in the presence of control medium or anti-progastrin monoclonal antibodies MAb13 (6 µg/ml) or MAb16 (10 µg/ml) (6 wells per condition). The composition of M11 medium was as follows: DMEM/F12-Glutamax (Catalog #31331 Invitrogen); 20 ng/ml EGF (R&D systems); 10 ng/ml FGF (R&D systems); 20 microg/ml Insulin (Sigma); 1/100 dilution of N2 supplement (Catalog #P1510, Gibco); 2 µg/ml ciprofloxacin, 5 µg/ml gentamycin and 3 µg/ml glucose. At the end of the experiment, photomicrographs were taken, and the number of spheres per well counted and the mean and standard deviation calculated.

B. Results

As shown in FIG. 17, treatment of "side population" cells isolated from the PLC/PRL/5 cell line with anti-hPG monoclonal antibodies substantially reduced the number of spheroids formed under low adherence culture conditions as compared to cells grown in medium alone.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of reducing recurrence of liver cancer in a subject, comprising:
administering to a human patient who has been treated for liver cancer an amount of a C-terminal anti-hPG monoclonal antibody sufficient to provide a therapeutic benefit,
wherein the C-terminal anti-hPG monoclonal antibody binds to human progastrin peptide (hPG) having an amino acid sequence of SEQ ID NO:20 but does not detectably bind to amidated gastrin 17 consisting of SEQ ID NO:104, glycine-extended gastrin 17 consisting of SEQ ID NO:105, or C-terminal flanking peptide (CTFP) consisting of SEQ ID NO:106, wherein binding specificity is determined by an ELISA assay, and
wherein the C-terminal anti-hPG monoclonal antibody comprises six CDRs, wherein the six CDRs are the CDRs of MAb5, MAb6, MAb7, MAb8, MAb11, MAb12, or MAb13.

2. The method of claim 1, wherein said anti-hPG monoclonal antibody comprises a heavy chain variable region in which CDR1 comprises the amino acid sequence of $V_H$ CDR 1.8 (SEQ ID NO:37), CDR2 comprises the amino acid sequence of $V_H$ CDR 2.8 (SEQ ID NO:41), and CDR3 comprises the amino acid sequence of $V_H$ CDR 3.8 (SEQ ID NO:45), and a light chain variable region in which CDR1 comprises the amino acid sequence of $V_L$ CDR 1.8 (SEQ ID NO:49), CDR2 comprises the amino acid sequence of $V_L$ CDR 2.8 (SEQ ID NO:52), and CDR3 comprises the amino acid sequence of $V_L$ CDR 3.8 (SEQ ID NO:55).

3. The method of claim 1, wherein said anti-hPG monoclonal antibody comprises a heavy chain variable region in which CDR1 comprises the amino acid sequence of $V_H$ CDR 1.13 (SEQ ID NO:38), CDR2 comprises the amino acid sequence of $V_H$ CDR2.13 (SEQ ID NO:42), and CDR3 comprises the amino acid sequence of $V_H$ CDR 3.13 (SEQ ID NO:46), and a light chain variable region in which CDR1 comprises the amino acid sequence of $V_L$ CDR 1.13 (SEQ ID NO:50), CDR2 comprises the amino acid sequence of $V_L$ CDR 2.13 (SEQ ID NO:53), and CDR3 comprises the amino acid sequence of $V_L$ CDR 3.13 (SEQ ID NO:56).

4. The method of claim 1, wherein said anti-hPG monoclonal antibody comprises heavy chain variable region comprising $mV_H.8$ (SEQ ID NO:59) and a light chain variable region comprising $mV_L.8$ (SEQ ID NO: 63).

5. The method of claim 1, wherein said anti-hPG monoclonal antibody comprises heavy chain variable region comprising $mV_H.13$ (SEQ ID NO:60) and a light chain variable region comprising $mV_L.13$ (SEQ ID NO:64).

6. The method of claim 1, in which the C-terminal anti-hPG monoclonal antibody competes for binding with a reference antibody, wherein said C-terminal anti-hPG monoclonal antibody comprises a heavy chain variable region in which CDR1 comprises the amino acid sequence of $V_H$ CDR 1.8 (SEQ ID NO:37), CDR2 comprises the amino acid sequence of $V_H$ CDR 2.8 (SEQ ID NO:41), and CDR3 comprises the amino acid sequence of $V_H$ CDR 3.8 (SEQ ID NO:45), and a light chain variable region in which CDR1 comprises the amino acid sequence of $V_L$ CDR 1.8 (SEQ ID NO:49), CDR2 comprises the amino acid sequence of $V_L$ CDR 2.8 (SEQ ID NO:52), and CDR3 comprises the amino acid sequence of $V_L$ CDR 3.8 (SEQ ID NO:55).

7. The method of claim 1, in which the C-terminal anti-hPG monoclonal antibody competes for binding with a reference antibody, wherein said C-terminal anti-hPG monoclonal antibody comprises a heavy chain variable region in which CDR1 comprises the amino acid sequence of $V_H$ CDR 1.13 (SEQ ID NO:38), CDR2 comprises the amino acid sequence of $V_H$ CDR2.13 (SEQ ID NO:42), and CDR3 comprises the amino acid sequence of $V_H$ CDR 3.13 (SEQ ID NO:46), and a light chain variable region in which CDR1 comprises the amino acid sequence of $V_L$ CDR 1.13 (SEQ ID NO:50), CDR2 comprises the amino acid sequence of $V_L$ CDR 2.13 (SEQ ID NO:53), and CDR3 comprises the amino acid sequence of $V_L$ CDR 3.13 (SEQ ID NO:56).

8. The method of claim 1, wherein the human patient has liver cancer stem cells, wherein the C-terminal anti-hPG monoclonal antibody inhibits growth of said liver cancer stem cells, and wherein said liver cancer stem cells express progastrin.

9. A method of inhibiting proliferation of a liver cancer stem cell, comprising:
exposing the cell to an amount of a C-terminal anti-hPG monoclonal antibody sufficient to inhibit its proliferation,
wherein the C-terminal anti-hPG monoclonal antibody binds to human progastrin peptide (hPG) having an amino acid sequence of SEQ ID NO:20 but does not detectably bind to amidated gastrin 17 consisting of SEQ ID NO:104, glycine-extended gastrin 17 consisting of SEQ ID NO:105, or C-terminal flanking peptide (CTFP) consisting of SEQ ID NO:106, wherein binding specificity is determined by an ELISA assay, and wherein the C-terminal anti-hPG monoclonal antibody comprises six CDRs, wherein the six CDRs are the CDRs of MAb5, MAb6, MAb7, MAb8, MAb11, MAb12, or MAb13.

10. The method of claim 9, wherein the method is carried out in vitro.

11. The method of claim 9, wherein the method is carried out in vivo.

* * * * *